(12) United States Patent
Kontermann et al.

(10) Patent No.: US 10,004,812 B2
(45) Date of Patent: Jun. 26, 2018

(54) ANTIBODY-DRUG CONJUGATES AND IMMUNOTOXINS

(71) Applicant: Oncomatryx Biopharma, S.L., Derio (ES)

(72) Inventors: Roland Kontermann, Nurtingen (DE); Klaus Pfizenmaier, Tiefenbronn (DE); Cristina Ferrer, Madrid (ES); Myriam Fabre, Barcelona (ES); Laureano Simon, Derio (ES)

(73) Assignee: Oncomatryx Biopharma, S.L., Derio (ES)

( * ) Notice: Subject to any disclaimer, the term of this patent is extended or adjusted under 35 U.S.C. 154(b) by 0 days. days.

(21) Appl. No.: 15/116,419

(22) PCT Filed: Feb. 4, 2015

(86) PCT No.: PCT/EP2015/052342
§ 371 (c)(1),
(2) Date: Aug. 3, 2016

(87) PCT Pub. No.: WO2015/118031
PCT Pub. Date: Aug. 13, 2015

(65) Prior Publication Data
US 2017/0007714 A1    Jan. 12, 2017

(30) Foreign Application Priority Data
Feb. 6, 2014  (GB) .................................. 1402009.3

(51) Int. Cl.
| | | |
|---|---|---|
| *A61K 39/395* | (2006.01) | |
| *A61K 47/48* | (2006.01) | |
| *C07K 16/28* | (2006.01) | |
| *A61K 45/06* | (2006.01) | |
| *C07K 16/30* | (2006.01) | |
| *C12N 9/24* | (2006.01) | |
| *C12N 9/96* | (2006.01) | |
| *A61K 47/65* | (2017.01) | |
| *A61K 47/60* | (2017.01) | |
| *A61K 47/68* | (2017.01) | |
| *A61K 39/00* | (2006.01) | |

(52) U.S. Cl.
CPC .... *A61K 47/48561* (2013.01); *A61K 39/3955* (2013.01); *A61K 45/06* (2013.01); *A61K 47/60* (2017.08); *A61K 47/65* (2017.08); *A61K 47/6803* (2017.08); *A61K 47/6849* (2017.08); *C07K 16/2896* (2013.01); *C07K 16/30* (2013.01); *C12N 9/2497* (2013.01); *C12N 9/96* (2013.01); *C12Y 302/02022* (2013.01); *A61K 2039/505* (2013.01); *C07K 2317/21* (2013.01); *C07K 2317/565* (2013.01); *C07K 2317/622* (2013.01); *C07K 2317/71* (2013.01); *C07K 2317/77* (2013.01)

(58) Field of Classification Search
None
See application file for complete search history.

(56) References Cited

U.S. PATENT DOCUMENTS

| | | | | |
|---|---|---|---|---|
| 5,660,827 A | * | 8/1997 | Thorpe | A61K 47/6851 424/130.1 |
| 7,097,836 B1 | * | 8/2006 | Seon | A61K 31/675 424/130.1 |
| 2011/0076263 A1 | * | 3/2011 | Theuer | C07K 16/2896 424/130.1 |

FOREIGN PATENT DOCUMENTS

| | | |
|---|---|---|
| WO | WO 2008/138561 | 11/2008 |
| WO | WO 2010/126551 | 11/2010 |
| WO | WO 2012/135517 | 10/2012 |
| WO | WO 2013/085925 | 6/2013 |
| WO | WO 2014/009774 | 1/2014 |
| WO | WO 2015/113760 A1 | 8/2015 |

OTHER PUBLICATIONS

Munoz et al (Cancer Letters 256 p. 73 (2007)).*
Brown et al (J. Immunol. May 1996; 156(9):3285-3291 (Year: 1996).*
Vajdos et al (J. Mol. Biol. Jul. 5, 2002;320(2); 415-428) (Year: 2002).*
Strome et al., The Oncologist, 2007; 12:1084-95 (Year: 2007).*
Brand et al., Anticancer Res. 2006; 26:463-70 (Year: 2006).*
Challener, "Site-Specific Conjugation of Cytotoxic Cytolysins Could Lead to Highly Effective Antibody-Drug Conjugates," *PharmTech*, pharmtech.com/print/201014?page=full &rel=canonical, Nov. 13, 2013, 2 pages.
Ferreras et al., "Use of Ribosome-Inactivating Protein from *Sambucus* for the Construction of Immunotoxins and Conjugates for Cancer Therapy," *Toxins*, vol. 3, No. 12, pp. 420-441, 2011.
Genbank Accession No. P33183, Oct. 1, 1993, 1 page.
Gilabert-Oriol et al "Immunotoxins Constructed with Ribosome-Inactivating Proteins and their Enhancers: A Lethal Cocktail with Tumor Specific Efficacy," *Current Pharmaceutical Design*, vol. 20, No. 42, pp. 6584-6643, 2014.
Muñoz et al., "In vitro and in vivo effects of an anti-mouse endoglin (CD105)-immunotoxin on the early stages of mouse B16MEL4A5 melanoma tumours," *Cancer Immunology Immunotherapy*, vol. 62, No. 3, pp. 541-551, 2013.
Van Damme et al., "Characterization and Molecular Cloning of *Sambucus nigra* Agglutinin V (Nigrin b), A GalNac-specific Type-2 Ribosome-Inactivating Protein from the Bark of Elderberry (*Sambucus nigra*)," *European Journal of Biochemistry*, vol. 237, No. 2, pp. 505-513, 1996.
Acharyya et al. "A CXCL1 paracrine network links cancer chemoresistance and metastasis." *Cell* 150(1): 165-178, 2012.
Barbieri et al. "Purification and conjugation of type 1 ribosome-inactivating proteins." *Methods in Molecular Biology: Immunotoxin Methods and Protocols* 166: 71-85, 2001.

(Continued)

*Primary Examiner* — Sheela J. Huff
(74) *Attorney, Agent, or Firm* — Klarquist Sparkman, LLP

(57) ABSTRACT

The present invention relates to conjugates, in particular antibody-drug conjugates and immunotoxins, having the formula I: A-(L-D)p (I) or a pharmaceutically acceptable salts or solvates thereof, wherein: A is an antibody that selectively binds Endoglin; L is a linker; D is a drug comprising a cytolysin or a Nigrin-b A-chain; and p is 1 to 10, and to use of such conjugates in the therapeutic treatment of tumors. Methods of producing such conjugates and components for use in such methods are disclosed.

22 Claims, 17 Drawing Sheets

(56) References Cited

OTHER PUBLICATIONS

Crawford et al. "PDGF-C mediates the angiogenic and tumorigenic properties of fibroblasts associated with tumors refractory to anti-VEGF treatment." *Cancer cell* 15(1): 21-34, 2001.
Erez et al. "Cancer-associated fibroblasts are activated in incipient neoplasia to orchestrate tumor-promoting inflammation in an NF-κb-dependent manner." *Cancer Cell* 17(2): 135-147, 2010.
Ferreras et al. "Use of ribosome-inactivating proteins from Sambucus for the construction of immunotoxins and conjugates for cancer therapy." *Toxins* 3(5): 420-441, 2011.
Fonsatti et al. "Targeting cancer vasculature via endoglin/CD105: a novel antibody-based diagnostic and therapeutic strategy in solid tumours." *Cardiovascular Res* 86(1): 12-1, 2010.
Fracasso et al. "Immunotoxins and other conjugates: Preparation and general characteristics." *Mini Reviews in Medicinal Chemistry* 4(5): 545-562, 2004.
Ghetie & Vitetta. "Chemical construction of immunotoxins." *Molecular Biotechnology* 18(3): 251-268, 2001.
Gualberto. "Brentuximab vedotin (SGN-35), an antibody-drug conjugate for the treatment of CD30-positive malignancies." *Expert Opinion Investig. Drugs* 21(2): 205-216, 2012.
Gupta et al. "Cancer metastasis: building a framework." *Cell* 127(4): 679-695, 2006.
Hanahan & Coussens. "Accessories to the crime: functions of cells recruited to the tumor microenvironment." *Cancer Cell* 21(3): 309-322, 2012.
Hanahan & Weinberg. "Hallmarks of cancer: the next generation." *cell* 144(5): 646-674, 2011.
Horimoto et al. "Emerging roles of the tumor-associated stroma in promoting tumor metastasis." *Cell adhesion & migration* 6(3): 193-203, 2012.
Hu et al. "Role of COX-2 in epithelial—stromal cell interactions and progression of ductal carcinoma in situ of the breast." *Proc. Nat. Academy of Sci.* 106(9): 3372-3377, 2009.
Hwang et al. "Cancer-associated stromal fibroblasts promote pancreatic tumor progression." *Cancer Research* 68(3): 918-926, 2008.
Joyce. "Therapeutic targeting of the tumor microenvironment." *Cancer Cell* 7(6): 513-520, 2005.
Joyce & Pollard. "Microenvironmental regulation of metastasis." *Nature Reviews Cancer* 9(4): 239-252, 2009.
Seon et al. "Endoglin-targeted cancer therapy." *Current Drug Delivery* 8(1): 135-143, 2011.
Kalluri & Zeisberg. "Fibroblasts in cancer." *Nature Reviews Cancer* 6(5): 392-401, 2006.
Kumar et al. "Breast carcinoma vascular density determined using CD105 antibody correlates with tumor prognosis." *Cancer Research* 59(4): 856-861, 1999.
Lambert & Blättler. "Purification and biochemical characterization of immunotoxins." *Immunotoxins*: Chapter 18, pp. 323-348. Kluwer Academic Publishers, Springer US, 1988.
Li et al. "Plasma levels of soluble CD105 correlate with metastasis in patients with breast cancer." *Int J Cancer* 89(2): 122-126, 2000.
Malanchi et al. "Interactions between cancer stem cells and their niche govern metastatic colonization." *Nature* 481(7379): 85-89 (plus Methods), 2012.
Marsh et al. "Antibody-toxin conjugation." *Immunotoxins*: 213-237. Springer US, 1988.
Meads et al. "Environment-mediated drug resistance: a major contributor to minimal residual disease." *Nature Reviews Cancer* 9(9): 665-674, 2009.
Medema & Vermeulen, "Microenvironmental regulation of stem cells in intestinal homeostasis and cancer." *Nature* 474(7351): 318-326, 2011.
Müller et al. "Murine endoglin-specific single-chain Fv fragments for the analysis of vascular targeting strategies in mice." *Journal of Immunological Methods* 339(1): 90-98, 2008.
Muñoz et al. "Sensitivity of cancer cell lines to the novel non-toxic type 2 ribosome-inactivating protein nigrin b." *Cancer Letters* 167(2): 163-169, 2001.
Muñoz et al. "Targeting a marker of the tumour neovasculature using a novel anti-human CD105-immunotoxin containing the non-toxic type 2 ribosome-inactivating protein nigrin b." *Cancer Letters* 256(1): 73-80, 2007.
Muñoz et al. "In vitro and in vivo effects of an anti-mouse endoglin (CD105)—immunotoxin on the early stages of mouse B16MEL4A5 melanoma tumours." *Cancer Immunology, Immunotherapy* 62(3): 541-551, 2013.
Nieman et al. "Adipocytes promote ovarian cancer metastasis and provide energy for rapid tumor growth." *Nature Medicine* 17(11): 1498-1503, 2011.
Olive et al. "Inhibition of Hedgehog signaling enhances delivery of chemotherapy in a mouse model of pancreatic cancer." *Science* 324(5933): 1457-1461, 2009.
Olumi et al. "Carcinoma-associated fibroblasts direct tumor progression of initiated human prostatic epithelium." *Cancer Research* 59(19): 5002-5011, 1999.
Orimo et al. "Stromal fibroblasts present in invasive human breast carcinomas promote tumor growth and angiogenesis through elevated SDF-1/CXCL12 secretion." *Cell* 121(3): 335-348, 2005.
Pardali et al. "Critical role of endoglin in tumor cell plasticity of Ewing sarcoma and melanoma." *Oncogene* 30(3): 334-345, 2011.
Perez-Soler et al. "Response and determinants of sensitivity to paclitaxel in human non-small cell lung cancer tumors heterotransplanted in nude mice." *Clinical Cancer Research* 6(12): 4932-4938, 2000.
Pietras & Östman. "Hallmarks of cancer: interactions with the tumor stroma." *Experimental cell research* 316(8): 1324-1331, 2010.
Riddles et al. "Ellman's reagent: 5, 5'-dithiobis (2-nitrobenzoic acid)-a reexamination." *Analytical Biochemistry* 94(1): 75-81, 1979.
Riener et al. "Quick measurement of protein sulfhydryls with Ellman's reagent and with 4, 4'-dithiodipyridine." *Analytical and Bioanalytical Chemistry* 373(4-5): 266-276, 2002.
Rüger et al. "In vitro characterization of binding and stability of single-chain Fv Ni-NTA-liposomes." *Journal of Drug Targeting* 14(8): 576-582, 2006.
Straussman et al. "Tumor microenvironment induces innate RAF-inhibitor resistance through HGF secretion." *Nature* 487(7408): 500, 2012.
Strell et al. "Fibroblasts—a key host cell type in tumor initiation, progression, and metastasis." *Upsala J Med Sci* 117(2): 187-195, 2012.
Thorpe et al. "New coupling agents for the synthesis of immunotoxins containing a hindered disulfide bond with improved stability in vivo." *Cancer Research* 47(22): 5924-5931, 1987.
Thrush et al. "Immunotoxins: an update." *Annual Review of Immunology* 14(1): 49-71, 1996.
Uneda et al. "Anti-endoglin monoclonal antibodies are effective for suppressing metastasis and the primary tumors by targeting tumor vasculature." *Int J Cancer* 125(6): 1446-1453, 2009.
Valastyan & Weinberg. "Tumor metastasis: molecular insights and evolving paradigms." *Cell* 147(2): 275-292, 2011.
Völkel et al. "Isolation of endothelial cell-specific human antibodies from a novel fully synthetic scFv library." *Biochemical Biophys Res Comm* 317(2): 515-521, 2004.
Weinberg. Excerpts from "Dialogue Replaces Monologue: Heterotypic Interactions and the Biology of Angiogenesis." *The Biology of Cancer*: Chapter 13, pp. 527-530, 546, 547, New York: Garland Science, 2007.
Wu et al. "Anti-angiogenic therapeutic drugs for treatment of human cancer." *J Cancer Mol* 4(2): 37-45, 2008.
Yabuuchi et al. "Notch signaling pathway targeted therapy suppresses tumor progression and metastatic spread in pancreatic cancer." *Cancer letters* 335(1): 41-51, 2013.
Yang et al. "The chemokine growth-regulated oncogene 1 (Gro-1) links RAS signaling to the senescence of stromal fibroblasts and ovarian tumorigenesis." *Proceedings of the National Academy of Sciences* 103(44): 16472-16477, 2006.

\* cited by examiner

B16 + IgG1 mE12 (5 µg/ml)

H1080 + IgG1 mE12 (5 µg/ml)

ANTIBODY-DRUG CONJUGATES AND IMMUNOTOXINS

CROSS REFERENCE TO RELATED APPLICATIONS

This is the § 371 U.S. National Stage of International Application No. PCT/EP2015/052342, filed Feb. 4, 2015, which was published in English under PCT Article 21(2), which in turn claims the benefit of GB Application No. 1402009.3, filed Feb. 6, 2014, which is incorporated by reference herein it its entirety.

FIELD OF THE INVENTION

The present invention relates to antibody-drug conjugates (ADCs) and Immunotoxins that target Endoglin (ENG), and to their use in medicine, e.g. in the treatment of certain cancers.

JOINT RESEARCH AGREEMENT

This application describes and claims certain subject matter that was developed under a written joint research agreement between TUBE Pharmaceuticals, GmbH and ONCOMATRYX BIOPHARMA, S.L. (previously ONCOMATRIX, S.L.), having an effective date of May 20, 2013.

BACKGROUND TO THE INVENTION

Malignant epithelial tumors are the main cancer-related cause of human death. These solid tumors frequently exhibit significant stromal reactions such as the so-called "desmoplastic stroma" or "reactive stroma", which represents 20-60% of total tumor mass and is characterized by the existence of large numbers of stromal cells and dense extracellular matrix (ECM). Recent studies have indicated the tumor-promoting roles of stromal cells, as exemplified by vascular cells, immune cells, fibroblasts, myofibroblasts, adipocytes and bone marrow-derived progenitors (1-6). In particular, considerable numbers of cancer-associated fibroblasts (CAFs) are frequently observed within tumor-associated stroma of various human cancers, including breast, lung, colon, and pancreas carcinomas (14,15). Interacting coordinately with the different components of the stroma, CAFs have the ability to promote neoangiogenesis and tumor growth; CAFs have also been shown as crucial for the development of aggressive tumors and tumor invasiveness during cancer progression (16-25); CAFs facilitate the spreading and infiltration of tumor cells in distant organs, thus contributing to formation of metastases. Importantly, the relevance of stromal cells to the failure of systemic drug delivery to tumors and to the development of drug resistance has also been indicated (7-11). The identification of cellular and molecular targets abrogating stromal-tumor cell interactions and thus attenuating tumorigenesis is currently one of the most important subjects in translational oncology. Indeed, targeting the peritumoral stroma is a fairly new strategy to treat metastatic tumors, which represent more than 90% of cancer patient mortality: only a few products have obtained therapeutic approval up to now, most of them being anti-angiogenic drugs (Avastin®; 26). Identifying and targeting other new molecules within the tumor microenvironment is then essential for increasing the efficacy of conventional therapies in combination with the stroma-based therapeutic approaches, and represent a powerful approach for cancer and metastasis treatment (12, 13).

Monoclonal antibody (MAb)—based drugs represent a great promise in the fight against cancer. This is because they allow the treatment to be aimed at a molecular level in a precise and specific way. These advantages, together with their commercial appeal (short development times, restricted competence and being easily exportable to other cancer types once they have been approved), have pushed many pharmaceutical companies to invest heavily in the development of new antibody-based molecules, as well as in the in-licensing of new molecules or technologies from biotech companies.

However, despite the clinical success of therapeutic antibodies, naked MAbs targeting cell surface tumor antigens rarely present sufficient efficacy on their own. To increase the low activity of the MAbs, novel strategies are focusing on binding them to toxic molecules. Plant and bacterial toxins as well as small chemotherapeutic molecules can be good candidates, since they are very potent and active in very small quantities.

The field of immunotoxins (ITs) and Antibody-Drug conjugates (ADCs) for the treatment of cancer has recently experienced a growing development activity by pharmaceutical companies, due to the technological advances performed during the last years, aimed at solving the problems they initially presented about immunogenicity, undesirable toxicity, production, half-life and resistance.

Immunoconjugates are made of a human, humanized or chimeric recombinant antibody, covalently linked to a cytotoxic drug. The main goal of such a structure is joining the power of small cytotoxic (300 to 1000 Da) and the high specificity of tumor-associated antigen targeted (TAA) MAbs.

The Ab must be very selective to reach the antigen, whose expression must be restricted in normal cells. The Ab also must be internalized efficiently into the cancerous cells.

The cytotoxic agent selected as the effector moiety must kill cells only after internalization and release into the cell cytoplasm. The most commonly used payloads in ADCs are DNA-harming drugs such as calicheamicins, duocarmicins, or microtubule-targeting compounds like auristatins and maitansinoids.

The Ab-cytotoxic linkers are designed to be stable systemically and to release the cytotoxic within the target cells.

TAAs are frequently cell membrane proteins that are overexpressed in diseased tissues or at least expressed sufficiently to facilitate the internalization-activated cytotoxicity. Ideally the antigen presents a restricted expression in normal tissues with a low or absent expression in vital organs. On top of this, the tumor antigen must be recognized selectively and with high affinity by an Ab.

Recent studies suggest that therapeutic agents designed to inhibit TGF-β signaling pathway at the tumor-stroma interphase could prevent cancer progression, improving prognosis and treatment. TGF-β co-receptor family is emerging as a target for cancer treatments acting on the tumor or on its neovasculature. Endoglin (ENG, CD105), an accessory protein of the type II TGF-β receptor complex, is part of this family and presents the following characteristics:

Type I homodimer membrane protein

Cell surface angiogenesis and neovascularisation-associated protein in many cancer types Overexpressed in tumor microvasculature cells, specifically in angiogenic areas of tumor No expression in normal tissue endothelium
Breast metastasis-correlated plasma levels
Internalization
Optimal accessibility from bloodstream Anti-ENG antibodies (e.g. scFvs) have been reported and their application in tumor stroma targeting strategies described. Specific binding, cell internalization and anti-tumoral effects of Doxorubicin-loaded, anti-ENG immuno-liposomes have been reported in vitro, using ENG+ cells, and in vivo in mice. ENG-targeted conjugates of anti-ENG antibodies and ricin or native nigrin b have been evaluated in mouse tumor models (27-36).

Despite these advances, there remains an unmet need for further therapeutic strategies for the treatment of tumors, including epithelial tumors, and for components for use in such therapeutic strategies. The present invention addresses these and other needs.

BRIEF DESCRIPTION OF THE INVENTION

Broadly, the present invention relates to anti-ENG antibodies, conjugates thereof and optimised payloads for use in antibody conjugate strategies. In particular, the present inventors have found that anti-ENG antibodies as described herein exhibit highly specific binding and fast and efficient internalisation. Moreover, the present inventors have found that the A chain of Nigrin b can be isolated and produced in bacterial host cells, yet retains the ability to translocate into cells and exhibits cytotoxic activity in the absence of the Nigrin-b B-chain when conjugated to a monoclonal antibody. The Nigrin-b A-chain described herein and/or cytolysin derivatives are advantageously conjugated to anti-ENG antibodies for use in the treatment of tumors.

Accordingly, in a first aspect the present invention provides a conjugate having the formula I:

$$A\text{-}(L\text{-}D)_p \qquad (I)$$

or a pharmaceutically acceptable salt or solvate thereof, wherein:
A is an antibody that selectively binds Endoglin;
L is a linker;
D is a drug comprising a cytolysin or a Nigrin-b A-chain; and
p is 1 to 10.

In some cases in accordance with this and other aspects of the present invention A is a monoclonal antibody or binding fragment thereof that selectively binds to an extracellular region of human Endoglin. In particular cases A may comprise heavy chain complementarity determining regions 1-3 (CDRH1-3) and light chain complementarity determining regions 1-3 (CDRL1-3) having the following amino acid sequences:
(i) CDRH1: SEQ ID NO: 7 or a variant thereof having up to 1 or 2 amino acid substitutions compared with the sequence of SEQ ID NO: 7;
(ii) CDRH2: SEQ ID NO: 8 or a variant thereof having up to 1 or 2 amino acid substitutions compared with the sequence of SEQ ID NO: 8;
(iii) CDRH3: SEQ ID NO: 9 or a variant thereof having up to 1 or 2 amino acid substitutions compared with the sequence of SEQ ID NO: 9;
(iv) CDRL1: SEQ ID NO: 10 or a variant thereof having up to 1 or 2 amino acid substitutions compared with the sequence of SEQ ID NO: 10;
(v) CDRL2: SEQ ID NO: 11 or a variant thereof having up to 1 or 2 amino acid substitutions compared with the sequence of SEQ ID NO: 11; and
(vi) CDRL3: SEQ ID NO: 12 or a variant thereof having up to 1 or 2 amino acid substitutions compared with the sequence of SEQ ID NO: 12.

In certain cases, CDRH1-3 comprise the amino acid sequences of SEQ ID NOS: 7-9, respectively and CDRL1-3 comprise the amino acid sequences of SEQ ID NOS: 10-12, respectively.

In certain cases, A comprises a heavy chain variable region (VH) comprising an amino acid sequence having at least 90%, 95% or 99% sequence identity with the full-length sequence of SEQ ID NO: 5.

In certain cases, A comprises a heavy chain variable region (VH) comprising the amino acid sequence of SEQ ID NO: 5.

In certain cases, A comprises a light chain variable region (VL) comprising an amino acid sequence having at least 90%, 95% or 99% sequence identity with the full-length sequence of SEQ ID NO: 6. In particular, A may comprise a light chain variable region (VL) comprising the amino acid sequence of SEQ ID NO: 6.

In certain cases, A comprises a heavy chain comprising an amino acid sequence having at least 90%, 95% or 99% sequence identity with the full-length sequence of SEQ ID NO: 3. In particular, A may comprise a heavy chain comprising the amino acid sequence of SEQ ID NO: 3.

In certain cases, A comprises a light chain comprising an amino acid sequence having at least 90%, 95% or 99% sequence identity with the full-length sequence of SEQ ID NO: 4. In particular, A may comprise a light chain comprising the amino acid sequence of SEQ ID NO: 4.

In certain cases, A may be a competitively binging anti-Endoglin antibody that is structurally different from the anti-Endoglin antibody molecules exemplified herein. For example, A may be an anti-Endoglin antibody molecule that competes with the anti-human Endoglin IgG1 antibody identified herein as "A5" for binding to immobilized recombinant human Endoglin. A5 has the heavy chain amino acid sequence of SEQ ID NO: 3 and the light chain amino acid sequence of SEQ ID NO: 4.

In certain cases, A is a monoclonal antibody or binding fragment thereof that selectively binds to an extracellular region of murine Endoglin. Conjugates that target murine Endoglin find particular use in pre-clinical testing, e.g., employing well-characterised murine models of various cancers. In particular, A may comprise heavy chain complementarity determining regions 1-3 (CDRH1-3) and light chain complementarity determining regions 1-3 (CDRL1-3) having the following amino acid sequences:
(i) CDRH1: SEQ ID NO: 19 or a variant thereof having up to 1 or 2 amino acid substitutions compared with the sequence of SEQ ID NO: 19;
(ii) CDRH2: SEQ ID NO: 20 or a variant thereof having up to 1 or 2 amino acid substitutions compared with the sequence of SEQ ID NO: 20;
(iii) CDRH3: SEQ ID NO: 21 or a variant thereof having up to 1 or 2 amino acid substitutions compared with the sequence of SEQ ID NO: 21;
(iv) CDRL1: SEQ ID NO: 22 or a variant thereof having up to 1 or 2 amino acid substitutions compared with the sequence of SEQ ID NO: 22;
(v) CDRL2: SEQ ID NO: 23 or a variant thereof having up to 1 or 2 amino acid substitutions compared with the sequence of SEQ ID NO: 23; and
(vi) CDRL3: SEQ ID NO: 24 or a variant thereof having up to 1 or 2 amino acid substitutions compared with the sequence of SEQ ID NO: 24. For example, CDRH1-3 may comprise the amino acid sequences of SEQ ID NOS: 19-21, respectively and CDRL1-3 may comprise the amino acid sequences of SEQ ID NOS: 22-24, respectively.

In certain cases, A comprises a heavy chain variable region (VH) comprising an amino acid sequence having at least 90%, 95% or 99% sequence identity with the full-length sequence of SEQ ID NO: 17, e.g. A may comprise a heavy chain variable region (VH) comprising the amino acid sequence of SEQ ID NO: 17.

In certain cases, A comprises a light chain variable region (VL) comprising an amino acid sequence having at least 90%, 95% or 99% sequence identity with the full-length sequence of SEQ ID NO: 18, e.g., A may comprise a light chain variable region (VL) comprising the amino acid sequence of SEQ ID NO: 18.

In certain cases, A comprises a heavy chain comprising an amino acid sequence having at least 90%, 95% or 99% or even 100% sequence identity with the full-length sequence of SEQ ID NO: 15.

In certain cases, A comprises a light chain comprising an amino acid sequence having at least 90%, 95% or 99% or even 100% sequence identity with the full-length sequence of SEQ ID NO: 16.

In certain cases, A may be a competitively binding anti-Endoglin antibody that is structurally different from the anti-Endoglin antibody molecules exemplified herein. For example, A may be an anti-Endoglin antibody molecule that competes with the anti-murine Endoglin IgG1 antibody identified herein as "mE12" for binding to immobilized recombinant murine Endoglin. mE12 has the heavy chain amino acid sequence of SEQ ID NO: 15 and the light chain amino acid sequence of SEQ ID NO: 16.

In accordance with this and other aspects of the present invention, D may be a cytolysin. The cytolysin may, in some cases, be a compound disclosed in WO 2008/138561 A1, the entire contents of which is expressly incorporated herein by reference (compounds disclosed therein are also referred to as Tubulysine derivatives). The cytolysin may be synthesised as described in WO 2008/138561. In certain cases, the cytolysin may be as defined in Formula I or Formula IV of WO 2008/138561 A1. In certain cases, the cytolysin may be of formula IV:

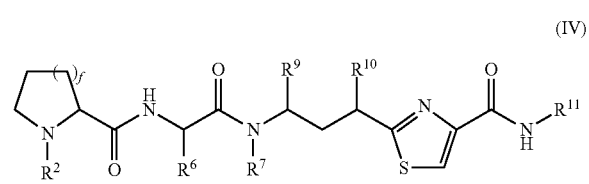

(IV)

wherein:
$R^2$ (i) is directly or indirectly attached to linker L or (ii) is H or is $C_1$-$C_4$ alkyl;
$R^6$ is $C_1$-$C_6$ alkyl;
$R^7$ is $C_1$-$C_6$ alkyl, $CH_2OR^{19}$ or $CH_2OCOR^{20}$, wherein $R^{19}$ is alkyl, $R^{20}$ is $C_2$-$C_6$-alkenyl, phenyl, or $CH_2$-phenyl;
$R^9$ is $C_1$-$C_6$ alkyl;
$R^{10}$ is H, OH, O-alkyl or O-acetyl;
f is 1 or 2;

$R^{11}$ has the following structure:

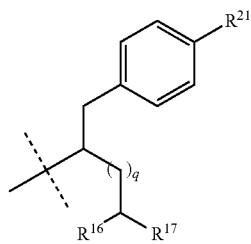

wherein
$R^{21}$ is H, OH, halogen, $NH_2$, alkyloxy, phenyl, alkyl amino or dialkyl amino;
$R^{16}$ is H or a $C_1$-$C_6$-alkyl group;
$R^{17}$ (i) is directly or indirectly attached to linker L or (ii) is $CO_2H$, $CO_2R^{18}$, $CONHNH_2$, OH, $NH_2$, SH or a optionally substituted alkyl, cycloalkyl, heteroalkyl or heterocycloalkyl group, wherein $R^{18}$ is an optionally substituted alkyl, heteroalkyl or hetercycloalkyl group; and
q is 0, 1, 2 or 3;
and wherein the term "optionally substituted" relates to groups, wherein one or several H atoms can be replaced by F, Cl, Br or I or OH, SH, $NH_2$, or $NO_2$; the term "optionally substituted" further relates to groups, which can be exclusively or additionally substituted with unsubstituted $C_1$-$C_6$ alkyl, $C_2C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

In some cases $R^2$ is a bond to linker L.

In some cases $R^{17}$ is C(O)X, CONHNHX, OX, NHX or SX, wherein X is a bond to linker L.

In some cases linker L may further comprise a spacer.

In some cases the spacer has a chain length of 2 to 30 atoms.

In some cases the spacer comprises or consists of an alkylene (i.e. divalent alkyl) or heteroalkylene (i.e. divalent heteroalkyl) group.

In some cases the spacer comprises or consists of an alkylene or oxyalkylene group.

In some cases the spacer comprises or consists of a group —$(CH_2)_n$— or —$(OCH_2CH_2)_n$—, wherein n≥1.

In some cases the spacer comprises or consists of a group —$(OCH_2CH_2)_n$—, wherein n≤1. In particular, n may be 1 to 15, 1 to 10, 1 to 6, or 2 to 5. For example, n may be 3 or 4.

In some cases the space comprises between one and six ethylene glycol units, e.g. a triethylene glycol.

In some cases the spacer may be directly attached to group $R^{17}$, or may be attached to group $R^{17}$ via a bridging group.

In some cases the spacer is attached to group $R^{17}$ via a —C(O)X bridging group, wherein X is a bond to $R^{17}$.

In some cases $R^{17}$ is CONHNHX and the spacer is attached to group $R^{17}$ via a —C(O)X bridging group, wherein X represents the bond between the spacer and $R^{17}$.

In some cases $R^{17}$ is CONHNHX and the spacer is a —$(OCH_2CH_2)_n$— attached to $R^{17}$ via a —C(O)X bridging group, wherein n=2, 3 or 4.

In some cases D comprises a cytolysin having the following structure:

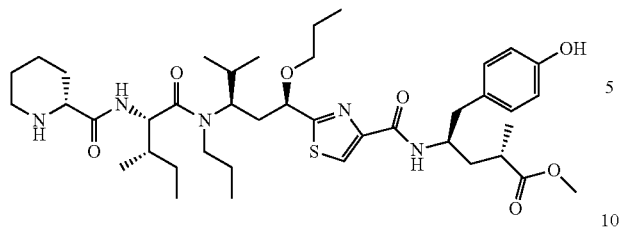

In some cases D comprises a cytolysin having the following structure:

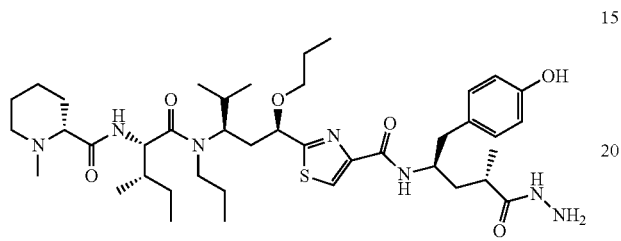

In certain cases L comprises an attachment group for attachment to A and protease cleavable portion. For example, L may comprise a valine-citrulline unit. In particular, L may comprise maleimidocaproyl-valine-citrulline-p-aminobenzylcarbamate.

In some cases the double bond of the maleimide is reacted with a thiol group of a cysteine residue of the antibody A to form a sulphur-carbon bond in order to effect linkage of the linker L to the antibody A.

In some cases -L-D has a structure selected from the group consisting of:

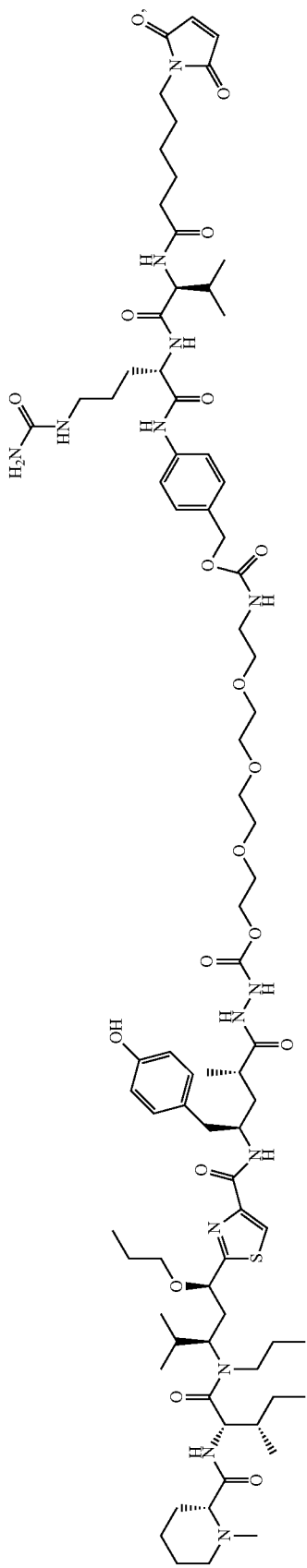
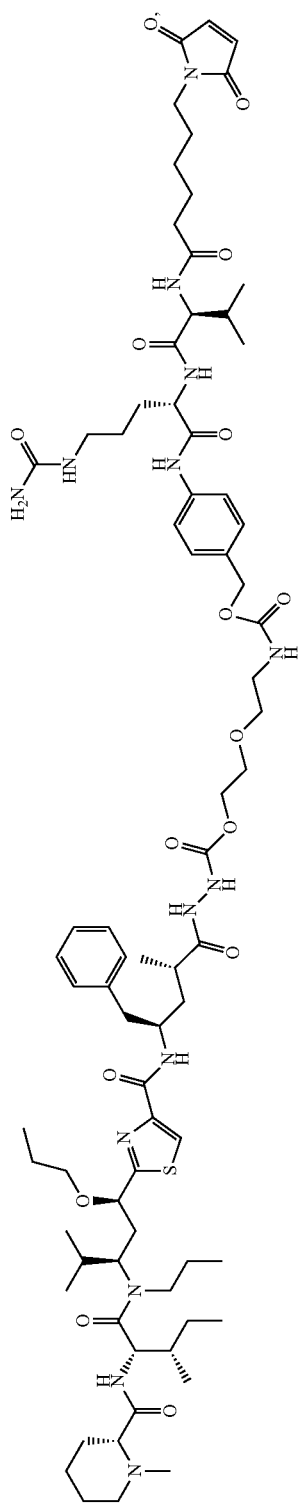
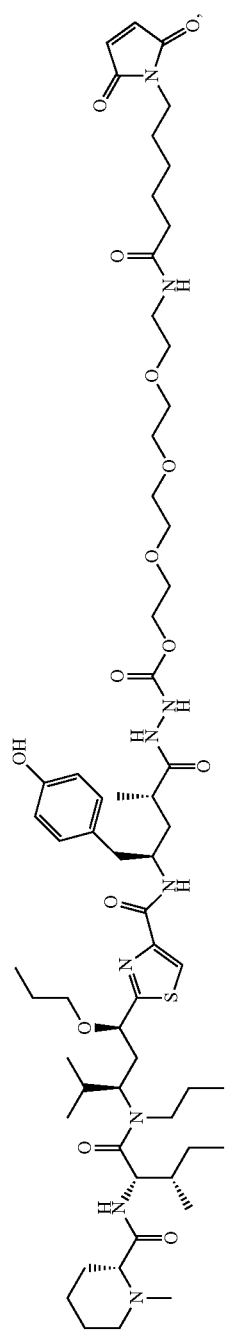

-continued
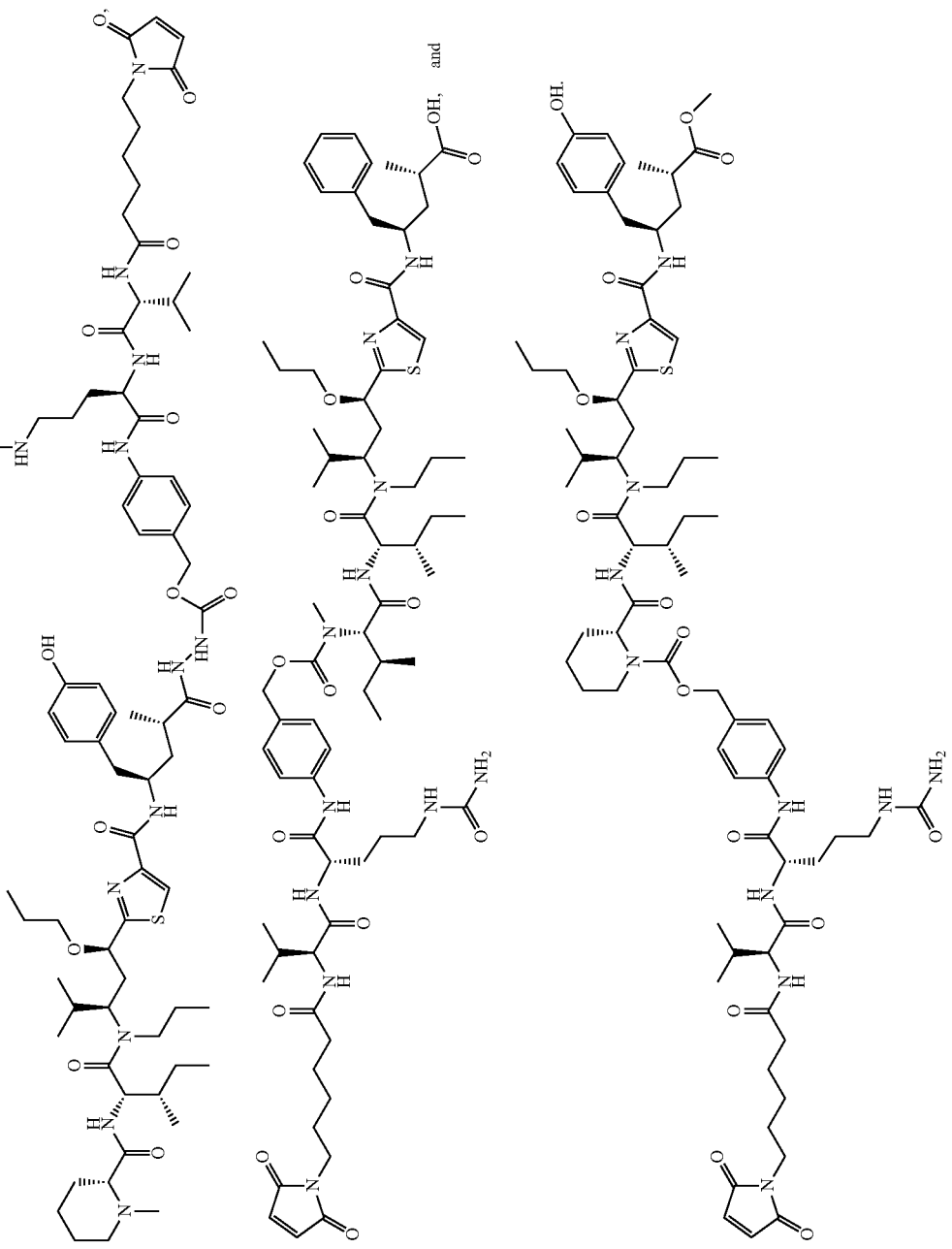

In certain cases -L-D may have the following structure:

Exact Mass: 1369.74

In certain cases -L-D may have the following structure:

Exact Mass: 1383.76
Mol. Wt.: 1384.73

In accordance with this and other aspects of the present invention p may, in some cases, lie in the range 1 to 5, e.g. 1 to 4, or 1 to 3. In particular cases p may be 1 or 2. In particular, cases p may be 3 or 4.

In accordance with this and other aspects of the present invention D may be a Nigrin-b A-chain. Preferably, the Nigrin-b A-chain is in the absence of a Nigrin-b B-chain. The Nigrin-b A-chain may comprise or consist of the sequence of SEQ ID NO: 25.

In certain cases, the Nigrin-b A-chain may be or may have been recombinantly-produced, e.g. in a bacterial host cell. The present inventors have surprisingly found that Nigrin-b A-chain retains its activity (e.g. cytotoxic and/or ribosome inhibiting activity) despite loss of or alteration of native glycosylation such as is the case when the Nigrin-b A-chain is produced recombinantly in a bacterial host cell.

When the conjugate of the present invention comprises a Nigrin-b A-chain as the toxic payload (i.e. D), L may simply be a disulphide bond between a sulphur atom on A and a sulphur atom on D. Therefore, L may comprise or consist of a bond, e.g. a disulphide bond.

In a second aspect the present invention provides a conjugate as defined in accordance with the first aspect of the invention for use in medicine.

In a third aspect the present invention provides a conjugate as defined in accordance with the first aspect of the invention for use in a method of treatment of a tumor in a mammalian subject. In certain cases the conjugate is for use in the treatment of a blood neoplasm. In other cases the conjugate is for use in the treatment of a solid tumor. In particular, the conjugate may be for use in the treatment of pancreatic cancer, Ewing sarcoma, breast cancer, melanoma, lung cancer, head & neck cancer, ovarian cancer, bladder cancer or colon cancer.

In some cases the conjugate is for simultaneous, sequential or separate administration with one or more other antitumor drugs. The one or more other antitumor drugs comprise a cytotoxic chemotherapeutic agent or an antiangiogenic agent or an immunotherapeutic agent. In some cases the one or more other antitumor drugs comprise Gemcitabine, Abraxane bevacizumab, itraconazole, carboxyamidotriazole, an anti-PD-1 molecule or an anti-PD-L1 molecule (for example, nivolumab or pembrolizumab).

In a fourth aspect the present invention provides a method of treating a tumor in a mammalian subject, comprising administering a therapeutically effective amount of a conjugate as defined in accordance with the first aspect of the invention to the subject in need thereof. In some cases the method may be for treating a blood neoplasm. In other cases the method may be for treating solid tumors. In particular, the method may be for treating pancreatic cancer, Ewing sarcoma, breast cancer, melanoma, lung cancer, head & neck cancer, ovarian cancer, bladder cancer or colon cancer.

In a fifth aspect the present invention provides use of a cytolysin in the preparation of an antibody-drug conjugate, wherein the antibody is an Endoglin-specific antibody, e.g., an Endoglin-specific antibody in accordance with the eighth aspect of the invention. In some cases the cytolysin may be as defined in accordance with the first aspect of the invention. In some case the use may be of a cytolysin in the preparation of an antibody-drug conjugate as defined in accordance with the first aspect of the invention.

In a sixth aspect the present invention provides an isolated Nigrin-b A-chain in the absence of the Nigrin-b B-chain. The amino acid sequence of the Nigrin-b A-chain may comprise or consist of the sequence of SEQ ID NO: 25.

In an seventh aspect the present invention provides use of an isolated Nigrin-b A-chain in accordance with the sixth aspect of the invention in the preparation of an immunotoxin. In some cases, the immunotoxin comprises a monoclonal antibody conjugated and/or bound to said isolated Nigrin-b A-chain. In some cases the immunotoxin comprises an antibody, such as a monoclonal antibody, e.g. a human monoclonal antibody, that selectively binds Endoglin. In some cases, the immunotoxin comprises an antibody in accordance with the eighth aspect of the invention.

In an eighth aspect the present invention provides a monoclonal antibody, e.g. a human monoclonal antibody, that:
(i) selectively binds human Endoglin and which comprises a heavy chain comprising the amino acid sequence of SEQ ID NO: 3 and a light chain comprising the amino acid sequence of SEQ ID NO: 4; or
(ii) selectively binds murine Endoglin and which comprises a heavy chain comprising the amino acid sequence of SEQ ID NO: 15 and a light chain comprising the amino acid sequence of SEQ ID NO: 16.

In a ninth aspect the present invention provides an antibody of the eighth aspect of the invention for use in medicine.

In a tenth aspect the present invention provides a conjugate of the first aspect of the invention or an antibody of the eighth aspect of the invention for use in the treatment of an inflammatory condition (e.g. rheumatoid arthritis) or an eye disease (e.g. diabetic retinopathy or macular degeneration, such as wet age related macular degeneration).

In an eleventh aspect the present invention provides a method of treating an inflammatory condition (e.g. rheumatoid arthritis) or an eye disease (e.g. diabetic retinopathy or macular degeneration, such as wet age related macular degeneration) in a mammalian subject, comprising administering a therapeutically effective amount of a conjugate of the first aspect of the invention or an antibody of the eighth aspect of the invention to the subject in need thereof.

In a twelfth aspect the present invention provides use of a monoclonal antibody in accordance with the eighth aspect of the invention in the preparation of an antibody-drug conjugate or an immunotoxin.

In a thirteenth aspect the present invention provides a host cell comprising a vector comprising a polynucleotide that encodes at least one polypeptide having an amino acid sequence selected from the group consisting of: SEQ ID NOS: 1-6, 13-18 and 25. In some cases the polynucleotide may comprise the nucleic acid sequence of SEQ ID NO: 26.

In a fourteenth aspect the present invention provides a process for the production of a conjugate in accordance with the first aspect of the invention, comprising:
(a) derivatising the antibody that selectively binds Endoglin to introduce at least one sulphydryl group; and
(b) reacting the derivatised antibody with an appropriate residue (e.g. a cysteine amino acid) on a Nigrin-b A-chain (absent a Nigrin-b B-chain) under conditions which permit the formation of a disulphide bond linkage between the antibody and the Nigrin-b A-chain thereby producing the conjugate. The process may further comprise a step (c) of purifying and/or isolating the conjugate.

In some cases step (a) may comprise reacting the antibody with 4-succynimidyloxycarbonyl-α-methyl-α-(2-pyridyldithio)toluene (SMPT), N-succynimidyl 3-(2-pyridyl-dithiopropionate) (SPDP) or methyl 4-mercaptobutyrimidate.

In a fifteenth aspect the present invention provides a process for the production of a conjugate in accordance with the first aspect of the invention, comprising:
(a) linking the antibody that selectively binds Endoglin to the linker via a thiol group; and
(b) linking the cytolysin to the linker via an appropriate group on the cytolysin molecule. In some cases, the cytolysin is linked to the linker via position $R_2$ or position $R_{17}$. Steps (a) and (b) can be performed in either order. In an optional further step (c), the process may comprise purifying and/or isolating the conjugate.

The present invention includes the combination of the aspects and preferred features described except where such a combination is clearly impermissible or is stated to be expressly avoided. These and further aspects and embodiments of the invention are described in further detail below and with reference to the accompanying examples and figures.

Figure 1:
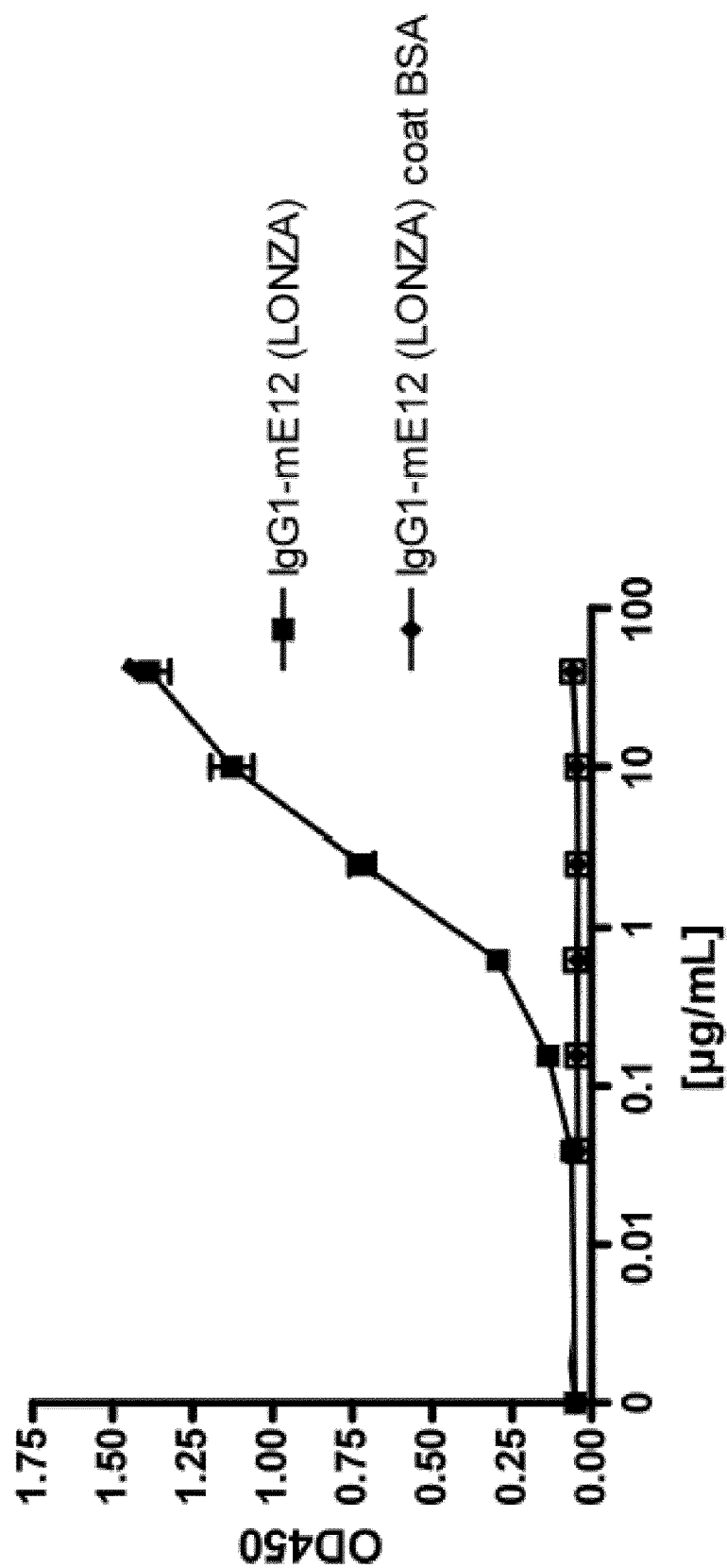
FIG. 1 shows ELISA results of mE12-IgG for binding to recombinant mouse ENG (aa 27-581). Coated BSA was included as negative control. A concentration-dependent binding to mouse ENG was observed.

Cytotoxic chemotherapeutic agents are well known in the art and include anti-cancer agents such as:
Alkylating agents including nitrogen mustards such as mechlorethamine (HN2), cyclophosphamide, ifosfamide, melphalan (L-sarcolysin) and chlorambucil; 10 ethylenimines and methylmelamines such as hexamethylmelamine, thiotepa; alkyl sulphonates such as busulfan; nitrosoureas such as carmustine (BCNU), lomustine (CCNLJ), semustine (methyl-CCN-U) and streptozoein (streptozotocin); and triazenes such as decarbazine (DTIC; dimethyltriazenoimidazolecarboxamide);
Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycofonnycin). Natural Products including vinca alkaloids such as vinblastine (VLB) and vincristine; epipodophyllotoxins such as etoposide and teniposide; antibiotics such as dactinomycin (actinomycin D), daunorabicin (daunomycin; rubidomycin), doxorubicin, bleomycin, plicamycin (mithramycin) and mitomycin (mitomycin Q; enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and antbracycline; substituted urea such as hydroxyurea; methyl hydrazine derivative such as procarbazine (N-methylhydrazine, MIH); and adrenocortical suppressant such as mitotane (o, p'-DDD) and aminoglutethimide; taxol and analogues/derivatives; and hormone agonists/antagonists such as flutamide and tamoxifen. A further preferred cytotoxic agent is Gemcitabine (Gemzar®). A further preferred cytotoxic agent is Paclitaxel bound to human serum albumin (Abraxane®).

Anti-angiogenic agents are well known in the art and include anti-cancer agents such as bevacizumab, itraconazole, and carboxyamidotriazole.

Immunotherapeutic agents are known in the art and include, for example, anti-programmed cell death protein 1 (PD-1) antibodies and anti-programmed death-ligand 1 (PD-L1) antibodies, including Nivolumab (MDX1106) and Pembrolizumab (MK-3475).

Pharmaceutical Compositions

The conjugates of the present invention may be comprised in pharmaceutical compositions with a pharmaceutically acceptable excipient.

A pharmaceutically acceptable excipient may be a compound or a combination of compounds entering into a pharmaceutical composition which does not provoke secondary reactions and which allows, for example, facilitation of the administration of the conjugate, an increase in its lifespan and/or in its efficacy in the body or an increase in its solubility in solution. These pharmaceutically acceptable vehicles are well known and will be adapted by the person skilled in the art as a function of the mode of administration of the conjugate.

In some embodiments, conjugates of the present invention may be provided in a lyophilised form for reconstitution prior to administration. For example, lyophilised conjugates may be re-constituted in sterile water and mixed with saline prior to administration to an individual.

Conjugates of the present invention will usually be administered in the form of a pharmaceutical composition, which may comprise at least one component in addition to the conjugate. Thus pharmaceutical compositions may comprise, in addition to the conjugate, a pharmaceutically acceptable excipient, carrier, buffer, stabilizer or other materials well known to those skilled in the art. Such materials should be non-toxic and should not interfere with the efficacy of the conjugate. The precise nature of the carrier or other material will depend on the route of administration, which may be by bolus, infusion, injection or any other suitable route, as discussed below.

For intra-venous administration, e.g. by injection, the pharmaceutical composition comprising the conjugate may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Subject

The subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human. In some cases the subject may be a human diagnosed with or classified as being at risk of developing a cancer, e.g., an epithelial tumor, a solid tumor or a blood neoplasm. In certain cases the subject may be a laboratory animal, e.g., a mouse model of a cancer. In certain cases the subject may be a mammal (e.g. a human) that has been diagnosed with or classified as being at risk of developing an inflammatory condition, such as osteoarthritis or rheumatoid arthritis (RA). In particular, the subject may be a human having osteoarthritis or RA. In certain cases the subject may be a mammal (e.g. a human) that has been diagnosed with or classified as being at risk of developing an eye disease, such as diabetic retinopathy or macular degeneration.

Cancer

The anti-ENG conjugates described herein find use in the treatment of a tumor in a mammalian subject. The tumor may be a solid tumor. In particular, the tumor may be a pancreatic cancer, breast cancer, melanoma, Ewing sarcoma, lung cancer, head & neck cancer, ovarian cancer, bladder cancer or colon cancer.

Inflammatory Condition

In some cases in accordance with the present invention, the anti-ENG antibody or the antibody drug conjugate may be for use in the treatment of an inflammatory condition.

ENG expression has been reported in osteoarthritis and rheumatoid arthritis. See, e.g., Szekanecz, Z. et al. Clinical Immunology and Immunopathology, 1995, 76, 187-194, and Leask A et al., Arthritis & Rheumatism, 2002, 46, 1857-1865. The present inventors believe that the anti-ENG antibodies described herein, and/or conjugates thereof described herein, are able to ameliorate osteoarthritis, rheumatoid arthritis and/or symptoms of osteoarthritis or rheumatoid arthritis.

Eye Disease

In some cases in accordance with the present invention, the anti-ENG antibody or the antibody drug conjugate may be for use in the treatment of an eye disease (e.g. diabetic retinopathy or macular degeneration, such as age related macular degeneration). ENG expression has been reported in certain eye conditions, including macular degeneration and retinopathy. See, e.g., Tsutomu Yasukawa et al., Curr Eye Res. 2000, 21, 952-961, and Abu El-Asrar A M et al., Mediators Inflamm. 2012, 2012:697489, and Malik R A et al., *J Cell Mol Med.* 2005, 9:692-7. The present inventors believe that the anti-ENG antibodies described herein, and/or conjugates thereof described herein, are able to ameliorate eye diseases and/or symptoms thereof (including diabetic retinopathy or macular degeneration, such as age related macular degeneration).

The following is presented by way of example and is not to be construed as a limitation to the scope of the claims.

EXAMPLES

Example 1—Production of Anti-ENG Antibodies

Anti-ENG scFvs isolated from synthetic antibody phage libraries have been described previously (29). One scFv, directed against the extracellular region of human ENG, known as "A5" (29) and one scFv, directed against the extracellular region of murine ENG, known as "mE12" (31) were converted into full-length IgG for subsequent characterisation studies and for generation of immunotoxins and ADCs. All scFvs were produced in *E. coli* and purified by IMAC, IgGs were produced in mammalian cells (CHO) using the Lonza GS expression vectors pEE6.4 and pEE14.4 developed for antibody production. Features of the scFv starting material are summarized in Table 1.

TABLE 1 antibodies, specificities, subclass, and vectors used as starting material

| Format | Species | Antigen | Clone | Vl Subclass | Vector | Plasmid DNA # |
|---|---|---|---|---|---|---|
| scFv | human | human ENG | A5 | kappa | pAB1 | 179 |
| scFv | human | mouse ENG | mE12 | lambda | pAB1 | 151.1 |

All scFvs were bacterially produced in *E. coli* TG1 and purified from the periplasmic extracts of 1 L cultures by IMAC.

Plasmids corresponding to full length IgG1 antibodies were generated and transfected into CHO cells for production of antibodies in Lonza's CHO expressing system with yields of approximately 1 mg/L of cell culture (lab scale). Antibodies were purified from cell culture supernatant by protein A chromatography. Purified proteins were characterized by SDS-PAGE and size exclusion chromatography. Bioactivity was analyzed by ELISA using recombinant ENG and detection of bound antibodies with HRP-conjugated anti-human IgG antibodies. Cell binding was analyzed by flow cytometry using ENG-expressing mouse B16 cell.

Results:

Plasmids Generated (and Sequenced):

A5 IgG1: pEE14.4 A5-IgG1 OCMTX003p (human anti-huENG IgG1)

mE12 IgG1: pEE14.4 mE12-IgG1 OCMTOO4p (human anti-muENG IgG1)

Example 2—Characterisation of Anti-ENG Antibodies

The amino acid sequences of anti-human ENG IgG1 A5 (A5-IgG1) heavy chain (HC) and light chain (LC), respectively are shown below:

```
Anti-human Endoglin A5-IgG1-HC:
                                                  (SEQ ID NO: 1)
METDTLLLWVLLLWVPGSTG EVQLLESGGGLVQPGGSLRLSCAASGFTFSSYAMSWVRQAPGKGLEWVSAIYGSDGDTTYADSVKGRF
TISRDNSKNTLYLQMNSLRAEDTAVYYCARVFYTAGFDYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPPVAGPSVFLFPPKPKDTLMISRTPEVTCVVVDVSHEDPE
VKFNWYVDGVEVHNAKTKPREEQYNSTYRVVSVLTVLHQDWLNGKEYKCKVSNKGLPSSIEKTISKAK
GQPREPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK
aa                                                447
MW of processed HC                                48,703
Theoretical pI                                    8.36
Potential glycosylation site (double underlined): N297
Mutations leading to ADCC and CDC deficiency are shown in bold
italics (see also WO 99/58572)
Signal sequence is shown boxed
VH domain is underlined; CDRH1-H3 are shown in bold and curved
underlined.

(SEQ ID NO: 2)
METDTLLLWVLLLWVPGSTG

DIELTQSPSSLSASVGDRVTITCRASQSISSSLNWYQQKPGKAPKLLIYAASSLQSGVPSRFSGSGSG
TDFTLTISSLQPEDFATYYCQQAPAKPPTFGQGTKLEIKRTVAAPSVFIFPPSDEQLKSGTASVVCLL
```

-continued

```
NNFYPREAKVQWKVDNALQSGNSQESVTEQDSKDSTYSLSSTLTLSKADYEKHKVYACEVTHQGLSSP
VTKSFNRGEC
aa                                       214
MW of processed HC                       23,113
theoretical pI                           7.76
signal                                   sequence is boxed
VL domain is underlined; CDRL1-L3 are shown in bold and curved
underlined.
```

A5-IgG1-HC- without signal sequence:

(SEQ ID NO: 3)

<u>EVQLLESGGGLVQPGGSLRLSCAASGFTFSSYAMSWVRQAPGKGLEWVSAIYGSDGDTTYADSVKGRF
TISRDNSKNTLYLQMNSLRAEDTAVYYCARVFYTAGFDYWGQGTLVTVSS</u>ASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAP*PVA*GPSVFLFPPKPKDTLMISRTPEVTCVVVDVSHEDPE
VKFNWYVDGVEVHNAKTKPREEQY<u>N</u>STYRVVSVLTVLHQDWLNGKEYKCKVSNK*GLPSS*IEKTISKAK
GQPREPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK

A5-IgG1-LC- without signal sequence:

(SEQ ID NO: 4)

<u>DIELTQSPSSLSASVGDRVTITCRASQSISSSLNWYQQKPGKAPKLLIYAASSLQSGVPSRFSGSGSG
TDFTLTISSLQPEDFATYYCQQAPAKPPTFGQGTKLEIKR</u>TVAAPSVFIFPPSDEQLKSGTASVVCLL
NNFYPREAKVQWKVDNALQSGNSQESVTEQDSKDSTYSLSSTLTLSKADYEKHKVYACEVTHQGLSSP
VTKSFNRGEC

A5-VH:

(SEQ ID NO: 5)

EVQLLESGGGLVQPGGSLRLSCAASGFTFSSYAMSWVRQAPGKGLEWVSAIYGSDGDTTYADSVKGRF
TISRDNSKNTLYLQMNSLRAEDTAVYYCARVFYTAGFDYWGQGTLVTVSS

A5-VL:

(SEQ ID NO: 6)

DIELTQSPSSLSASVGDRVTITCRASQSISSSLNWYQQKPGKAPKLLIYAASSLQSGVPSRFSGSGSG
TDFTLTISSLQPEDFATYYCQQAPAKPPTFGQGTKLEIKR

A5-CDRH1:

(SEQ ID NO: 7)

SYAMS

A5-CDRH2:

(SEQ ID NO: 8)

AIYGSDGDTTY

A5-CDRH3:

(SEQ ID NO: 9)

VFYTAGFDY

A5-CDRL1:

(SEQ ID NO: 10)

RASQSISSSLN

A5-CDRL2:

(SEQ ID NO: 11)

AASSLQS

A5-CDRL3:

(SEQ ID NO: 12)

QQAPAKPPT

```
Parameters of the full A5-IgG are as follows:
Total length of full-length IgG (aa):      1,322
Calculated molecular mass of full-length IgG:  143,577
Calculated extinction coefficient of full-length IgG: 195,440
Abs 0.1% (= 1 g/l)                         1.361
theoretical pI:                            8.36
potential glycosylation site:              N297
```

Anti-murine Endoglin mE12-IgG1-HC:

(SEQ ID NO: 13)

METDTLLLWVLLLWVPGSTG

<u>EVQLVESGGGVVQPGRSLRLSCAASGFTFSSYGMHWVRQAPGKGLVWVS**RINSDGSSTSYADSVKGRF
TISRDNSKNTLYLQMNSLRAEDTAVYYCARATGTWVMSWGQGTLVTVSS</u>ASTKGPSVFPLAPSSKSTS
GGTAALGCLVKDYFPEPVTVSWNSGALTSGVHTFPAVLQSSGLYSLSSVVTVPSSSLGTQTYICNVNH

```
KPSNTKVDKKVEPKSCDKTHTCPPCPAPPVAGPSVFLFPPKPKDTLMISRTPEVTCVVVDVSHEDPEV
KFNWYVDGVEVHNAKTKPREEQYNSTYRVVSVLTVLHQDWLNGKEYKCKVSNKGLPSSIEKTISKAKG
QPREPQVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK
aa                                                446
MW of processed HC                                48,574
Calculated pI                                     8.88
Potential glycosylation site (double underlined): N297
Mutations leading to ADCC and CDC deficiency are shown in bold
italics
Signal sequence is shown boxed
VH domain is underlined
```

Anti-murine Endoglin mE12-IgG1-LC:
(SEQ ID NO: 14)

```
METDTLLLWVLLLWVPGSTG

SSELIQDPAVSVALGQTVRITCQGDSLRSYYASWYQQKPGQAPVLVIYGKNNRPSGIPDRFSGSSSGN
TASLTITGAQAEDEADYYCNSRDSSGTVFGGGTKLTVLGQPKANPTVTLFPPSSEELQANKATLVCLI
SDFYPGAVTVAWKADGSPVKAGVETTKPSKQSNNKYAASSYLSLTPEQWKSHRSYSCQVTHEGSTVEK
TVAPTECS
aa                                     212
MW (processed)                         22,516
Calculated pI                          6.69
Signal sequence is shown boxed
VL domain is underlined
``` mE12-IgG1-HC -without signal sequence:
(SEQ ID NO: 15)

```
EVQLVESGGGVVQPGRSLRLSCAASGFTFSSYGMHWVRQAPGKGLVWVSRINSDGSSTSYADSVKGRF
TISRDNSKNTLYLQMNSLRAEDTAVYYCARATGTWVMSWGQGTLVTVSSASTKGPSVFPLAPSSKSTS
GGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPPVAGPSVFLFPPKPKDTLMISRTPEVTCVVVDVSHEDPEV
KFNWYVDGVEVHNAKTKPREEQYNSTYRVVSVLTVLHQDWLNGKEYKCKVSNKGLPSSIEKTISKAKG
QPREPQVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGK
``` mE12-IgG1-LC-without signal sequence:
(SEQ ID NO: 16)

```
SSELIQDPAVSVALGQTVRITCQGDSLRSYYASWYQQKPGQAPVLVIYGKNNRPSGIPDRFSGSSSGN
TASLTITGAQAEDEADYYCNSRDSSGTVFGGGTKLTVLGQPKANPTVTLFPPSSEELQANKATLVCLI
SDFYPGAVTVAWKADGSPVKAGVETTKPSKQSNNKYAASSYLSLTPEQWKSHRSYSCQVTHEGSTVEK
TVAPTECS
``` mE12-VH:
(SEQ ID NO: 17)
EVQLVESGGGVVQPGRSLRLSCAASGFTFSSYGMHWVRQAPGKGLVWVSRINSDGSSTSYADSVKGRF
TISRDNSKNTLYLQMNSLRAEDTAVYYCARATGTWVMSWGQGTLVTVSS mE12-VL:
(SEQ ID NO: 18)
SSELIQDPAVSVALGQTVRITCQGDSLRSYYASWYQQKPGQAPVLVIYGKNNRPSGIPDRFSGSSSGN
TASLTITGAQAEDEADYYCNSRDSSGTVFGGGTKLTVLG mE12-CDRH1:
(SEQ ID NO: 19)
SYGMH mE12-CDRH2:
(SEQ ID NO: 20)
RINSDGSSTSYADSVKG mE12-CDRH3:
(SEQ ID NO: 21)
ATGTWVMS mE12-CDRL1:
(SEQ ID NO: 22)
QGDSLRSYYAS mE12-CDRL2:
(SEQ ID NO: 23)
GKNNRPS

```
mE12-CDRL3:

NSRDSSGTV
```
(SEQ ID NO: 24)

Figure 2A:
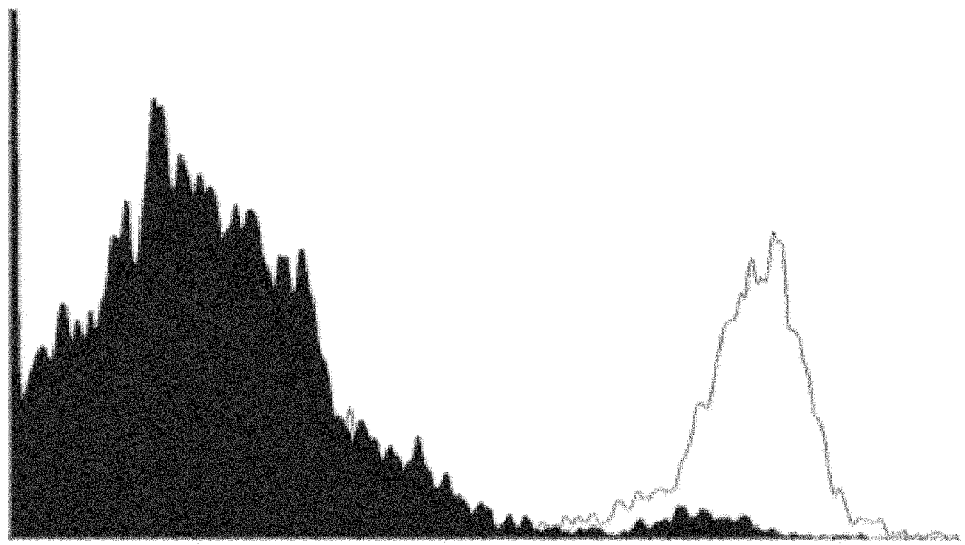
FIG. 2 shows flow cytometry analysis of binding of mE12-IgG to a) B16 cells using 50 μg/ml antibody, b) B16 cells using 5 μg/ml antibody, and c) HT1080 cells included as negative control. Shaded area: cells alone, unshaded area: cells incubated with antibody.
Figure 2B:
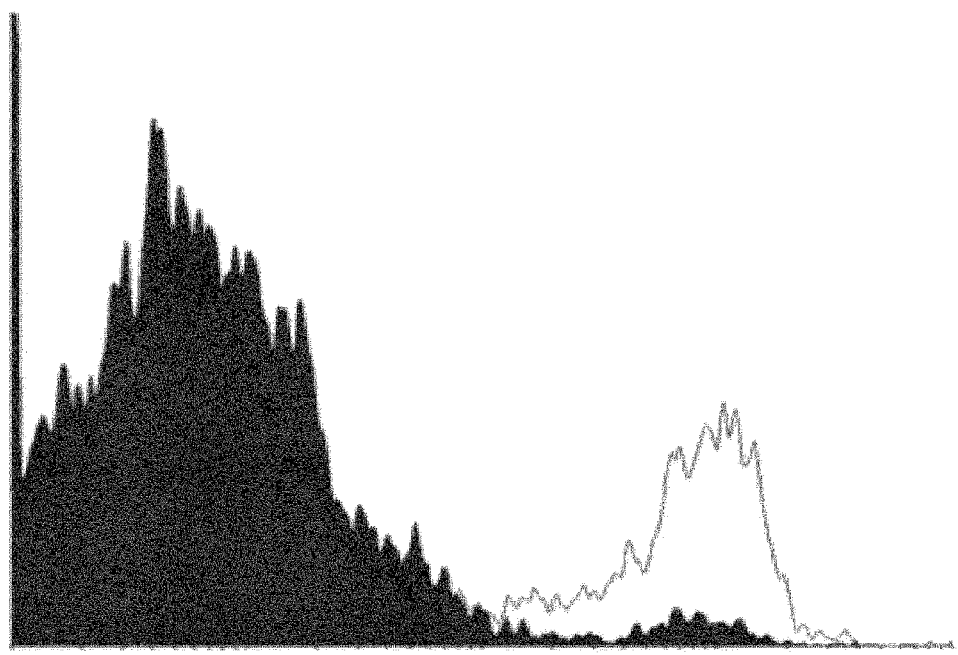
Figure 2C:
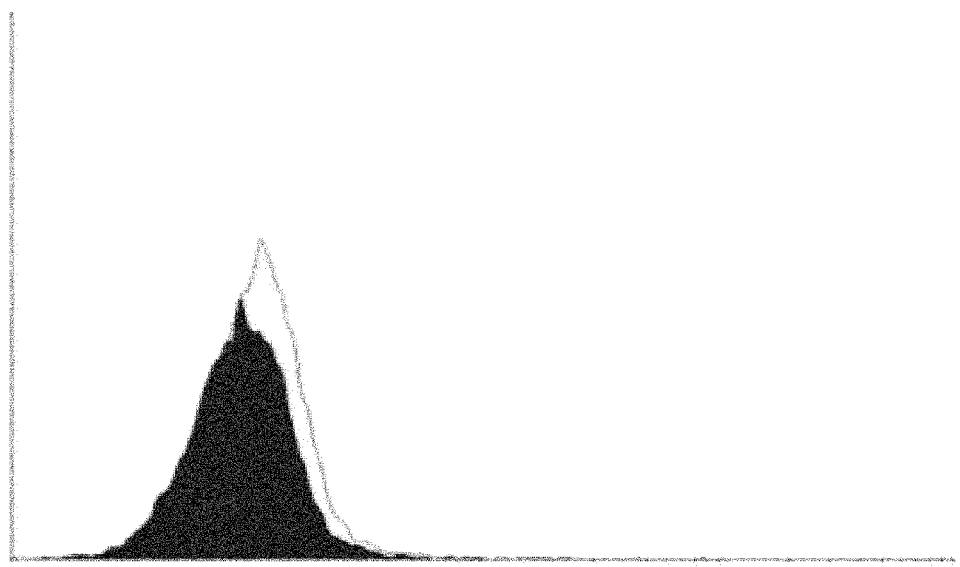
Figure 3A:
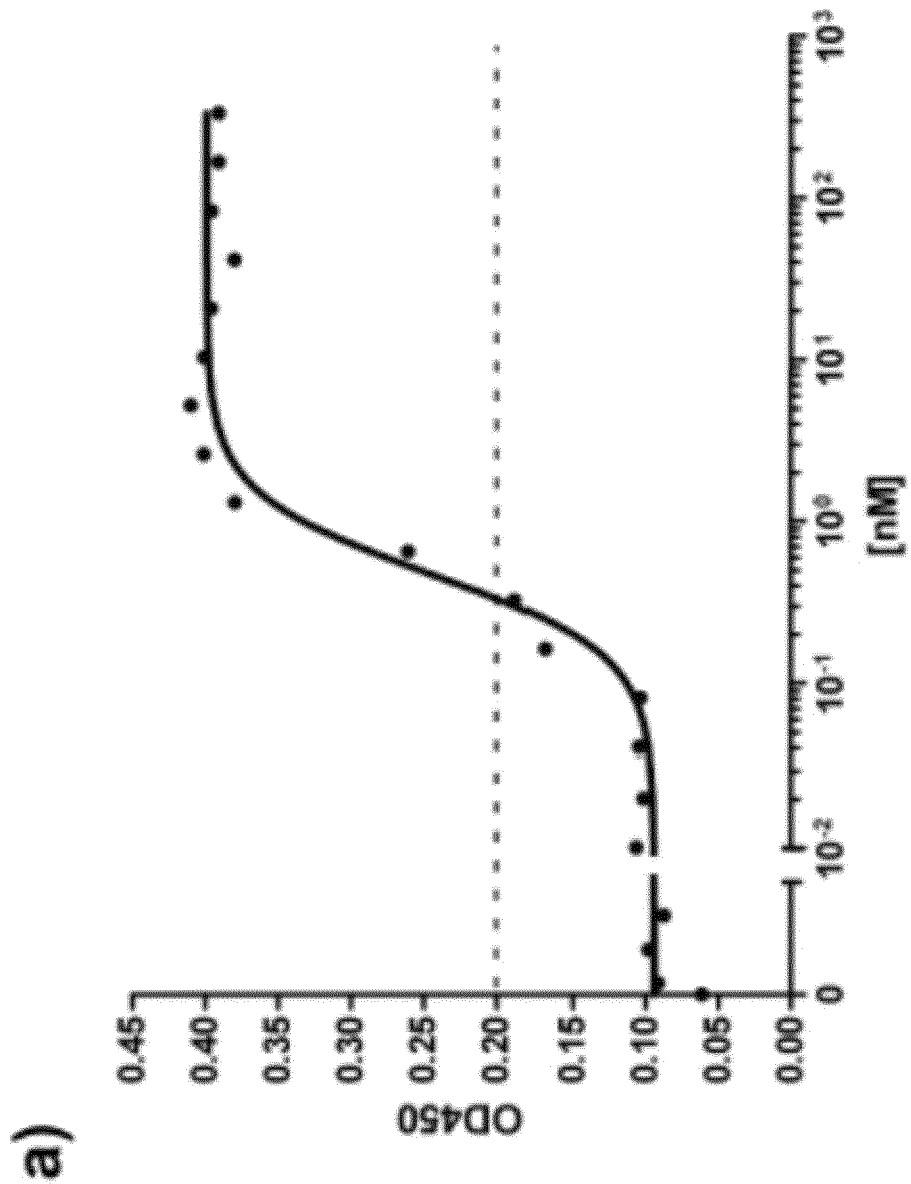
FIG. 3 shows a) ELISA of binding of A5 IgG1 to immobilized recombinant human ENG. b) Flow cytometry analysis of binding of A5-IgG to HT1080 cells.
Figure 3B:
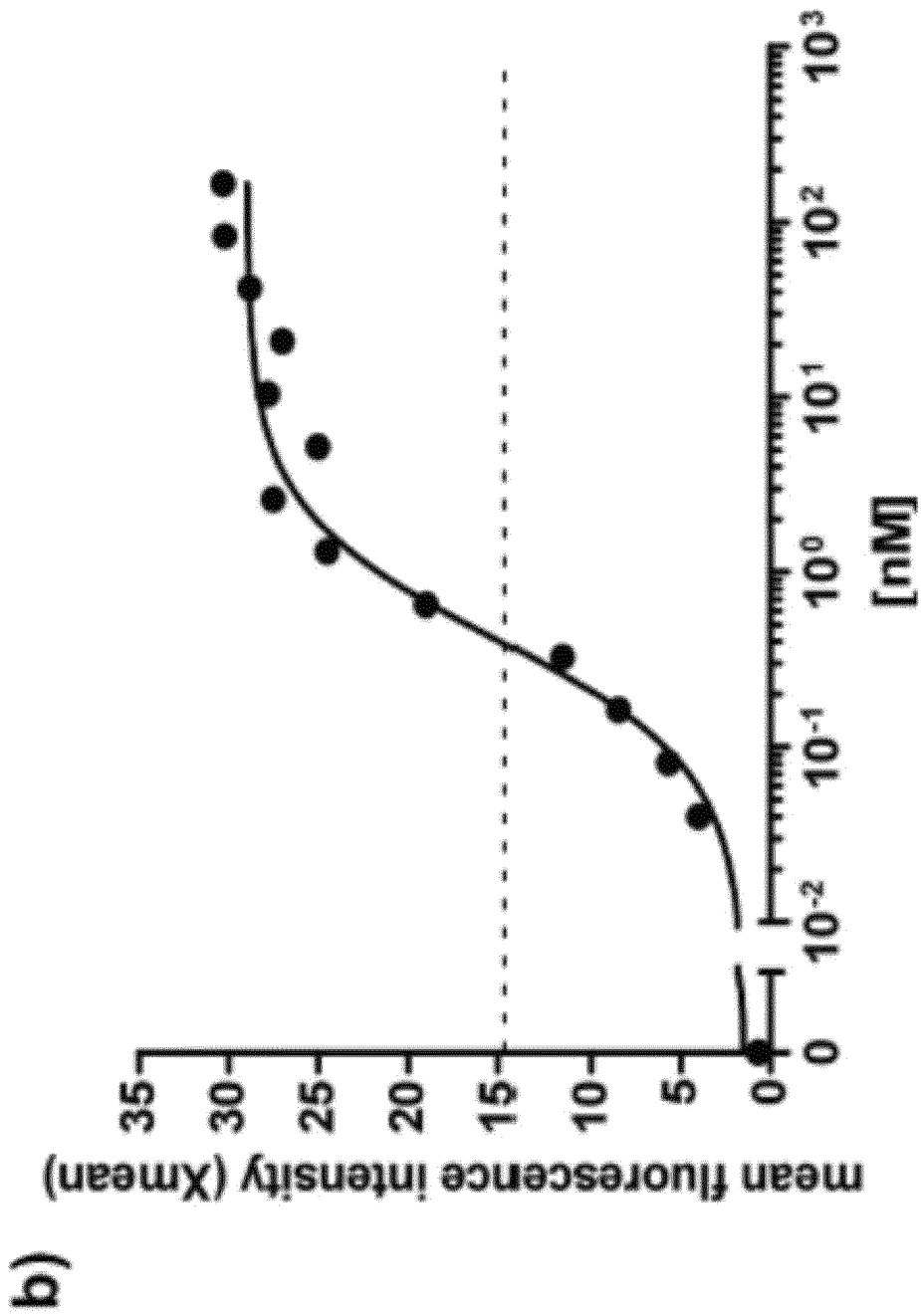
Figure 4:
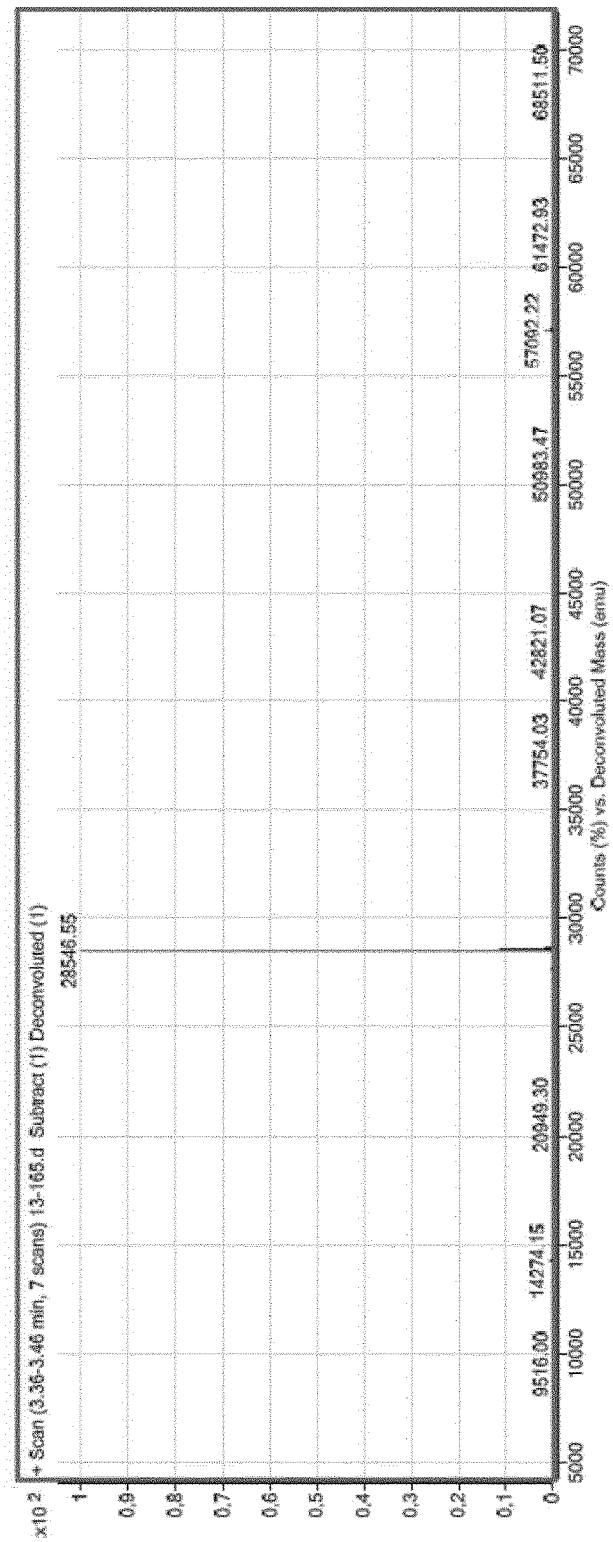
FIG. 4 shows MALDI-Tof profile of recombinant nigrin-b A-chain. Observed mass (Da): 28546.55; Expected mass (Da): 28546.09; Mass deviation: 0.5; Mass Accuracy: 16 ppm.
Figure 5:
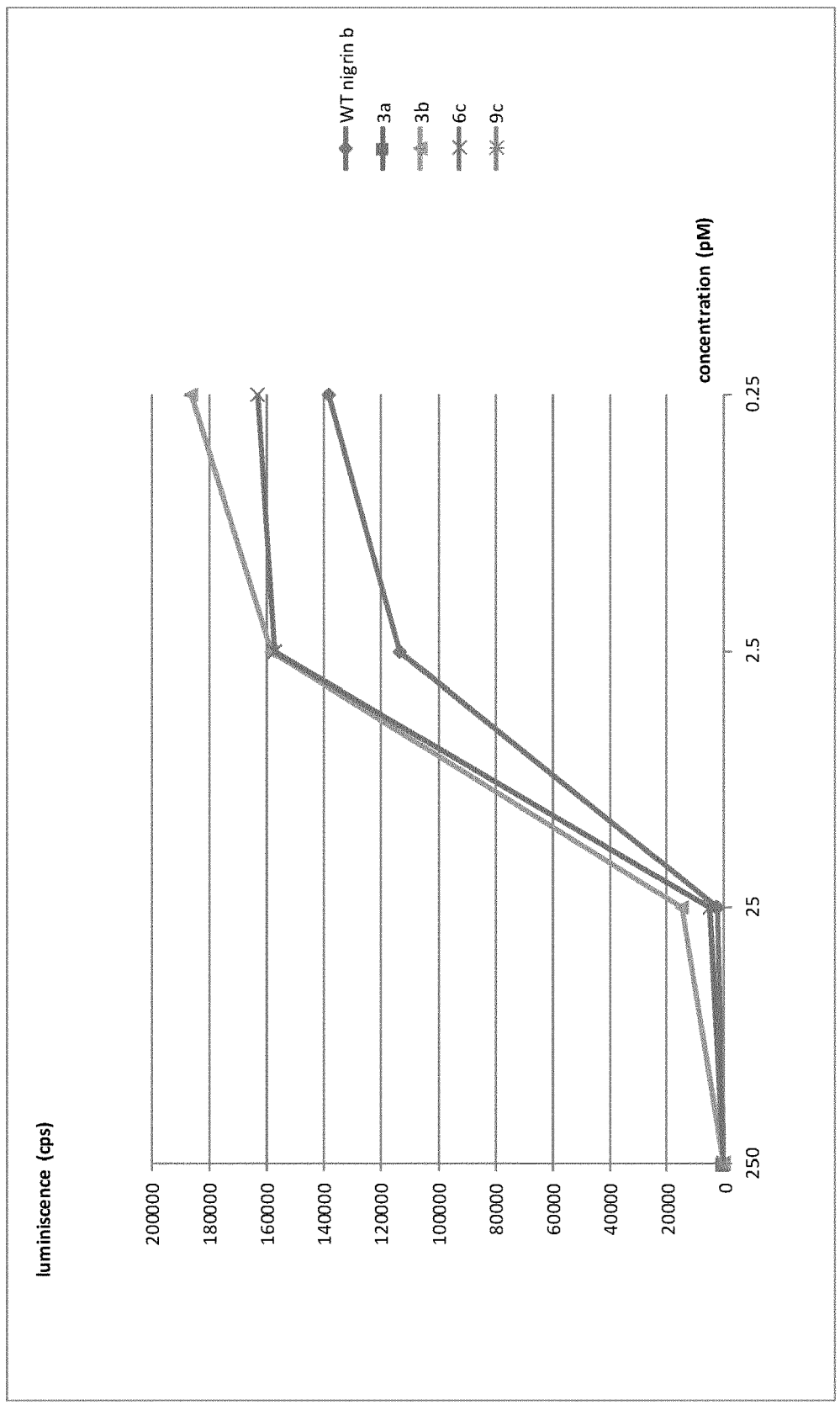
FIG. 5 shows ribosome inactivating protein (RIP) activity of recombinant Nigrin-b A-chain (recNgA) tested in rabbit reticulocyte cell-free lysates (RRL) versus native (WT) Nigrin-b (3a, 3b, 6c, 9c) represent different formulations of recNgA
Figure 6:
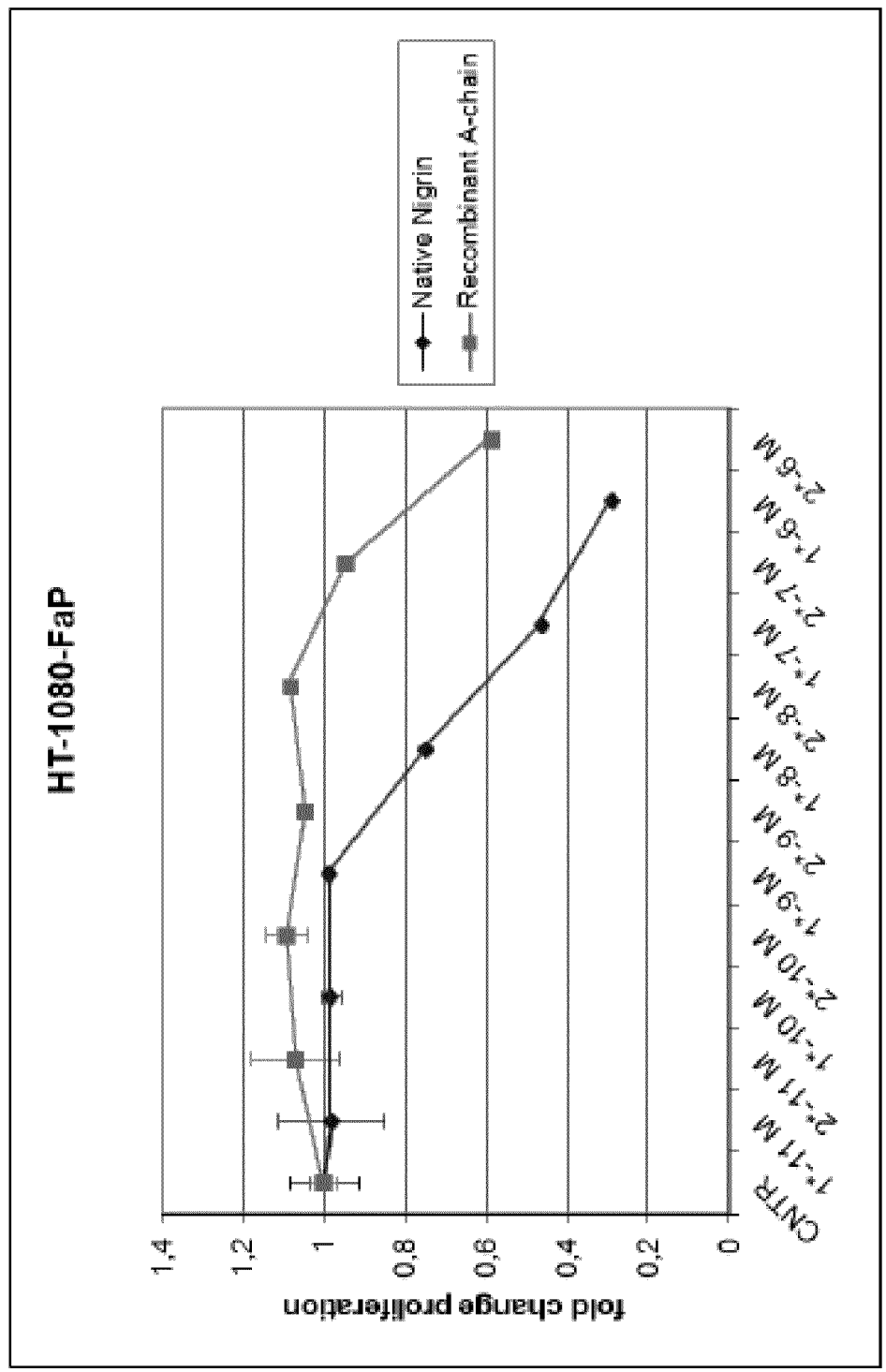
FIG. 6 shows cytotoxicity of recNgA tested on HT1080-FAP cell line through crystal violet viability assay (native Nigrin—diamonds; recombinant Nigrin-b A but not limited to, a cytotoxic chemotherapeutic agent or an anti-angiogenic agent or an immunotherapeutic agent.

Purified anti-muENG mE12 and anti-huENG A5 antibodies were analyzed in ELISA for binding to recombinant ENG and using flow cytometry analysis (FACS). Affinity results are shown for mE12 anti-muENG (FIGS. 1 and 2) and A5 anti-huENG IgG1s (FIG. 3), and are summarized in Table 2. FIG. 1 shows concentration-dependent binding of mE12-IgG to recombinant mouse ENG (aa 27-581), but not to negative control (BSA). FIG. 2 shows flow cytometry analysis of binding of mE12-IgG to a) B16 cells using 50 µg/ml antibody, b) B16 cells using 5 µg/ml antibody, and c) HT1080 cells included as negative control. FIG. 3 demonstrates concentration-dependent binding of A5-IgG to human ENG by a) ELISA and b) flow cytometry analysis.

For scale-up the antibody constructs were cloned in GS double vectors (pEE14.4). The DNA plasmids were transformed, amplified, and transiently transfected into CHOK1SV cells for expression evaluation at a volume of 200 ml. In a second step the antibodies were transiently expressed in 5-10 L large scale cultures. Clarified culture supernatant was purified using one-step Protein A chromatography. Product quality analysis through SE-HPLC, SDS-PAGE and LAL was carried out using purified material at a concentration of 1 mg/ml, alongside an in-house human antibody as a control sample.

The purified protein samples were filtered through a 0.2 µm filter and analysed by SE-HPLC chromatograms. The mE12-IgG was purified to >98.8%. The A5-IgG was purified to >90%. The endotoxin levels were <0.5 EU/mg.

All purified proteins were analyzed by SDS-PAGE in reducing and non-reducing conditions (data not shown).

Purified proteins A5-IgG and mE12-IgG were characterized by SDS-PAGE and size exclusion chromatography. Bioactivity was analyzed by ELISA, using recombinant mouse/human ENG and detection of bound antibodies with HRP-conjugated anti-human IgG antibodies. Cell binding was analyzed by flow cytometry, using ENG-positive HT1080 and ENG expressing mouse eEnd2. Melting points were determined by dynamic light scattering using a zetasizer nano. Affinities were determined by QCM using an Attana A100. Internalization study was performed by indirect immunofluorescence confocal microscopy on permeabilized cells, detecting bound and internalized antibodies with a FITC-labeled secondary antibody.

The full-length IgG1 purified antibodies were successfully produced at both lab scale and large scale, for the generation of immunoconjugates. A summary of antibody properties is shown in Table 2. The antibodies retained their specificity, as shown by ELISA and flow cytometry experiments. Affinities, as determined by QCM, were comparable with that of parental antibodies. QCM measurements indicated the contribution of avidity effects to high-affinity binding. Thermal stability differed between the different IgGs (64-72° C.).

Preliminary internalization studies indicate rapid cellular internalization for A5-IgG against cells expressing human ENG. Indeed within 30 min, almost 90% of the A5-IgG is found within HT1080 cells.

TABLE 2

Summary of antibody properties

| antibody | A5-IgG1 | mE12-IgG1 |
|---|---|---|
| antigen | human endoglin | mouse endoglin |
| isotype | γ1*/κ | γ1*/λ |
| IgG type | human | human |
| plasmid | OCMTX003p | OCMTX004p |
| purity (SEC) | minor aggregates | √ |
| Tm (DLS) | 72° C. | 64° C. |
| EC$_{50}$ ELISA | 0.3 nM (rhENG) | 60 nM (rmENG) |
| EC$_{50}$ FACS | 0.4 nM (HT1080) | 89 nM (eEnd2) |
| binding constants K$_D$ (QCM) | rhENG: K$_D$1 = 260 nM K$_D$2 = 2.5 nM | n.d. |
| internalization | HT1080 30-60 min | n.d. |

γ1* = deficient for ADCC and CDC (see Amour et al., 1999; Richter et al., 2013).

Figure 9:
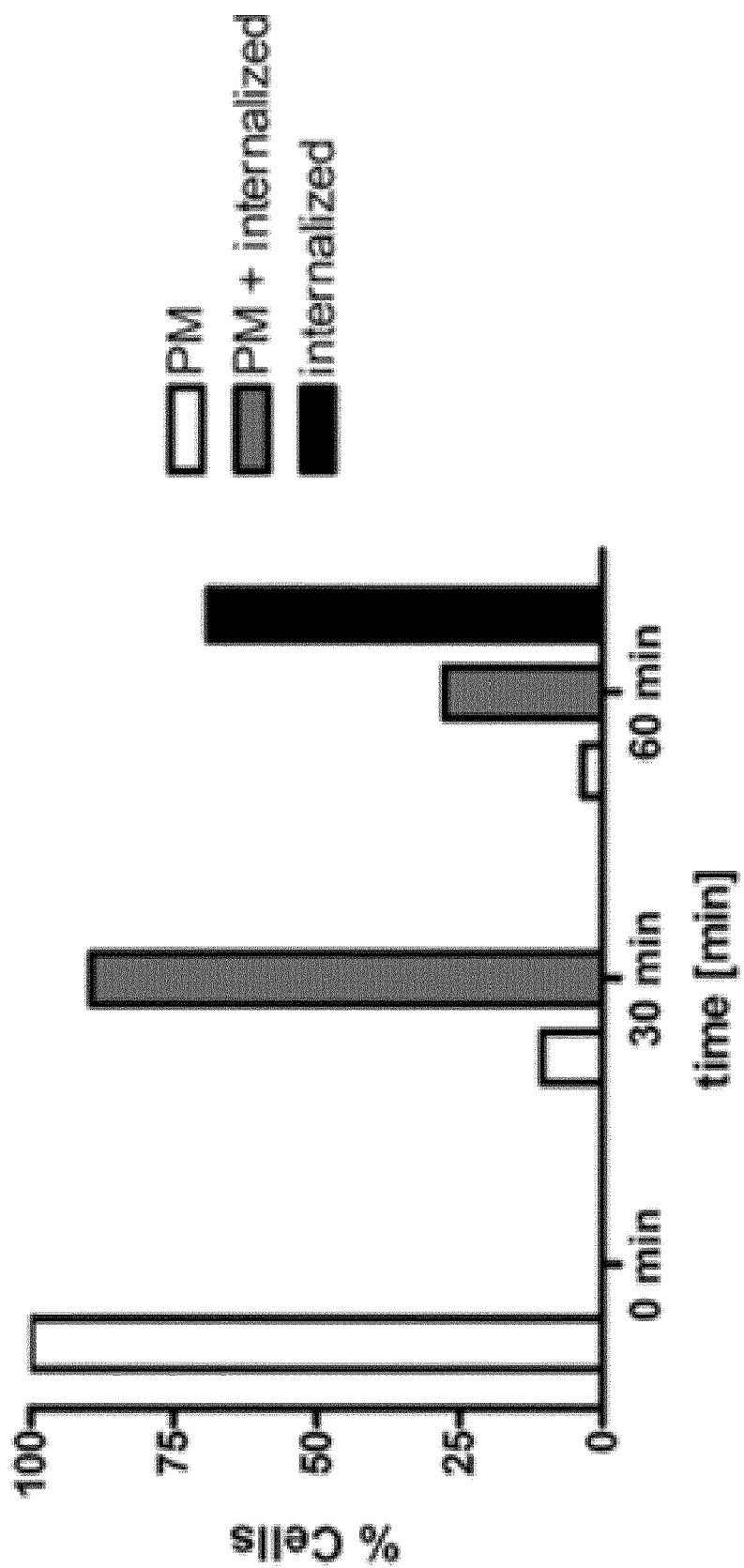

FIG. 9 shows internalization of anti-huENG A5 IgG1.

Example 3—Nigrin-b A-chain

In order to avoid side effects of free toxin that could be released in the bloodstream and to reduce potential immunogenicity of the RIP toxin, as extensively described with ricin, the enzymatic domain of Nigrin b, the A chain, was cloned and expressed in bacteria. The present inventors hypothesized that, if the A chain produced in bacteria was able to retain its activity, it would not be able to enter the cells, unless conjugated to a vehicle molecule, such as an antibody.

Production

Nigrin-b A-chain was synthetized taking into account codon optimization for bacterial expression and the synthetized gene was cloned in two different vectors, Nigrin_pET30b-3 and Nigrin_pET33b-1 (+/− His tag) for expression in two different E. coli strains, E. coli BLR(DE3) and E. coli HMS174(DE3). Different culture media were used to check different expression conditions. Process purification was established using Capto Q chromatography and SP Sepharose High Performance. Purified recombinant Nigrin-b A-chain (recNgA) was formulated at 5 mg/ml in PBS 1× pH7.4, DTT 0.5 mM, glycerol 10%. Endotoxin levels were <1 EU/mg of Nigrin and the purity >99% in monomeric form.

Eldman N-terminal sequencing revealed that N-terminal end of recNgA corresponded to the expected sequence.

```
Recombinant Nigrin-b A-chain amino acid sequence:
                                          (SEQ ID NO: 25)
MIDYPSVSFNLDGAKSATYRDFLSNLRKTVATGTYEVNGLPVLRRESEVQ

VKSRFVLVPLTNYNGNTVTLAVDVTNLYVVAFSGNANSYFFKDATEVQKS

NLFVGTKQNTLSFTGNYDNLETAANTRRESIELGPSPLDGAITSLYHGDS

VARSLLVVIQMVSEAARFRYIEQEVRRSLQQATSFTPNALMLSMENNWSS
```

-continued
MSLEIQQAGNNVSPFFGTVQLLNYDHTHRLVDNFEELYKITGIAILLFRC

SSPSND

The recombinant Nigrin-b A-chain has the following characteristics: Number of amino acids: 256
Molecular weight: 28546.0
Theoretical pI: 5.45
The nucleotide sequence encoding recombinant Nigrin-b A-chain is as follows:

(SEQ ID NO: 26)

```
atagactatc cctccgtctc cttcaacttg gatggagcca
agtcggctac atacagggac ttcctcagca acctgcgaaa
aacagtggca actggcacct atgaagtaaa cggtttacca
gtactgaggc gcgaaagtga agtacaggtc aagagtcggt
tcgttctcgt ccctctcacc aattacaatg gaaacaccgt
cacgttggca gtagatgtga ccaaccttta cgtggtggct
tttagtggaa atgcaaactc ctactttttc aaggacgcta
cggaagttca aaagagtaat ttattcgttg gcaccaagca
aaatacgtta tccttcacgg gtaattatga caaccttgag
actgcggcga atactaggag ggagtctatc gaactgggac
ccagtccgct agatggagcc attacaagtt tgtatcatgg
tgatagcgta gcccgatctc tccttgtggt aattcagatg
gtctcggaag cggcaaggtt cagatacatt gagcaagaag
tgcgccgaag cctacagcag gctacaagct tcacaccaaa
tgctttgatg ctgagcatgg agaacaactg gtcgtctatg
tccttggaga tccagcaggc gggaaataat gtatcaccct
tctttgggac cgttcagctt ctaaattacg atcacactca
ccgcctagtt gacaactttg aggaactcta taagattacg
gggatagcaa ttcttctctt ccgttgctcc tcaccaagca
atgat
```

Materials

- Nigrin_pET30b-3 genetic construct.
- *Escherichia coli* (Migula) Castellani and Palmers BLR (DE3)
- Culture media: auto induced medium (AIM)
- Extraction culture buffer: Glycine/NaOH 10 mM, Leupeptine 1 μg/ml, Pepstatine 1 μg/ml, pH 9.5.
- Extraction supernatant buffer Tris-HCl 50 mM, NaCl 200 mM, $MgCl_2$ 2 mM, leupeptine 1 $\mu g ml^{-1}$, pepstatine 1 $\mu g ml^{-1}$, lysozyme 0.1 $mg ml^{-1}$, pH8.0.
- Dialysis solution: Citric acid/NaOH 25 mM pH5.0. -Capto Q FPLC: Equilibration buffer A: Glycine/NaOH 50 mM pH9.5. Elution buffer B: Glycine/NaOH 50 mM pH9.5, NaCl 1 M.
- Pooled fractions from Capto Q step (+80 ml extraction).
- SP Sepharose HP FPLC: Equilibration buffer A: Citric acid 25 mM pH4.0. Elution buffer B: Citric acid 25 mM pH4.0, NaCl 1 M.

Methods

*E. coli* BLR(DE3) holding expression Nigrin_pET30b-3 cultivated in 1 L format of Auto Inducible Medium (AIM) with 30 $\mu g ml^{-1}$ Kanamycin. Protein expression was triggered by lactose activation and glucose depletion after about 3-4 hours of growth. Then, the temperature was lowered to 20° C. for an overnight duration.

For extraction, each cell pellet was initially resuspended in 80 ml of extraction buffer per liter of culture, and 3 cycles of 7 minutes disintegration at 1100-110 Bar were performed after 30 minutes of incubation at 8° C. under shaking. Then the extract underwent 60 minutes centrifugation at 15,900 g, 8° C. The supernatant was the purification's starting material.

Capto Q FPLC: 160 ml of extracted product from 81 culture were loaded into 160 ml Capto Q and equilibrated using 4 CV of equilibration buffer and washed with 15 CV of equilibration buffer. Elution was carried in three steps: 15 CV at 1.5 mS/cm (7.6% B); 20 CV at 23.8 mS/cm (18.9% B); 20 CV 100% B.

Dialysis was performed at the following conditions: 650 ml of the product were dialyzed in 4×5 L baths in citric acid/NaOH 25 mM pH5.0, cut-off 6-8000 Da. Dialysis factor 3500, <24 h. After dialysis, a 30 minutes centrifugation at 20,500 g and 8° C. allowed to separate soluble from insoluble fractions. SDS-PAGE was performed on the total and soluble fractions both pre and post dialysis (10 μl loaded on SDS-PAGE). The eluent was dialysed into PBS pH7.4 and filtered φ=0.22 μm using 2×20 $cm^2$ EKV filters.

SP Sepharose HP: 610 ml of dialyzed pool of Capto Q in Citric acid 25 mM pH5.0 were loaded into 240 ml SP Sepharose High Performance with 4 CV of equilibration buffer and washed with 15 CV of equilibration buffer and eluted at 25 Cv gradient to 20% B; 4 CV step of 100% B.

Pooled fractions from SP Sepharose HP step were dialysed in PBS pH7.4, DTT 0.5 mM (5×4 L baths, pooled fractions of 950 mL at 0.97 mg/ml). Cut off was 6-8000 Da, dialysis factor was ~3130, time >24 h. Afterwards a 30 min centrifugation at 20.55 g and 8° C. allowed to separate soluble from insoluble fractions. 10% glycerol was added afterwards.

Finally the eluent was dialysed into PBS pH7.4 (5 baths ~3100) and filtered φ=0.2 μm, then the recNg b A batch was snap frozen at −80° C. A SEC in Semi-Preparative S200 Superdex was later carried out.

Size exclusion chromatography and mass spectrometry analysis demonstrated monomeric and purification status of the obtained recombinant nigrin-b A-chain (recNgA) (FIG. 4).

Stability studies were performed to evaluate pH and temperature effect on nigrin-b A-chain protein itself and its activity. recNgA is stable at pH ranging from 5 to 9, and in presence or not of glycerol (from 10 to 45%) (data not shown).

Activity

The ribosome-inactivating protein (RIP) activity of recombinant Nigrin-b A-chain was tested in rabbit reticulocyte cell-free lysates: $IC_{50}$ value obtained was similar to native nigrin-b and within 2.5 to 25 pM range (see FIG. 5). Thus, the A chain from Nigrin-b, expressed as a recombinant protein in bacteria, maintains its enzymatic activity, supporting that glycosylation is not required for RIP activity of Nigrin-b A-chain.

RecNgA retains its activity in rabbit reticulocyte cell-free lysates if stored frozen at (−80° C.) and below 3 freeze-thaw cycles (not shown).

The cytotoxic activity of recNgA was tested on cell cultures through crystal violet-based viability assay. recNgA, lacking the B chain to translocate within cells, presents a 100 to 1000 less toxic activity than native Nigrin-b, as shown in FIG. 6. Native nigrin b showed an $IC_{50} \approx 2 \times 10^{-8}$ M (similar to previous published data see 37), while recNgA showed an $IC_{50} \approx 2 \times 10^{-6}$ M.

Previously published studies showed that native Nigrin b presents higher RIP activity than Ricin in RRL assay, while it is much less toxic (30-10,000 time, approximately) in cells or in vivo (see $IC_{50}$ and $LD_{50}$ values in Table 3).

Upon removing of B chain, Ricin A chain loses activity in both RRL assay and cytotoxicity assay. Unexpectedly, Nigrin b A chain, generated for the first time in this present invention, only loses activity in cell cytotoxicity assay, while it was even increased in RRL assay with respect to native Nigrin b. These data were suggesting that, in the case of Ricin, removing B chain was affecting not only binding and translocation of A chain, but also its RIP activity, while this was not the case for Nigrin b A chain that retains and even increases its RRL activity with respect to its native counterpart. As a result, Nigrin b A chain is 50 times more active than Ricin A chain in RRL.

Consequently, upon conjugation, Nigrin b A chain conjugates present higher cytotoxic activity ($IC_{50}$ within pM range) than Ricin A chain conjugates (nM range)(not shown).

TABLE 3

In vitro and in vivo activity data for Ricin and Nigrin b (native and A chain).

| | Rabbit Lysate $IC_{50}$ (pM) | HeLa Cells $IC_{50}$ (pM) | Mouse $LD_{50}$ (μgkg$^{-1}$) |
|---|---|---|---|
| Nigrin b | 30 | 27,600.00 (20-2300 nM; dpt cell line) | 12,000.00 |
| Nigrin b A chain | 6.5 | 750, 000.00 (HT1080-FAP) 300, 000.00 (HT1080) | ND |
| Ricin | 100 | 0.67 | 3.00 |
| Ricin A chain | 300 | 260,000.00 (T cells) | ND |

(Inventors' own data Nigrin b A chain; see also Ferreras J. M. et al., Toxins, 3:420, 2011; Svinth M. et al., BBRC, 249: 637, 1998)

Example 4—Conjugation of Nigrin-b A-Chain to Anti-ENG Antibodies

For immunoconjugates containing RIPs to exhibit maximal cytotoxicity the RIP must be released from the targeting vehicle in fully active form, which requires avoiding steric hindrance (38). The disulfide bond is the only type of linkage that fit this criterium (39, 40). This bond allows conjugation using reagents for the introduction of free sulfhydryl groups such as N-succynimidyl 3(2-pyridyl-dithiopropionate) (SPDP) and 4-succynimidyloxycarbonyl-α-methyl-α (2-pyridyl-dithio)toluene (SMPT). Immunotoxins consisting of mAbs covalently bound to toxins by hindered disulfide linkers, often labeled as second generation immunotoxins, are stable, long lived and display potent cytotoxicity to target cells (41).

SPDP has already been used in the making of immunotoxins (ITs) containing nigrin b (36, 42). Moreover SMPT protects the disulfide bond from attack by thiolate anions, improving in vivo stability of the linkage (43, 44).

Material

Recombinant nigrin b A chain in PBS, pH7.4, 10% glycerol, 0.5 mM DTT, 4.92 gl$^{-1}$, stored at 5° C.

5,5'-dithio-bis-(2-nitrobenzoic acid)

GE PD MiniTrap G-10 desalting columns.

0.2 μm 28 mm sterile Minisart filters.

Sciclone ALH 3000 workstation.

Sarstedt Microtest Plate 96-Well Flat Bottom, ref no 82.1581.

Methods

Dithiothreitol (DTT, Cleland's reagent) is a redox agent that will be used to free the thiol groups present in the protein sample. Once said groups have been freed and so are available for reacting 5,5'-dithio-bis-(2-nitrobenzoic acid) (Ellman reagent) will be added. Ellman reagent disulphide bridge will be cleaved and the 2 resulting thio-nitrobenzoate molecules (TNB) will attach to the protein at the thiol group sites. To titrate the TNBs absorbance values will be taken at λ=412 nm, a wavelength at which DTT is not absorbed, rendering the concentration of thiol groups. The proportion of these with the concentration of the protein taken from its absorbance at λ=280 will yield the number of free thiol groups per protein molecule.

Direct thiol titration was performed as follows:

204 μl recNg b A were dissolved in 796 μl 20 mM phosphate 250 mM NaCl 1 mM EDTA pH 7.0 (assay buffer) (1.0033 gl$^{-1}$=final concentration). Ellman reagent was dissolved in phosphate 0.2 M at 3 gl$^{-1}$. For both buffers monobasic and dibasic sodium phosphate were added in a 1.61 to 1 mass proportion. PH was adjusted at room temperature and buffers were filtered. 100 ml Ellman buffer and 500 ml assay buffer were prepared. Ellman reagent was completely resuspended rather than weighed.

The recNgA sample was incubated in the presence of 4.8 mM DTT at room temperature for 30 min. The recNgbA sample was then purified in the column and the first 10 ml of the eluent aliquoted (V=0.5 ml).

The $A_{280}$ of the aliquots was taken and the two most concentrated mixed. $A_{280}$ was taken again. 10 μl of 3 gl$^{-1}$ DTNB were added and $A_{412}$ measured after 2 min (n=1), using Ellman diluted in assay buffer in the same concentration as a blank ($n_b$=3). Readings belonged to the 0.1-3 AU linear range. Protein solutions were pipetted right beneath the meniscus after vortexing. 100 μl were pipetted per well.

The results of this study show that the thiol group belonging to recNgA's single cysteine residue is free and available for reaction, not being blocked by its tertiary structure. This will allow recNgbA to be conjugated using a linker that requires a hindered inter-chain disulfide bond.

It is well established that immunoconjugates which contain ribosome-inactivating proteins exhibit maximal cytotoxicity only when the toxin molecule is released from the targeting vehicle in a fully active form. The separation of the RIP molecule from the carrier is required to avoid steric hindrance and to allow an effective translocation of the toxin into the cytoplasm (38). At present, the disulfide bond is the only type of linkage which appears to fit these criteria (40).

The coupling of two different protein macromolecules, that results in heterodimer formation, requires that each protein is modified prior to mixing them to react. In the case of the A chains of type 2 RIPs, the modification is limited to the reductive cleavage of the native cysteine residue that links the active (A) and the binding (B) chains of the molecule.

For IgG molecules, this is not possible because cysteine residues are involved in maintaining the tertiary and/or quaternary structure of the protein, so that it is not possible to reduce them without loss of the specific protein functions. Moreover, presumably some of the cysteine residues are not sterically accessible, as it was demonstrated by the 10 thiols groups per immunoglobulin that had to be generated for an optimal conjugation to an activated RIP (45).

For these reasons, in most IgG molecules, thiol groups are chemically inserted using hetero-bifunctional reagents, and several methods have been developed in order to generate hetero-conjugates avoiding or reducing to a minimum the formation of homopolymers. In most cases, the reagents used to introduce thiol groups react with amino groups, forming amide or amidine bonds. Amino groups are reactive, abundant and, in a limited way for most proteins, expendable. That is, a limited number of amino groups can be modified without diminishing the biological activity of the protein (40).

The most commonly used reagents for the introduction of free sulphydryl groups are N-succynimidyl 3-(2-pyridyl-dithiopropionate) (SPDP) and 4-succynimidyloxycarbonyl-α-methyl-α-(2-pyridyl-dithio)toluene (SMPT), that introduce 2-pyridyl disulphide groups into the protein by reacting with amino groups to form neutral amides, and methyl 4-mercaptobutyrimidate (2-iminothiolane.Traut's reagent) that introduces mercaptobutyrimidoyl groups, reacting to form charged amidines, thus preserving the positive charge of the derivatized amino acid (40;44).

SPDP and SMPT introduce hindered disulphide bond, while 2-iminothiolane —SH must be protected by reacting it with 5,5'-dithiobis-2-nitrobenzoic acid (Ellman's reagent).

The reaction with Ellman's reagent is also used for the quick measurement of protein sulphydryl groups (45, 46).

SMPT has a methyl group and a benzene ring attached to the carbon atom adjacent to disulphide bond that protects it from attack by thiolate anions, thus improving the in vivo stability of the linkage (43, 44).

Based on these data, IgG proteins can be modified with SMPT, which do not significantly affect the antigen binding property of the molecules in the following conditions, even if they change the charge of the protein in the reaction site.

In one study the present inventors investigated conjugating IgG1s with recNgA, using 2 different recNgA:mAb molar ratio of 2.5 and 3.5, after derivatization using an SMPT:mAb molar ratio of 6, following conjugation protocols (see 40). Purification was performed by Size Exclusion chromatography on Sephacryl S200 (see 41).

Under the described conditions, the immunotoxin is predominantly a mixture of antibody linked to one or two toxin molecules, with the presence of high molecular weight components (IgG linked to several RIP proteins), as well as free and polymeric RIPs (dimeric in the case of recNgA) and free antibody. Thus, a careful purification is thought to be desirable to obtain a pure product.

In Vitro Activity Testing

Figure 7:
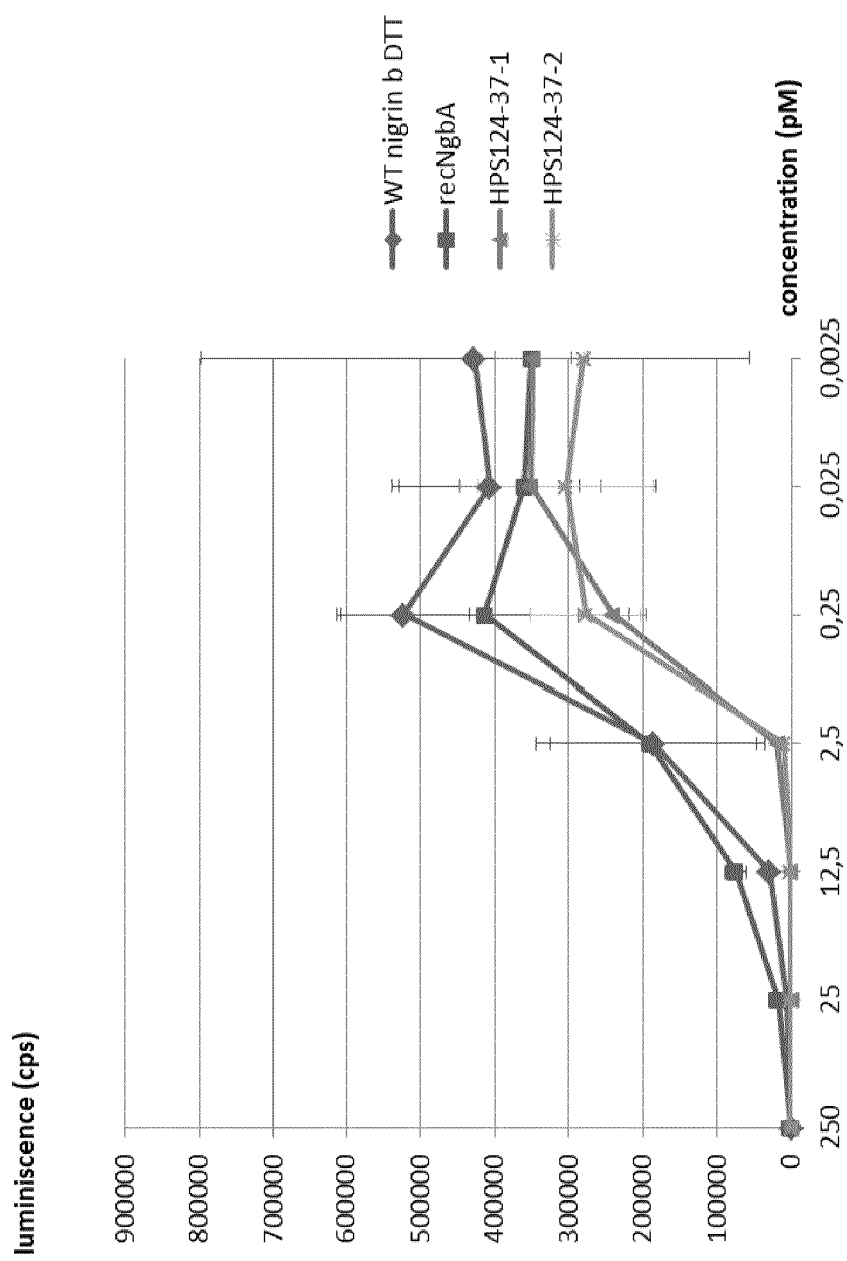

Activity testing on conjugates prepared as described above was performed though evaluation of RIP activity in rabbit reticulocyte cell-free lysate (RRL) assay. Results are presented in FIG. 7.

$IC_{50}$ values obtained for the native Nigrin-b or recNgA were in the 2.5 pM range and those for conjugates were similar and within 1-0.5 pM range, even higher than native Nigrin-b positive control, showing that antibody conjugation did not affect the enzymatic activity of recNgA.

Example 5—Conjugation of Cytolysins to Anti-ENG Antibodies

The cytolysins employed for conjugation studies were chosen from the general structure shown above (formula IV). These structures exhibit activity against different cancer cell lines (nM to pM range).

Various linker systems can be used and attached to either $R^2$ or $R^{17}$ position of the molecule.

Figure 8:
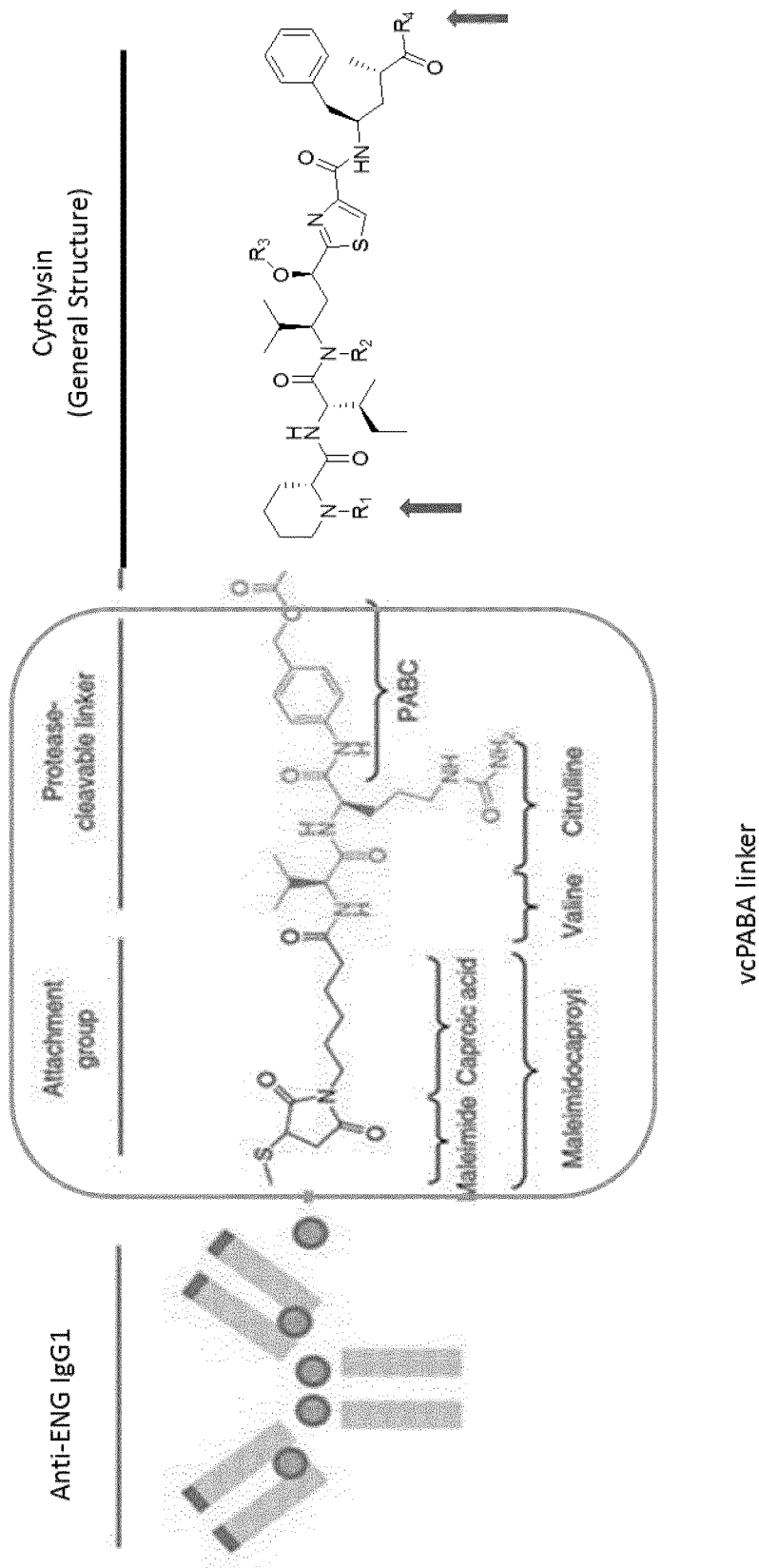

The general outline of the cytolysin conjugates, including the vcPABA linker and anti-ENG antibody, is shown in FIG. 8 (in the structure depicted in FIG. 8, the attachment site of the cytolysin to the vcPABA linker is at position $R_1$ or $R_4$—the $R_1$ and $R_4$ numbering system used in FIG. 11 differs from the R group numbering system used, e.g., in the claims; it is intended that $R_1$ of FIG. 11 corresponds to $R^2$ in the claims and that $R_4$ of FIG. 11 corresponds to $R^{17}$ of the claims).

The vcPABA (valine-citrulline-PABC) protease-cleavable linker has been previously used in the ADC molecule Brentuximab Vedotine, developed by Seattle Genetics and Takeda, and recently approved by the FDA and EMEA as Adcetris® (2011, and November 2012, respectively). In this ADC the vcPABA has been coupled at its free NH2 to maleimide caproyl for thiol-based conjugation on mAb (cAC10 anti-CD30 antibody). On the other side, vcPABA has been conjugated through its COOH to the Auristatin cytotoxic drug from Seattle Genetics (MMAE). (see 48)

The present inventors have used this linker (maleimide caproyl-vcPABA) to conjugate anti-ENG antibodies through thiol-based reaction with the maleimide caproyl, and on the other end, to the cytolysin cytotoxic molecules through its cyclic piperidine with vcPABA ($R_1$ or $R_4$ positions of the cytolysin shown in FIG. 8).

Synthesis of Maleimido-Val-Cit-PABOCO-Tubulysin/Cytolysin-TAM461:

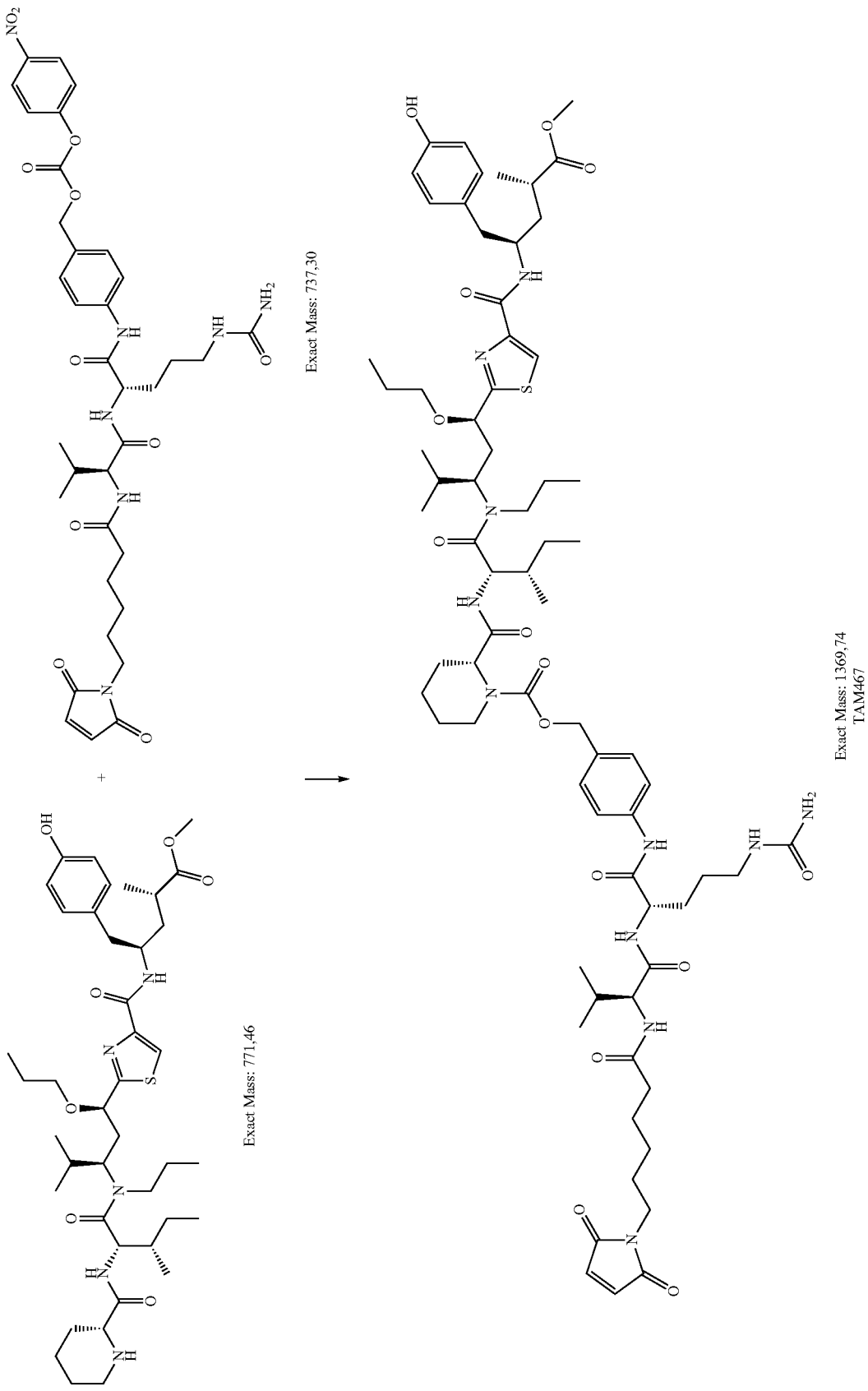

TAM461 (Tubulysin/Cytolysin): 30.0 mg (0.041 mmol)
DMF: 3 mL
TAM465 (Linker): 35 mg (0.045 mmol)
HOBt: 1.4 mg
DIPEA: 10 μL TAM461 and TAM465 were dissolved in anhydrous DMF under dry conditions and the resulting solution was treated with HOBt and DIPEA. The reaction was stirred at RT for 18 h. The reaction mixture was concentrated and the resulting oil was purified by column chromatography using 2-6% methanol: DCM to give 35 mg (64%) of TAM467 as a white solid. ESI-MS: m/z=1371 [M+H].

Synthesis of Maleimido-Val-Cit-PABOCO-Tubulysin/Cytolysin-TAM470:

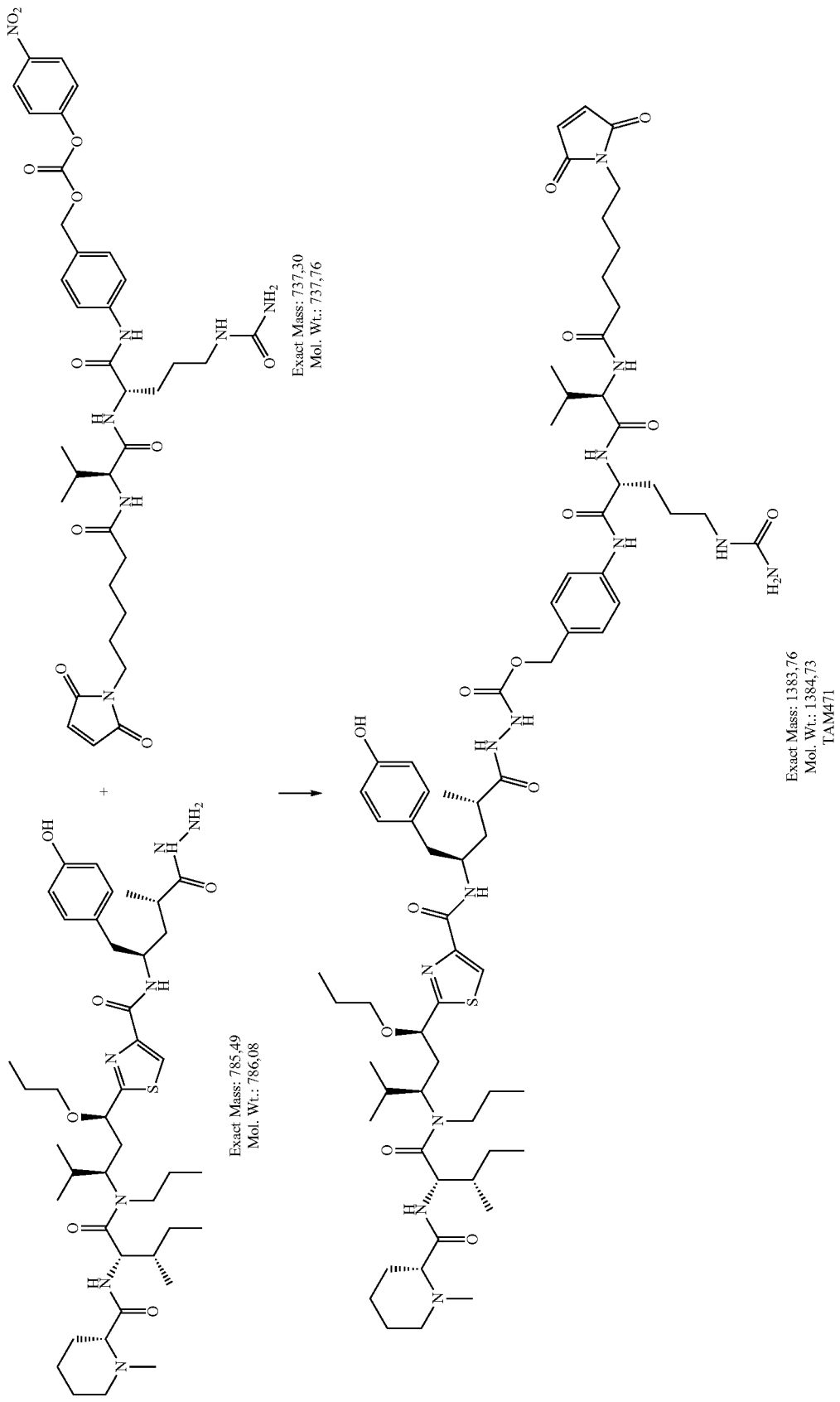

TAM470 (Tubulysin/Cytolysin): 0.07 mmol
DMF: 5 mL
TAM466 (Linker): 50 mg (0.065 mmol)
HOBt: 2.4 mg
DIPEA: 18 μL TAM470 and TAM466 were dissolved in anhydrous DMF under dry conditions and the resulting solution was treated with HOBt and DIPEA. The reaction was stirred at RT for 18 h and then analysed with TLC, indicating completion of reaction, The reaction mixture was concentrated and the resulting oil was purified with column chromatography using 4-12% methanol: DCM to give 56 mg of TAM471 (yield: 62%). ESI-MS: 1384.6 [M+1].

In vitro activity testing is performed. Functional activity is evaluated through microtubule inhibition assay, while cytotoxic activity is determined through crystal violet viability assay.

Generation of Cytolysin-Linker Derivatives

Different cytolysin-linker derivatives were synthesized according to the general structure presented in FIG. 11, where vcPABA linker was added either in position R1 (TAM467, TAM551) or R4 (TAM471, TAM553, TAM558), alone or with ethylene-glycol spacer (EG; n=1 to 3), or substituted by ethylene glycol groups (n=3) (TAM552). The respective chemical structures are presented in Table 4.

TABLE 4
Chemical structure of cytolysin-linker derivatives
| Product | Code | Mol. Wt. |
|---|---|---|
| 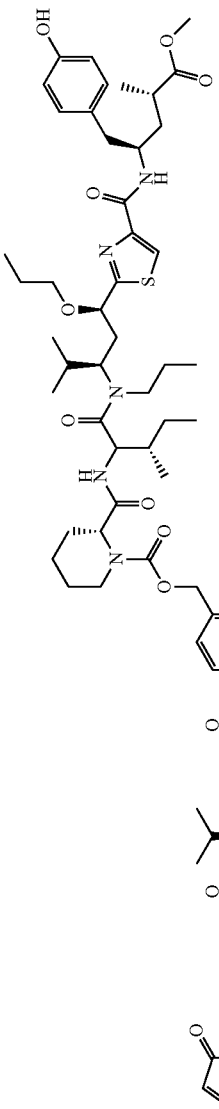 | TAM467 | 1370.7 |
| 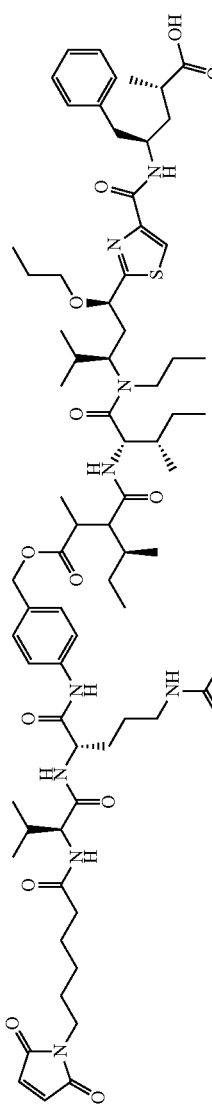 | TAM551 | 1356.7 |
| 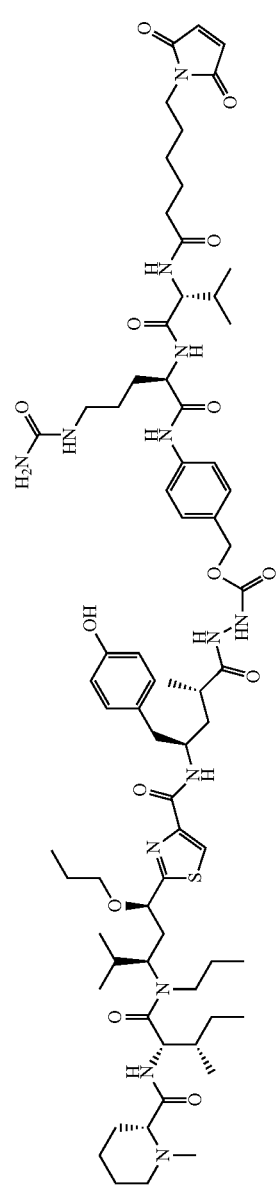 | TAM471 | 1384.7 |

TABLE 4-continued
Chemical structure of cytolysin-linker derivatives
| Product | Code | Mol. Wt. |
|---|---|---|
| 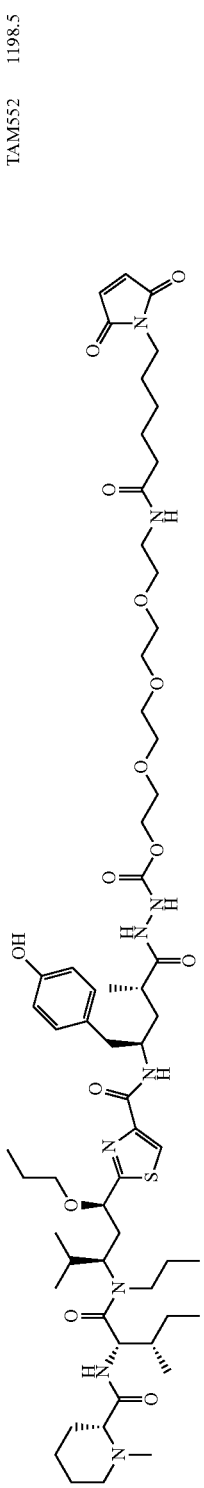 | TAM552 | 1198.5 |
| 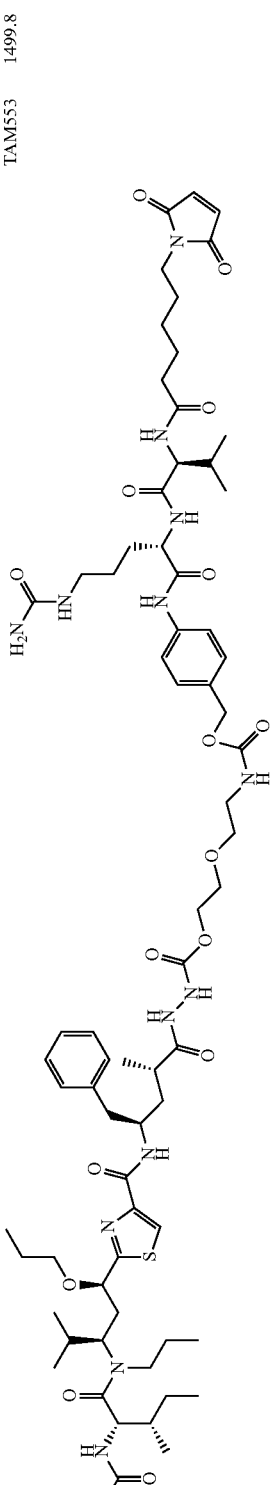 | TAM553 | 1499.8 |
| 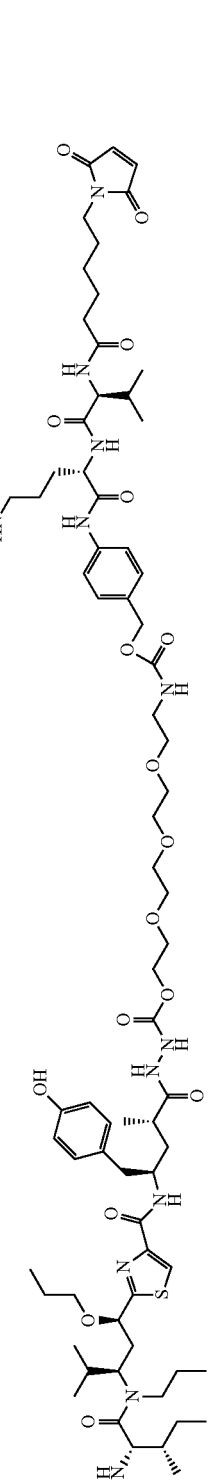 | TAM558 | 1603.9 |

Microtubule inhibition activity and cytotoxic activity of each new derivative were evaluated through tubulin polymerization inhibition assay (TPI; Tubulin Polymerization assay kit; Cytoskeleton, Cat. #BKO11P), and cell proliferation arrest on HT1080 cells (CPA; crystal violet). IC50 were calculated and results are presented in Table 5.

TABLE 5

Microtubule inhibition activity and Cell Cytotoxicity activity of cytolysin-linker derivatives.

| Compound | IC50 (TPI assay; µM) | IC50 (CPA assay; nM) |
|---|---|---|
| TAM467 (Linker in R1) | 150 | 230-420 |
| TAM551 (Linker in R1) | ND | 90 |
| TAM471 (Linker in R4; vcPABA) | 14 | 17-42 |
| TAM552 (Linker in R4; no vcPABA; 3EG) | 1.9 | 10 |
| TAM553 (Linker in R4; vcPABA; 1EG) | 6 | 98 |

TABLE 5-continued

Microtubule inhibition activity and Cell Cytotoxicity activity of cytolysin-linker derivatives.

| Compound | IC50 (TPI assay; µM) | IC50 (CPA assay; nM) |
|---|---|---|
| TAM558 (Linker in R4; vcPABA; 3EG) | 1.9 | 98 |
| TAM334 (parental cytolysin; no linker) | 2 | 0.3-0.6 |
| Tubulysin A | ND | 0.04-0.2 |
| Tubulysin A + linker | ND | 5-20 |
| MMAE (Seattle Genetics) | ND | 0.1-0.6 |
| DM1-DM4 (Immunogen) | ND | 0.01-0.1 |

(ND: Not determined)

In vitro activity of parental cytolysin TAM334 is within the same range of other payloads currently used for the generation of antibody-drug conjugates such as auristatins (MMAE) or maytansinoids (DM1-DM4). As expected and previously described for other compounds from the Tubulysin A family, upon addition of linker, cell cytotoxic activity of cytolysins was decreased with respect to the parental compound TAM334. In addition, TAM467 derivative was presenting significantly lowest activity in both assays. All the derivatives were used in conjugation to generate ADC molecules and were evaluated comparatively both in vitro and in vivo to select the most active cytolysin-linker derivative.

Conjugation and Chemical Characterization of ADCs

Each of the newly generated derivatives was conjugated to monoclonal IgG1 human antibodies following a non-site-specific conjugation method on cysteine residues. To this aim, one batch of antibody was reduced and reacted with each of the derivatives. Different TCEP ratios were tested to reach optimal DAR of 3-4, less than 10% of free antibody and drug. Optimal conjugation conditions were as followed: TCEP=2.5 and 3.57 Thiol levels Ellmann's. Conjugates were then purified on G25 Sephadex and analysed through Size Exclusion Chromatography (SEC) to determine their purity, as well as Hydrophobic Interaction Chromatography (HIC) and Polymeric liquid reversed-phase chromatography (PLRP) to determine DAR, content of free antibody and distribution profile of different ADC species (0-8 drugs/mAb). Content of free drug was evaluated by UV detection method at 280 nm. Results of chemical analysis were determined (not shown) and biochemical characteristics of ADCs are shown in Table 6.

TABLE 6

Summary of chemical characteristics of the different ADC molecules

| Lot | Drug | mAb Conc. | HIC free mAb | DAR | SEC purity 280 nm | Free Drug | Volume |
|---|---|---|---|---|---|---|---|
| HPS157-039-001 | TAM471 | 1.195 mg/mL | 10.1% | 3.38 | 92% | 0% | ~5.8 mL (6.931 mg) |
| HPS157-039-002 | TAM551 | 1.332 mg/mL | 22.4% | 3.08 | 74% | 0% | ~5.8 mL (7.726 mg) |
| HPS157-039-003 | TAM552 | 1.319 mg/mL | 5.1% | 3.84 | 97% | 0% | ~5.8 mL (7.650 mg) |
| HPS157-039-004 | TAM553 | 1.305 mg/mL | 7.0% | 4.10 | 84% | 0% | ~5.8 mL (7.569 mg) |
| HPS157-039-005 | TAM558 | 1.332 mg/mL | 5.8% | 3.92 | 93% | 0% | ~5.8 mL (7.726 mg) |

The various drugs produced different levels of aggregation. Specifically ADC HPS157-039-002 (TAM551) showed highest level of aggregation already at DAR=3.08, leaving 22.4% of unconjugated antibody. A preliminary conjugation with TAM467 also showed high level of aggregation: at DAR 3.27, SEC purity was already only 67% with 16% of free drug (data not shown). These data were suggesting that vcPABA linker in position R1 was not optimal for this type of cytolysin molecules.

In Vitro Evaluation of Cytolysin Conjugates

Cytolysin ADC molecules were evaluated comparatively in vitro through proliferation arrest assay (crystal violet staining). Results are presented in FIG. 10 and IC$_{50}$ values in Table 7.

TABLE 7

| IC$_{50}$ values obtained in Proliferation Arrest Assay (nM) | | |
|---|---|---|
| Compound | HT1080-WT | HT1080-AG(+) |
| TAM334 | 1.04 | 0.77 |
| ADC-471 (HPS-157-039-001) | 5.6 | 10.33 |
| ADC-551 (HPS-157-039-002) | 964 | 552 |
| ADC-553 (HPS-157-039-004) | 90 | 108 |
| ADC-558 (HPS-157-039-005) | 555 | 0.96 |

Figure 10A:
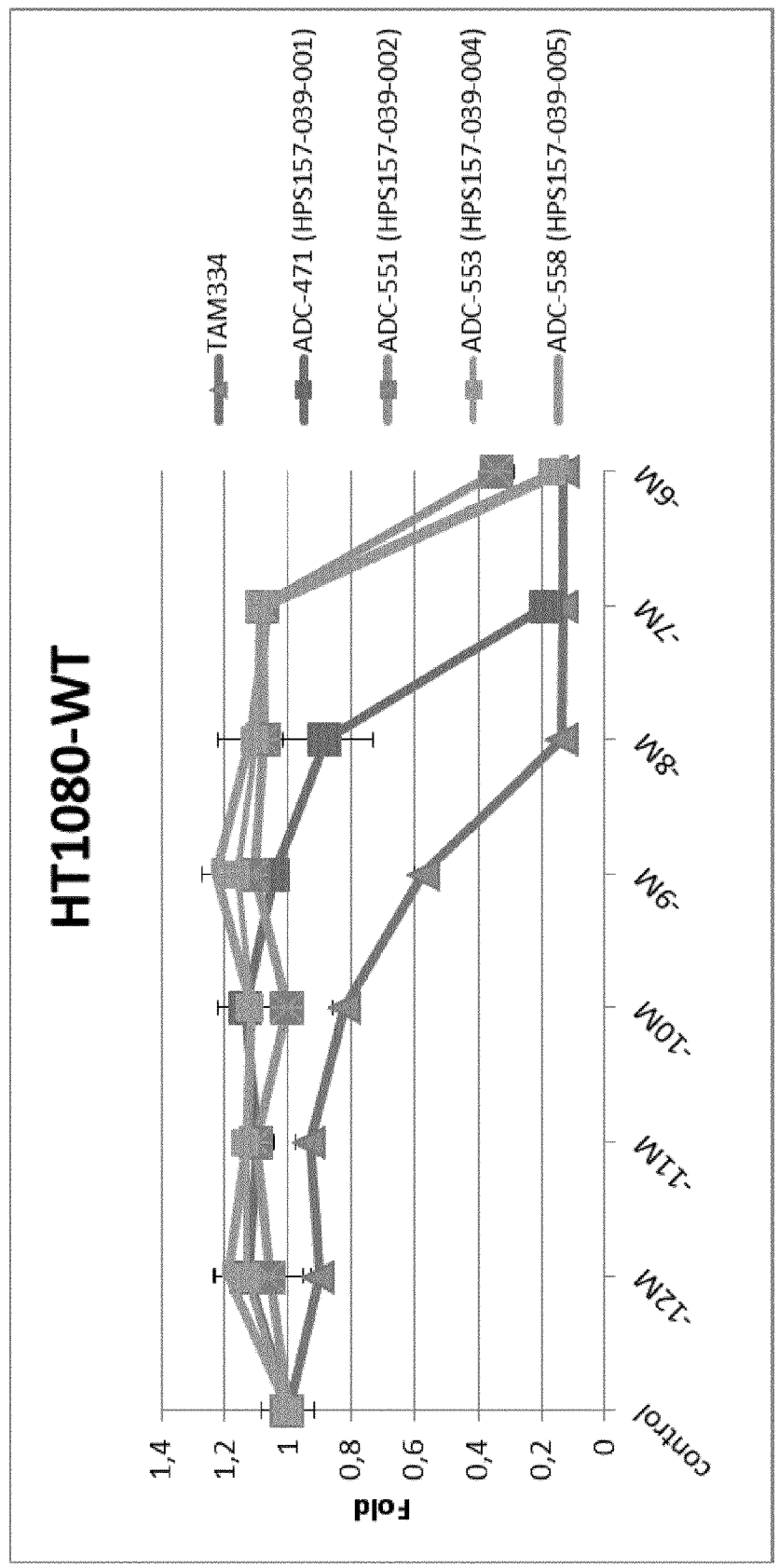
Figure 10B:
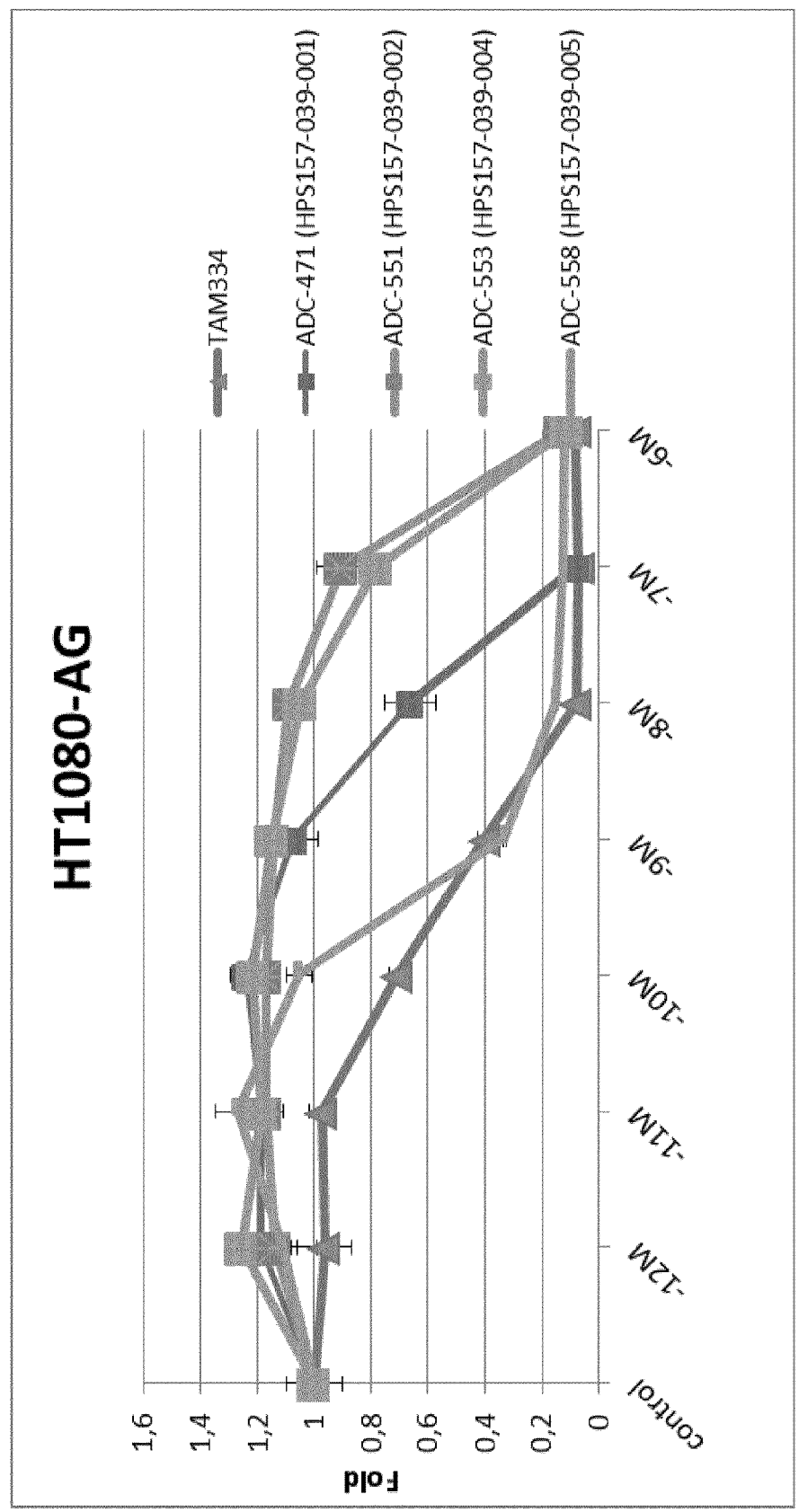

Location of vcPABA linker alone in R1 position (ADC-551) generated conjugates with much less cytotoxic activity in vitro with respect to R4 position (ADC-471) (FIG. 10;

Table 7). In addition, increasing the number of ethyleneglycol groups as spacer to vcPABA linker in R4 position (ADC-471 (n=0) versus ADC-553 (n=1) and ADC-558 (n=3)) was shown to increase antigen-specific cytotoxic activity in vitro (FIG. 10). Indeed, while ADC-471 and ADC-553 showed low and no antigen-specific cytotoxic activity (10 nM and 100 nM $IC_{50}$ range, respectively) with no difference between wild type (WT) and antigen (AG) expressing HT1080 cells, ADC-558 presented a 1 nM range specific cytotoxic activity with a specificity ratio of 500 between AG and WT HT1080 cells.

Example 6—Evaluation of In Vivo Anti-Tumoral Effect of Conjugates

Both types of immunoconjugates, recNgA- and cytolysin-conjugates, were evaluated for their anti-tumoral effect in vivo in a patient-derived xenograft mouse model for pancreas cancer (PAXF-736), previously selected for antigen expression.

Dose range studies were performed to define the maximum tolerated dose to be used in efficacy studies (not shown). For recNgA immunoconjugates, a highest tolerated dose of 0.5 mg/kg was found, while cytolysin conjugates, independently of the derivative used, were administrated at doses from 2.5 mg/kg up to 20 mg/kg, without any weight loss or toxic effect.

Immunoconjugates were then administered once a week intraperitoneally over 5 weeks. Tumor volume and body weight were measured every 2-3 days. Vehicle-treated and Gemcitabine-treated (150 mg/kg) PDX mice were used as negative and positive control groups, respectively. Results are shown in FIG. 11.

Figure 11A:
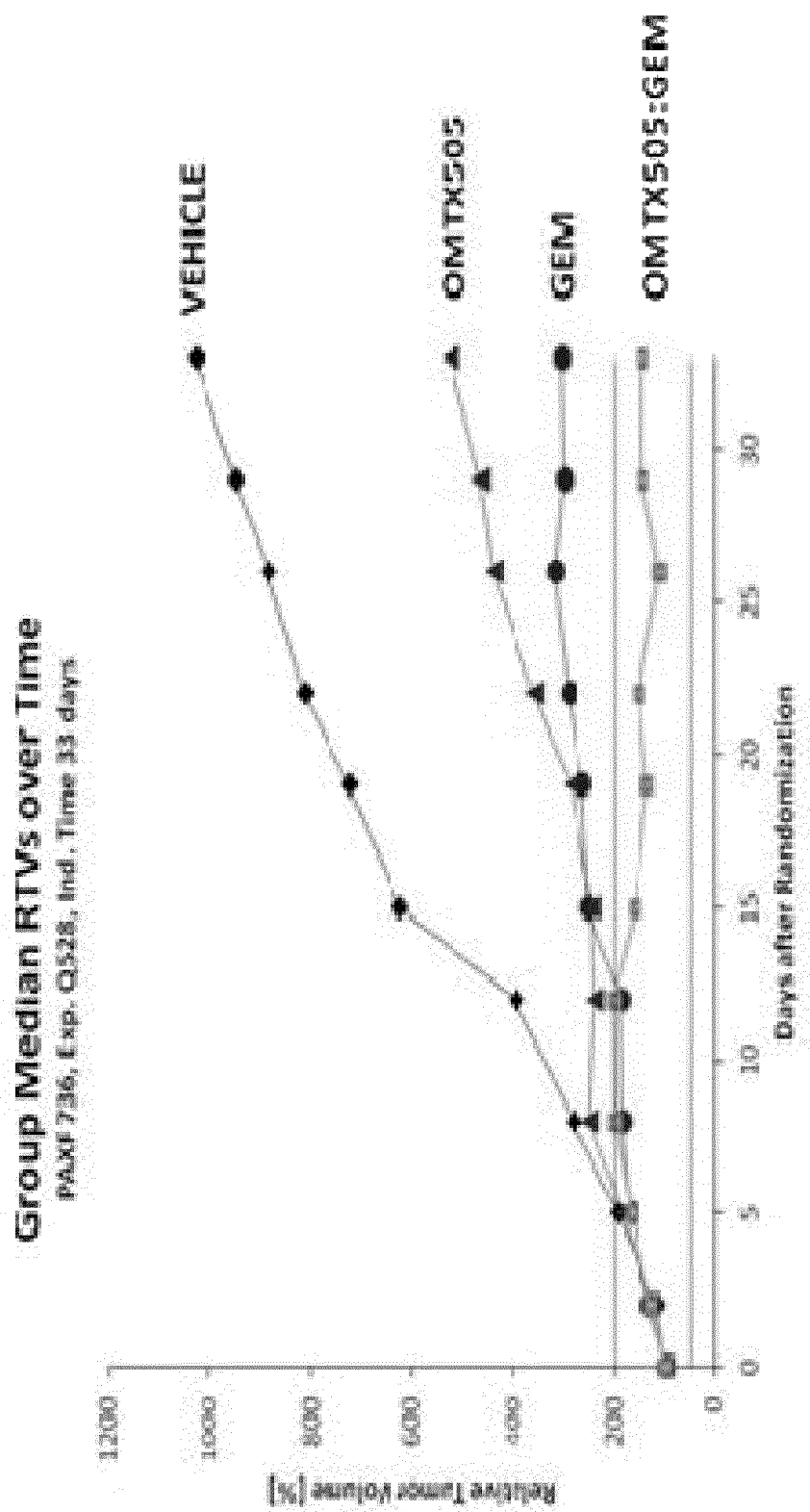

The recNgA immunoconjugates (OMTX505) presented a high in vivo anti-tumoral efficacy (60%) at a dose of 0.5 mg/kg in PDX murine models of pancreas cancer (FIG. 11A). When combined with Gemcitabine, it even showed 100% tumor growth inhibition and tumor regression.

Figure 11B:
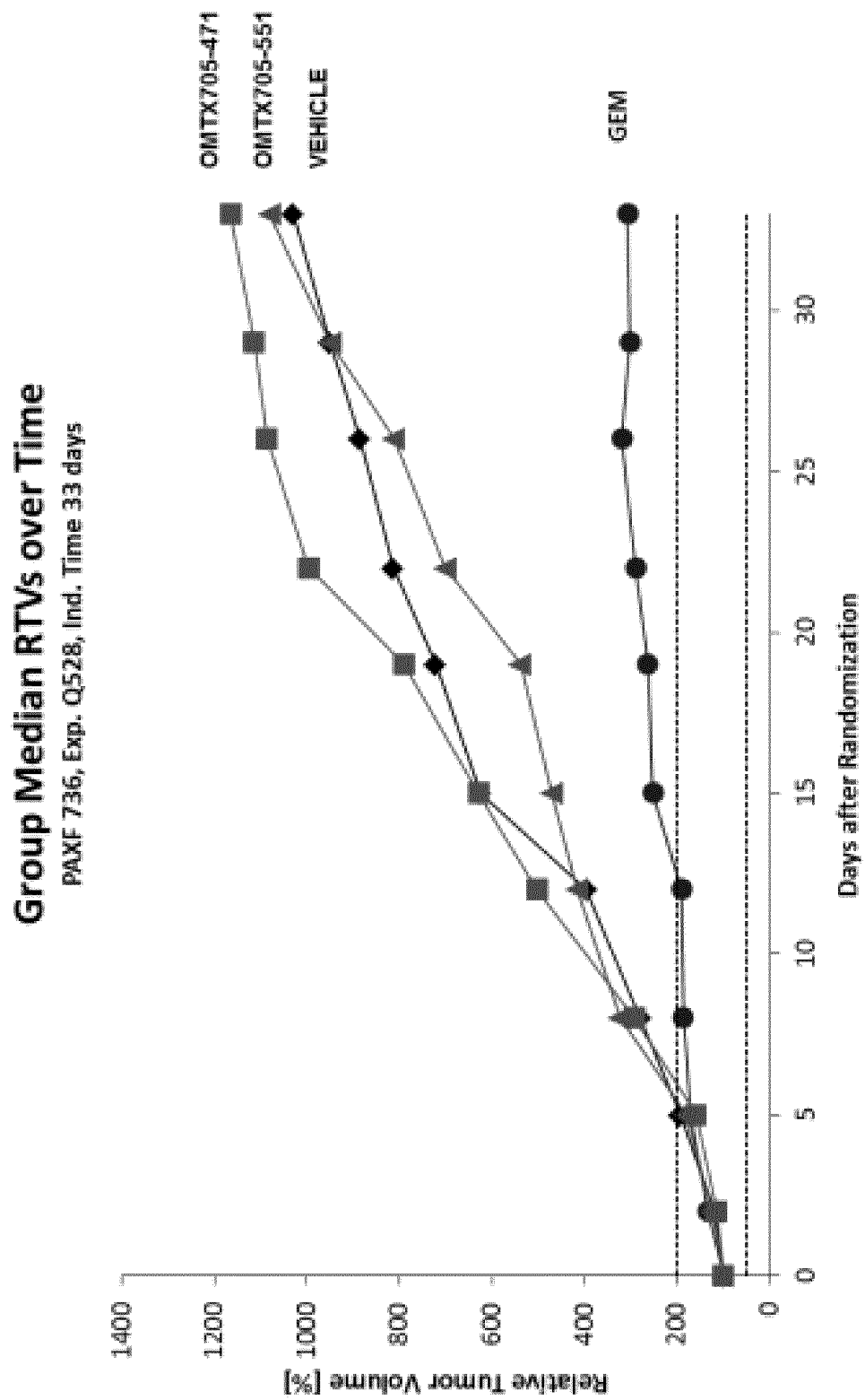

According to the in vitro results (see FIG. 10 & Table 7), location of vcPABA linker alone in R1 position (OMTX705-551) generated conjugates with no anti-tumoral activity in vivo (FIG. 11B).

Figure 11C:
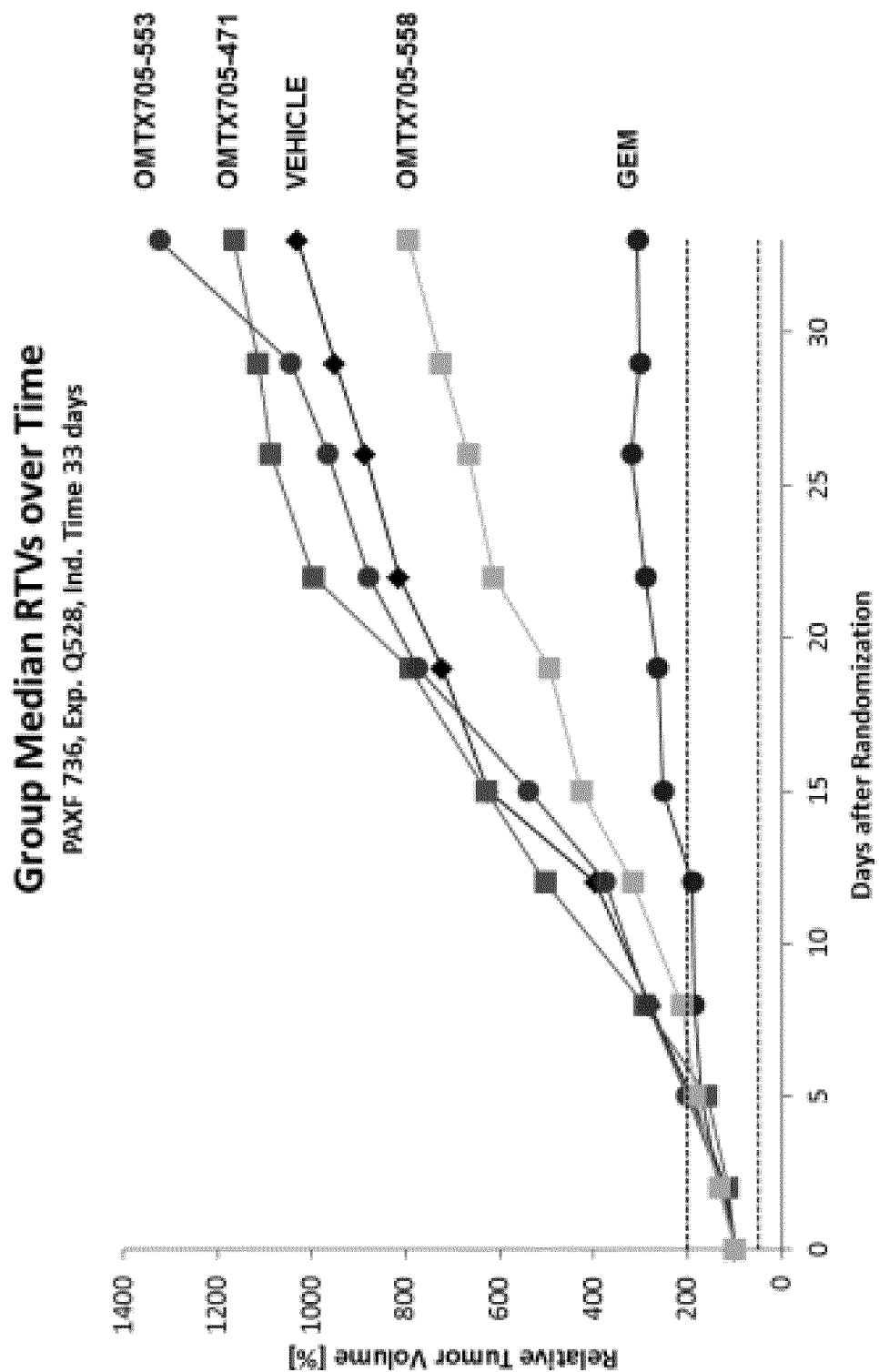

Supporting the in vitro data, increasing the number of ethylene-glycol groups as spacer to vcPABA linker in R4 position (OMTX705-471 (n=0) versus OMTX705-553 (n=1) and OMTX705-558 (n=3)) was shown to increase anti-tumoral effect in vivo (FIG. 11C). OMTX705-471 and OMTX705-553 did not show any anti-tumoral effect in vivo, while OMTX705-558 presented a 40% tumor growth inhibition effect at 2.5 mg/kg dose in PDX mouse model for pancreas cancer.

From these data, recNgA and TAM558 molecules were selected as best payloads for anti-ENG conjugates.

Example 7—Ewing Sarcoma Models

Tumor cell plasticity enables certain types of highly malignant tumor cells to dedifferentiate and engage a plastic multipotent embryonic-like phenotype, which enables them to 'adapt' during tumor progression and escape conventional therapeutic strategies. A recent study demonstrated that ENG expression correlates with tumor cell plasticity in Ewing sarcoma, and it is significantly associated with worse survival of Ewing sarcoma patients. Ewing sarcoma with reduced ENG levels showed reduced tumor growth in vivo. This study thus delineates an important role of ENG in tumor cell plasticity and progression of aggressive tumors (51).

The present inventors hypothesize the therapeutic potential of anti-ENG monoclonal antibodies, ITs and ADCs, in the treatment of Ewing Sarcoma.

14 cell line models of Ewing sarcoma have been developed for in vitro studies, and their corresponding xenograft models, for the screening and characterization of therapeutic molecules for the treatment of Ewing Sarcoma. ENG expression has been confirmed in all the 14 cell lines, and all the human Ewing sarcoma patient samples (n=10) that have been examined.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

1. Weinberg, R. A., et al., Garland science, Taylor & Francis Group LLC, New York, N.Y., USA, 2007
2. Nieman, K. M., et al., Nat. Med., 2011, 17: 1498-1503
3. Joyce, J. A., et al., Nat. Rev. Cancer, 2009, 9: 239-252
4. Hanahan, D., et al., Cancer Cell, 2012, 21: 309-322
5. Gupta, G. P., et al., Cell, 2006: 127: 679-695
6. Valastyan, S., et al., Cell, 2011, 147: 275-292
7. Meads, M. B, et al., Nat. Rev. Cancer, 2009, 9: 665-674
8. Olive, K. P., et al., Science, 2009, 324: 1457-1461
9. Acharyya, S., et al., Cell, 2012, 150: 165-178
10. Crawford, Y., et al. Cancer Cell, 2009, 15: 21-34
11. Straussman, R., Nature, 2012, 487: 500-504
12. Joyce, J. A., et al., Cancer Cell, 2005, 7: 513-520
13. Hanahan, D., et al., Cell, 2011, 144: 646-674
14. Kalluri, R., Nat. Rev. Cancer, 2006, 6: 392-401
15. Pietras, K., et al., Exp. Cell Res., 2010, 316: 1324-1331
16. Orimo, A., et al., Cell, 2005, 121: 335-348
17. Erez, N., et al., Cancer Cell, 2010, 17: 135-147
18. Olumi, A. F., et al., Cancer Res., 1999, 59: 5002-5011
19. Yang, G., et al., Proc. Natl. Acad. Sci. USA, 2006, 103: 16472-16477
20. Hwang, R. F., et al., Cancer Res., 2008, 68: 918-926
21. Hu, M., et al., Proc. Natl. Acad. Sci. USA, 2009, 106: 3372-3377
22. Medema, J. P., et al., Nature, 2011, 474: 318-326
23. Malanchi, I., et al., Nature, 2012, 481: 85-89
24. Strell, C., et al., Ups. J. Med. Sci., 2012, 117: 187-195
25. Horimoto, Y., et al., Cell Adhes. Migr., 2012, 6: 193202
26. Wu, et al., J. Cancer Mol., 2008, 4: 37-45
27. Kumar S., et al., Cancer Res., 1999, 59: 856-861
28. Li C., et al., Int. J. Cancer, 2000, 89: 122-126
29. Volkel T., et al., Bioch. and Bioph. Res. Com., 2004, 317: 515-521
30. Rüger R., et al., J. of Drug Targeting, 2006, 14: 576-582
31. Müller D., et al., J. of Immun. Methods, 2008, 339: 90-98
32. Uneda S., et al., Int. J. Cancer, 2009, 125: 1446-1453
33. Fonsatti E., et al., Cardiovasc. Res., 2010, 86: 12-19
34. Seon B. K., et al., Curr. Drug Deliv, 2011, 8: 135-143
35. Ferreras J. M., et al., Toxins, 2011, 3: 420-441
36. Muñoz R., et al., Cancer Immunol. Immunother., 2012.
37. Muñoz et al., Cancer Res., 2001

38. Trush et al., *Annu. Rev. Immunol.,* 1996, 14:49-71
39. Lambert et al., 1988,
40. Barbieri, et al., *Methods in Mol. Biol.,* 2001, 166: 71-85
41. Ghetie and Vitetta, *Mol. Biotechnol.,* 2001, 18: 251-286
42. Munoz R., et al., Cancer Lett., 2007, 256: 73-80.
43. Thorpe et al., *Cancer Res.,* 1987, 47:5924-5931
44. Fracasso et al., *Mini Rev. Med. Chem.,* 2004, 4: 545-562
45. Marsh et al., *"Immunotoxins"*, Frankel A. E. ed., Kluwer Academic Publishers, Boston, Mass., 1988, 213-237
46. Riddles et al., *Anal. Biochem.,* 1979, 94:75-81
47. Riener et al., *Anal. Bioanal. Chem,* 2002, 373:266-276
48. Gualberto A. *Expert Opin Investig Drugs.* 2012; 21(2): 205-16
49. Perez-Soler et al., *Clin. Cancer Res.,* 2000, 6: 4932-4938;
50. Yabuchi et al., *Cancer Letters,* 2013
51. Padarli et al., *Oncogene,* 2011, 20: 334-345

The invention claimed is:
1. A conjugate having the formula I:

A-(L-D)$_p$        (I)

or a pharmaceutically acceptable salt or solvate thereof, wherein:
A is an antibody that selectively binds Endoglin;
L is a linker;
D is a drug comprising a cytolysin; and
p is 1 to 10,
wherein the cytolysin is of formula IV:

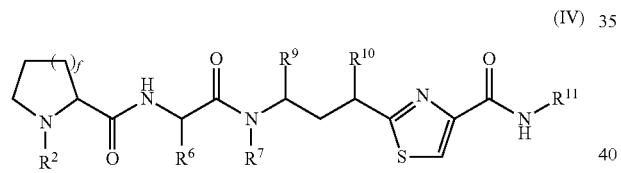

wherein:
$R^2$ is H or $C_1$-$C_4$ alkyl;
$R^6$ is $C_1$-$C_6$ alkyl;
$R^7$ is $C_1$-$C_6$ alkyl, $CH_2OR^{19}$ or $CH_2OCOR^{20}$, wherein $R^{19}$ is alkyl, $R^{20}$ is $C_2$-$C_6$-alkenyl, phenyl, or $CH_2$-phenyl;
$R^9$ is $C_1$-$C_6$ alkyl;
$R^{10}$ is H, OH, O-alkyl or O-acetyl;
f is 1 or 2;
$R^{11}$ has the following structure:

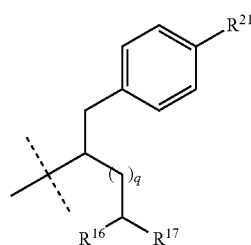

wherein
$R^{21}$ is H, OH, halogen, $NH_2$, alkyloxy, phenyl, alkyl amino or dialkyl amino;
$R^{16}$ is H or a $C_1$-$C_6$-alkyl group;

$R^{17}$ is directly or indirectly attached to linker L; and
q is 0, 1, 2 or 3.

2. The conjugate of claim 1, wherein A comprises heavy chain complementarity determining regions 1-3 (CDRH1-3) and light chain complementarity determining regions 1-3 (CDRL1-3) having the following amino acid sequences:
(i) CDRH1: SEQ ID NO: 7;
(ii) CDRH2: SEQ ID NO: 8;
(iii) CDRH3: SEQ ID NO: 9;
(iv) CDRL1: SEQ ID NO: 10;
(v) CDRL2: SEQ ID NO: 11; and
(vi) CDRL3: SEQ ID NO: 12.

3. The conjugate of claim 2, wherein A comprises a heavy chain variable region (VH) comprising the amino acid sequence of SEQ ID NO: 5 and a light chain variable region (VL) comprising the amino acid sequence of SEQ ID NO: 6.

4. The conjugate of claim 2, wherein A comprises a heavy chain comprising the amino acid sequence of SEQ ID NO: 3 and a light chain comprising the amino acid sequence of SEQ ID NO: 4.

5. The conjugate of claim 1, wherein $R^{17}$ is C(O)X, CONHNHX, OX, NHX or SX, wherein X is a bond to linker L.

6. The conjugate of claim 1, wherein linker L further comprises a spacer.

7. The conjugate of claim 6, wherein the spacer has a chain length of 2 to 30 atoms.

8. The conjugate of claim 7, wherein the spacer comprises or consists of a group —$(CH_2)_n$— or —$(OCH_2CH_2)_n$—, wherein n=1 to 10.

9. The conjugate of claim 6, wherein the spacer is directly attached to group $R^{17}$, or is attached to group $R^{17}$ via a bridging group.

10. The conjugate of claim 9, wherein the spacer is attached to group $R^{17}$ via a —C(O)X bridging group, wherein X is a bond to $R^{17}$.

11. The conjugate of claim 1, wherein D comprises a cytolysin having the following structure:

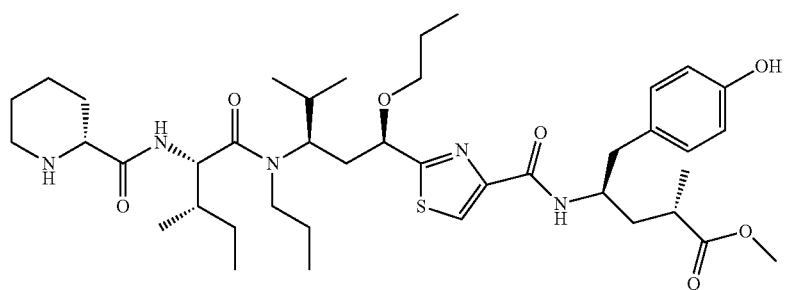 [SMILES: CCCO[C@H](C[C@H](C(C)C)N(CCC)C(=O)[C@@H](NC(=O)[C@H]1CCCCN1)[C@@H](C)CC)c1nc(C(=O)N[C@@H](Cc2ccc(O)cc2)C[C@H](C)C(=O)OC)cs1]
or
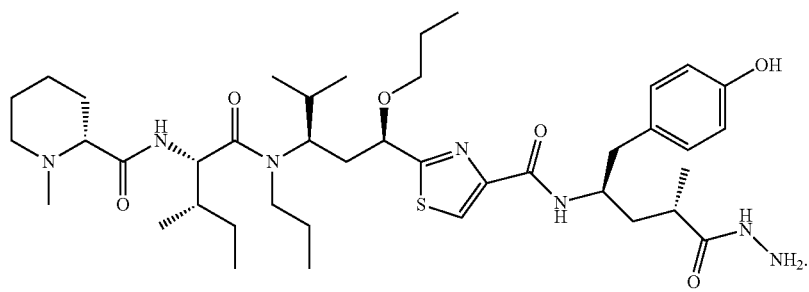 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(O)cc2)C[C@H](C)C(=O)NN)cs1]
12. The conjugate of claim 1, wherein L comprises an attachment group for attachment to A and protease cleavable portion.
13. The conjugate of claim 12, wherein L comprises maleimidocaproyl-valine-citrulline-p-aminobenzylcarbamate.
14. The conjugate of claim 1, wherein L-D has a structure selected from the group consisting of:

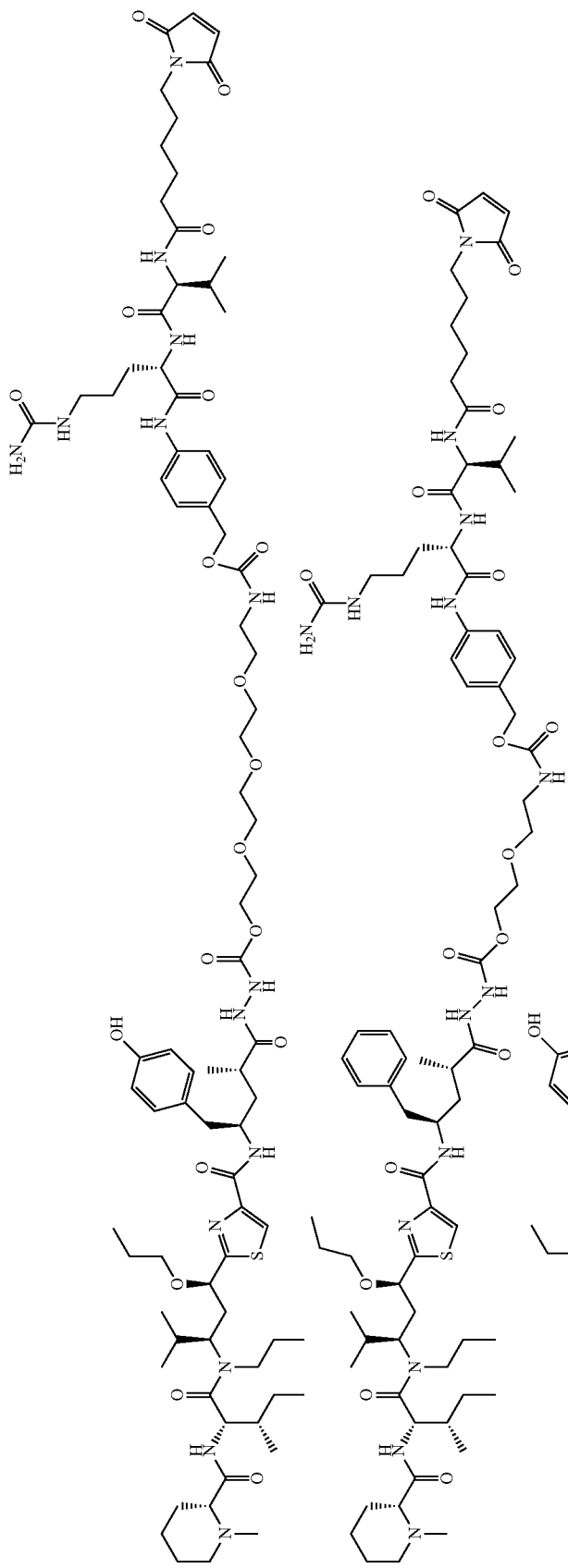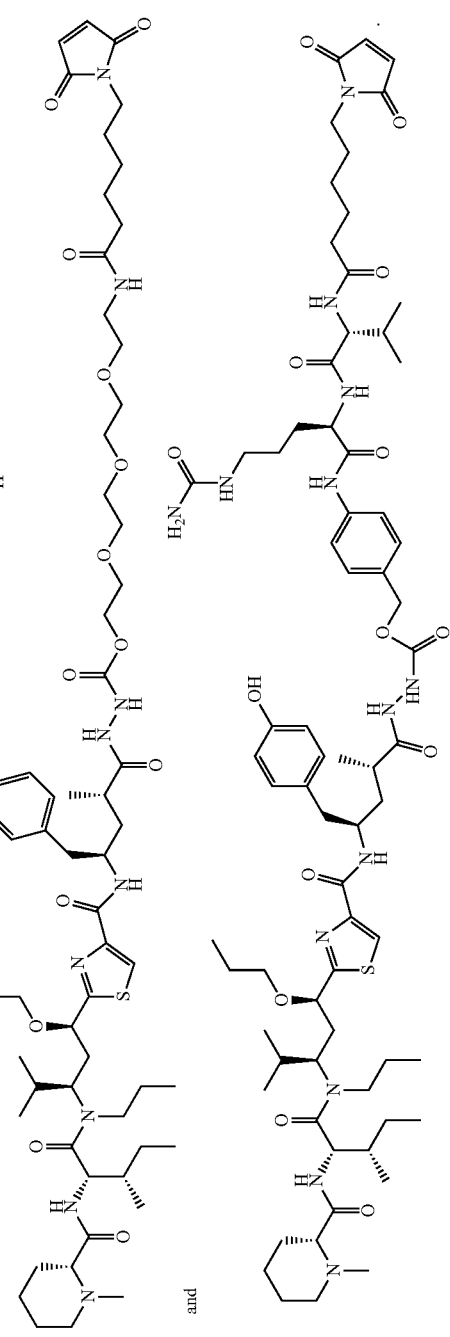

15. A method of treating a tumor in a mammalian subject, wherein said tumor and/or stroma surrounding said tumor expresses endoglin, said method comprising administering a therapeutically effective amount of a conjugate as defined in claim 1 to the subject in need thereof.

16. The method of claim 15, wherein said conjugate is administered simultaneously, sequentially or separately with one or more other antitumor drugs.

17. The method of claim 16, wherein said one or more other antitumor drugs comprise a cytotoxic chemotherapeutic agent or an anti-angiogenic agent or an immunotherapeutic agent.

18. The method of claim 17, wherein said one or more other antitumor drugs comprise Gemcitabine, Abraxane, bevacizumab, itraconazole, or carboxyamidotriazole, an anti-PD-1 molecule or an anti-PD-L1 molecule.

19. The method of claim 18, wherein said anti-PD-1 molecule or anti-PD-L1 molecule comprises nivolumab or pembrolizumab.

20. The method of claim 15, wherein the tumor is an endoglin-expressing blood neoplasm, pancreatic cancer, Ewing sarcoma, breast cancer, melanoma, lung cancer, head and neck cancer, ovarian cancer, bladder cancer or colon cancer.

21. A method of treating an endoglin-expressing inflammatory condition or an endoglin-expressing eye disease in a mammalian subject, said method comprising administering a therapeutically effective amount of the conjugate as defined in claim 1 to the subject in need thereof.

22. The method according to claim 21, wherein:

said inflammatory condition is endoglin-expressing rheumatoid arthritis; and/or said eye disease is endoglin-expressing diabetic retinopathy or endoglin-expressing macular degeneration.

\* \* \* \* \*

SEQUENCE LISTING

```
<160> NUMBER OF SEQ ID NOS: 28

<210> SEQ ID NO 1
<211> LENGTH: 467
<212> TYPE: PRT
<213> ORGANISM: Artificial sequence
<220> FEATURE:
<223> OTHER INFORMATION: Synthetic sequence: Anti-human Endoglin
      A5-IgG1-HC

<400> SEQUENCE: 1
```

Met Glu Thr Asp Thr Leu Leu Leu Trp Val Leu Leu Leu Trp Val Pro
1               5                   10                  15

Gly Ser Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Ala Met Ser Trp Val Arg Gln Ala Pro Gly Lys Gly
    50                  55                  60

Leu Glu Trp Val Ser Ala Ile Tyr Gly Ser Asp Gly Asp Thr Thr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Val Phe Tyr Thr Ala Gly Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

```
Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 2
<211> LENGTH: 234
<212> TYPE: PRT
<213> ORGANISM: Artificial sequence
<220> FEATURE:
<223> OTHER INFORMATION: Synthetic sequence: Anti-human Endoglin
      A5-IgG1-LC

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Glu Leu Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Ile Ser Ser Ser Leu Asn Trp Tyr Gln Gln Lys Pro Gly Lys Ala Pro
    50                  55                  60

Lys Leu Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Pro
            100                 105                 110

Ala Lys Pro Pro Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
```

```
                    165                 170                 175
Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 3
<211> LENGTH: 447
<212> TYPE: PRT
<213> ORGANISM: Artificial sequence
<220> FEATURE:
<223> OTHER INFORMATION: Synthetic sequence: A5-IgG1-HC - without signal
      sequence

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Tyr Gly Ser Asp Gly Asp Thr Thr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Phe Tyr Thr Ala Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 4
<211> LENGTH: 214
<212> TYPE: PRT
<213> ORGANISM: Artificial sequence
<220> FEATURE:
<223> OTHER INFORMATION: Synthetic sequence: A5-IgG1-LC - without signal
      sequence

<400> SEQUENCE: 4

Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ser
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Pro Ala Lys Pro Pro
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205
```

Phe Asn Arg Gly Glu Cys
    210

<210> SEQ ID NO 5
<211> LENGTH: 118
<212> TYPE: PRT
<213> ORGANISM: Artificial sequence
<220> FEATURE:
<223> OTHER INFORMATION: Synthetic sequence: A5-VH

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Tyr Gly Ser Asp Gly Asp Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Phe Tyr Thr Ala Gly Phe Asp Tyr Trp Gly Gln Gly Thr
            100                 105                 110

Leu Val Thr Val Ser Ser
        115

<210> SEQ ID NO 6
<211> LENGTH: 108
<212> TYPE: PRT
<213> ORGANISM: Artificial sequence
<220> FEATURE:
<223> OTHER INFORMATION: Synthetic sequence: A5-VL

<400> SEQUENCE: 6

Asp Ile Glu Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Pro Ala Lys Pro Pro
                85                  90                  95

Thr Phe Gly Gln Gly Thr Lys Leu Glu Ile Lys Arg
            100                 105

<210> SEQ ID NO 7
<211> LENGTH: 5
<212> TYPE: PRT
<213> ORGANISM: Artificial sequence
<220> FEATURE:
<223> OTHER INFORMATION: Synthetic sequence: A5-CDRH1

<400> SEQUENCE: 7

Ser Tyr Ala Met Ser
1               5

<210> SEQ ID NO 8
<211> LENGTH: 11
<212> TYPE: PRT
<213> ORGANISM: Artificial sequence
<220> FEATURE:
<223> OTHER INFORMATION: Synthetic sequence: A5-CDRH2

<400> SEQUENCE: 8

Ala Ile Tyr Gly Ser Asp Gly Asp Thr Thr Tyr
1               5                   10

<210> SEQ ID NO 9
<211> LENGTH: 9
<212> TYPE: PRT
<213> ORGANISM: Artificial sequence
<220> FEATURE:
<223> OTHER INFORMATION: Synthetic sequence: A5-CDRH3

<400> SEQUENCE: 9

Val Phe Tyr Thr Ala Gly Phe Asp Tyr
1               5

<210> SEQ ID NO 10
<211> LENGTH: 11
<212> TYPE: PRT
<213> ORGANISM: Artificial sequence
<220> FEATURE:
<223> OTHER INFORMATION: Synthetic sequence: A5-CDRL1

<400> SEQUENCE: 10

Arg Ala Ser Gln Ser Ile Ser Ser Ser Leu Asn
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic sequence: A5-CDRL2

<400> SEQUENCE: 11

Ala Ala Ser Ser Leu Gln Ser
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic sequence: A5-CDRL3

<400> SEQUENCE: 12

Gln Gln Ala Pro Ala Lys Pro Pro Thr
1               5

<210> SEQ ID NO 13
<211> LENGTH: 466
<212> TYPE: PRT
<213> ORGANISM: Artificial sequence
<220> FEATURE:
<223> OTHER INFORMATION: Synthetic sequence: Anti-murine Endoglin
      mE12-IgG1-HC

<400> SEQUENCE: 13

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Val Val
            20                  25                  30

Gln Pro Gly Arg Ser Leu Arg Leu Ser Cys Ala Ala Ser Gly Phe Thr
            35                  40                  45

Phe Ser Ser Tyr Gly Met His Trp Val Arg Gln Ala Pro Gly Lys Gly
50                  55                  60

Leu Val Trp Val Ser Arg Ile Asn Ser Asp Gly Ser Ser Thr Ser Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
                100                 105                 110

Val Tyr Tyr Cys Ala Arg Ala Thr Gly Thr Trp Val Met Ser Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
```

```
                    420             425             430
Lys Ser Arg Trp Gln Gln Gly Asn Val Phe Ser Cys Ser Val Met His
        435             440             445

Glu Ala Leu His Asn His Tyr Thr Gln Lys Ser Leu Ser Leu Ser Pro
    450             455             460

Gly Lys
465

<210> SEQ ID NO 14
<211> LENGTH: 232
<212> TYPE: PRT
<213> ORGANISM: Artificial sequence
<220> FEATURE:
<223> OTHER INFORMATION: Synthetic sequence: Anti-murine Endoglin
      mE12-IgG1-LC

<400> SEQUENCE: 14

Met Glu Thr Asp Thr Leu Leu Leu Trp Val Leu Leu Leu Trp Val Pro
1               5                   10                  15

Gly Ser Thr Gly Ser Ser Glu Leu Ile Gln Asp Pro Ala Val Ser Val
            20                  25                  30

Ala Leu Gly Gln Thr Val Arg Ile Thr Cys Gln Gly Asp Ser Leu Arg
        35                  40                  45

Ser Tyr Tyr Ala Ser Trp Tyr Gln Gln Lys Pro Gly Gln Ala Pro Val
    50                  55                  60

Leu Val Ile Tyr Gly Lys Asn Asn Arg Pro Ser Gly Ile Pro Asp Arg
65                  70                  75                  80

Phe Ser Gly Ser Ser Ser Gly Asn Thr Ala Ser Leu Thr Ile Thr Gly
                85                  90                  95

Ala Gln Ala Glu Asp Glu Ala Asp Tyr Tyr Cys Asn Ser Arg Asp Ser
            100                 105                 110

Ser Gly Thr Val Phe Gly Gly Gly Thr Lys Leu Thr Val Leu Gly Gln
        115                 120                 125

Pro Lys Ala Asn Pro Thr Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Gly Ser Pro Val Lys
                165                 170                 175

Ala Gly Val Glu Thr Thr Lys Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 15
<211> LENGTH: 446
<212> TYPE: PRT
<213> ORGANISM: Artificial sequence
<220> FEATURE:
<223> OTHER INFORMATION: Synthetic sequence: mE12-IgG1-HC - without
      signal sequence

<400> SEQUENCE: 15

Glu Val Gln Leu Val Glu Ser Gly Gly Gly Val Val Gln Pro Gly Arg
```

-continued

```
1               5                   10                  15
Ser Leu Arg Leu Ser Cys Ala Ala Ser Gly Phe Thr Phe Ser Ser Tyr
                20                  25                  30
Gly Met His Trp Val Arg Gln Ala Pro Gly Lys Gly Leu Val Trp Val
                35                  40                  45
Ser Arg Ile Asn Ser Asp Gly Ser Ser Thr Ser Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ala Thr Gly Thr Trp Val Met Ser Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
                195                 200                 205
Thr Lys Val Asp Lys Lys Val Glu Pro Lys Ser Cys Asp Lys Thr His
    210                 215                 220
Thr Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
                290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
```

```
Asn His Tyr Thr Gln Lys Ser Leu Ser Leu Ser Pro Gly Lys
        435                 440                 445

<210> SEQ ID NO 16
<211> LENGTH: 212
<212> TYPE: PRT
<213> ORGANISM: Artificial sequence
<220> FEATURE:
<223> OTHER INFORMATION: Synthetic sequence: mE12-IgG1-LC - without
      signal sequence

<400> SEQUENCE: 16

Ser Ser Glu Leu Ile Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr Val
                85                  90                  95

Phe Gly Gly Gly Thr Lys Leu Thr Val Leu Gly Gln Pro Lys Ala Asn
            100                 105                 110

Pro Thr Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Gly Ser Pro Val Lys Ala Gly Val Glu
145                 150                 155                 160

Thr Thr Lys Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 17
<211> LENGTH: 117
<212> TYPE: PRT
<213> ORGANISM: Artificial sequence
<220> FEATURE:
<223> OTHER INFORMATION: Synthetic sequence: mE12-VH

<400> SEQUENCE: 17

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Thr Gly Thr Trp Val Met Ser Trp Gly Gln Gly Thr Leu
            100                 105                 110

Val Thr Val Ser Ser
        115

<210> SEQ ID NO 18
<211> LENGTH: 107
<212> TYPE: PRT
<213> ORGANISM: Artificial sequence
<220> FEATURE:
<223> OTHER INFORMATION: Synthetic sequence: mE12-VL

<400> SEQUENCE: 18

Ser Ser Glu Leu Ile Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr Val
                85                  90                  95

Phe Gly Gly Gly Thr Lys Leu Thr Val Leu Gly
            100                 105

<210> SEQ ID NO 19
<211> LENGTH: 5
<212> TYPE: PRT
<213> ORGANISM: Artificial sequence
<220> FEATURE:
<223> OTHER INFORMATION: Synthetic sequence: mE12-CDRH1

<400> SEQUENCE: 19

Ser Tyr Gly Met His
1               5

<210> SEQ ID NO 20
<211> LENGTH: 17
<212> TYPE: PRT
<213> ORGANISM: Artificial sequence
<220> FEATURE:
<223> OTHER INFORMATION: Synthetic sequence: mE12-CDRH2

<400> SEQUENCE: 20

Arg Ile Asn Ser Asp Gly Ser Ser Thr Ser Tyr Ala Asp Ser Val Lys
1               5                   10                  15

Gly

<210> SEQ ID NO 21
<211> LENGTH: 8
<212> TYPE: PRT
<213> ORGANISM: Artificial sequence
<220> FEATURE:
<223> OTHER INFORMATION: Synthetic sequence: mE12-CDRH3
```

<400> SEQUENCE: 21

Ala Thr Gly Thr Trp Val Met Ser
1               5

<210> SEQ ID NO 22
<211> LENGTH: 11
<212> TYPE: PRT
<213> ORGANISM: Artificial sequence
<220> FEATURE:
<223> OTHER INFORMATION: Synthetic sequence: mE12-CDRL1

<400> SEQUENCE: 22

Gln Gly Asp Ser Leu Arg Ser Tyr Tyr Ala Ser
1               5                   10

<210> SEQ ID NO 23
<211> LENGTH: 7
<212> TYPE: PRT
<213> ORGANISM: Artificial sequence
<220> FEATURE:
<223> OTHER INFORMATION: Synthetic sequence: mE12-CDRL2

<400> SEQUENCE: 23

Gly Lys Asn Asn Arg Pro Ser
1               5

<210> SEQ ID NO 24
<211> LENGTH: 9
<212> TYPE: PRT
<213> ORGANISM: Artificial sequence
<220> FEATURE:
<223> OTHER INFORMATION: Synthetic sequence: mE12-CDRL3

<400> SEQUENCE: 24

Asn Ser Arg Asp Ser Ser Gly Thr Val
1               5

<210> SEQ ID NO 25
<211> LENGTH: 256
<212> TYPE: PRT
<213> ORGANISM: Artificial sequence
<220> FEATURE:
<223> OTHER INFORMATION: Synthetic sequence: Recombinant Nigrin-b
      A-chain amino acid sequence

<400> SEQUENCE: 25

Met Ile Asp Tyr Pro Ser Val Ser Phe Asn Leu Asp Gly Ala Lys Ser
1               5                   10                  15

Ala Thr Tyr Arg Asp Phe Leu Ser Asn Leu Arg Lys Thr Val Ala Thr
            20                  25                  30

Gly Thr Tyr Glu Val Asn Gly Leu Pro Val Leu Arg Arg Glu Ser Glu
        35                  40                  45

Val Gln Val Lys Ser Arg Phe Val Leu Val Pro Leu Thr Asn Tyr Asn
    50                  55                  60

Gly Asn Thr Val Thr Leu Ala Val Asp Val Thr Asn Leu Tyr Val Val
65                  70                  75                  80

Ala Phe Ser Gly Asn Ala Asn Ser Tyr Phe Phe Lys Asp Ala Thr Glu
                85                  90                  95

Val Gln Lys Ser Asn Leu Phe Val Gly Thr Lys Gln Asn Thr Leu Ser
            100                 105                 110

Phe Thr Gly Asn Tyr Asp Asn Leu Glu Thr Ala Ala Asn Thr Arg Arg
        115                 120                 125

```
Glu Ser Ile Glu Leu Gly Pro Ser Pro Leu Asp Gly Ala Ile Thr Ser
    130                 135                 140

Leu Tyr His Gly Asp Ser Val Ala Arg Ser Leu Leu Val Val Ile Gln
145                 150                 155                 160

Met Val Ser Glu Ala Ala Arg Phe Arg Tyr Ile Glu Gln Glu Val Arg
                165                 170                 175

Arg Ser Leu Gln Gln Ala Thr Ser Phe Thr Pro Asn Ala Leu Met Leu
            180                 185                 190

Ser Met Glu Asn Asn Trp Ser Ser Met Ser Leu Glu Ile Gln Gln Ala
        195                 200                 205

Gly Asn Asn Val Ser Pro Phe Phe Gly Thr Val Gln Leu Leu Asn Tyr
    210                 215                 220

Asp His Thr His Arg Leu Val Asp Asn Phe Glu Glu Leu Tyr Lys Ile
225                 230                 235                 240

Thr Gly Ile Ala Ile Leu Leu Phe Arg Cys Ser Ser Pro Ser Asn Asp
                245                 250                 255
```

<210> SEQ ID NO 26
<211> LENGTH: 765
<212> TYPE: DNA
<213> ORGANISM: Artificial sequence
<220> FEATURE:
<223> OTHER INFORMATION: Synthetic sequence: Nucleotide sequence encoding recombinant Nigrin-b A-chain

<400> SEQUENCE: 26

```
atagactatc cctccgtctc cttcaacttg gatggagcca agtcggctac atacagggac      60
ttcctcagca acctgcgaaa aacagtggca actggcacct atgaagtaaa cggtttacca     120
gtactgaggc gcgaaagtga agtacaggtc aagagtcggt tcgttctcgt ccctctcacc     180
aattacaatg gaaacaccgt cacgttggca gtagatgtga ccaaccttta cgtggtggct     240
tttagtggaa atgcaaactc ctactttttc aaggacgcta cggaagttca aaagagtaat     300
ttattcgttg gcaccaagca aaatacgtta tccttcacgg gtaattatga caaccttgag     360
actgcggcga atactaggag ggagtctatc gaactgggac ccagtccgct agatggagcc     420
attacaagtt tgtatcatgg tgatagcgta gcccgatctc tccttgtggt aattcagatg     480
gtctcggaag cggcaaggtt cagatacatt gagcaagaag tgcgccgaag cctacagcag     540
gctacaagct tcacaccaaa tgctttgatg ctgagcatgg agaacaactg gtcgtctatg     600
tccttggaga tccagcaggc gggaaataat gtatcaccct tctttgggac cgttcagctt     660
ctaaattacg atcacactca ccgcctagtt gacaactttg aggaactcta taagattacg     720
gggatagcaa ttcttctctt ccgttgctcc tcaccaagca atgat                     765
```

<210> SEQ ID NO 27
<211> LENGTH: 658
<212> TYPE: PRT
<213> ORGANISM: Homo sapiens

<400> SEQUENCE: 27

```
Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
```

```
                 50                  55                  60
His Val Leu Phe Leu Glu Phe Pro Thr Gly Pro Ser Gln Leu Glu Leu
 65                  70                  75                  80

Thr Leu Gln Ala Ser Lys Gln Asn Gly Thr Trp Pro Arg Glu Val Leu
                 85                  90                  95

Leu Val Leu Ser Val Asn Ser Ser Val Phe Leu His Leu Gln Ala Leu
            100                 105                 110

Gly Ile Pro Leu His Leu Ala Tyr Asn Ser Ser Leu Val Thr Phe Gln
        115                 120                 125

Glu Pro Pro Gly Val Asn Thr Thr Glu Leu Pro Ser Phe Pro Lys Thr
    130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
        355                 360                 365

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430

Ser Ser Pro Gln Arg Lys Lys Val His Cys Leu Asn Met Asp Ser Leu
        435                 440                 445

Ser Phe Gln Leu Gly Leu Tyr Leu Ser Pro His Phe Leu Gln Ala Ser
    450                 455                 460

Asn Thr Ile Glu Pro Gly Gln Gln Ser Phe Val Gln Val Arg Val Ser
465                 470                 475                 480
```

```
Pro Ser Val Ser Glu Phe Leu Leu Gln Leu Asp Ser Cys His Leu Asp
                485                 490                 495

Leu Gly Pro Glu Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
            515                 520                 525

Arg Phe Ser Phe Leu Leu His Phe Tyr Thr Val Pro Ile Pro Lys Thr
        530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
            595                 600                 605

Ala Leu Trp Tyr Ile Tyr Ser His Thr Arg Ser Pro Ser Lys Arg Glu
            610                 615                 620

Pro Val Val Ala Val Ala Pro Ala Ser Ser Glu Ser Ser Ser Thr
625                 630                 635                 640

Asn His Ser Ile Gly Ser Thr Gln Ser Thr Pro Cys Ser Thr Ser Ser
                645                 650                 655

Met Ala

<210> SEQ ID NO 28
<211> LENGTH: 653
<212> TYPE: PRT
<213> ORGANISM: Mus musculus

<400> SEQUENCE: 28

Met Asp Arg Gly Val Leu Pro Leu Pro Ile Thr Leu Leu Phe Val Ile
1               5                   10                  15

Tyr Ser Phe Val Pro Thr Thr Gly Leu Ala Glu Arg Val Gly Cys Asp
                20                  25                  30

Leu Gln Pro Val Asp Pro Thr Arg Gly Glu Val Thr Phe Thr Thr Ser
            35                  40                  45

Gln Val Ser Glu Gly Cys Val Ala Gln Ala Ala Asn Ala Val Arg Glu
        50                  55                  60

Val His Val Leu Phe Leu Asp Phe Pro Gly Met Leu Ser His Leu Glu
65                  70                  75                  80

Leu Thr Leu Gln Ala Ser Lys Gln Asn Gly Thr Glu Thr Gln Glu Val
                85                  90                  95

Phe Leu Val Leu Val Ser Asn Lys Asn Val Phe Val Lys Phe Gln Ala
                100                 105                 110

Pro Glu Ile Pro Leu His Leu Ala Tyr Asp Ser Ser Leu Val Ile Phe
            115                 120                 125
```

```
Gln Gly Gln Pro Arg Val Asn Ile Thr Val Leu Pro Ser Leu Thr Ser
    130                 135                 140

Arg Lys Gln Ile Leu Asp Trp Ala Ala Thr Lys Gly Ala Ile Thr Ser
145                 150                 155                 160

Ile Ala Ala Leu Asp Asp Pro Gln Ser Ile Val Leu Gln Leu Gly Gln
                165                 170                 175

Asp Pro Lys Ala Pro Phe Leu Cys Leu Pro Glu Ala His Lys Asp Met
                180                 185                 190

Gly Ala Thr Leu Glu Trp Gln Pro Arg Ala Gln Thr Pro Val Gln Ser
                195                 200                 205

Cys Arg Leu Glu Gly Val Ser Gly His Lys Glu Ala Tyr Ile Leu Arg
210                 215                 220

Ile Leu Pro Gly Ser Glu Ala Gly Pro Arg Thr Val Thr Val Met Met
225                 230                 235                 240

Glu Leu Ser Cys Thr Ser Gly Asp Ala Ile Leu Ile Leu His Gly Pro
                245                 250                 255

Pro Tyr Val Ser Trp Phe Ile Asp Ile Asn His Ser Met Gln Ile Leu
                260                 265                 270

Thr Thr Gly Glu Tyr Ser Val Lys Ile Phe Pro Gly Ser Lys Val Lys
                275                 280                 285

Gly Val Glu Leu Pro Asp Thr Pro Gln Gly Leu Ile Ala Glu Ala Arg
290                 295                 300

Lys Leu Asn Ala Ser Ile Val Thr Ser Phe Val Glu Leu Pro Leu Val
305                 310                 315                 320

Ser Asn Val Ser Leu Arg Ala Ser Ser Cys Gly Gly Val Phe Gln Thr
                325                 330                 335

Thr Pro Ala Pro Val Val Thr Thr Pro Pro Lys Asp Thr Cys Ser Pro
                340                 345                 350

Val Leu Leu Met Ser Leu Ile Gln Pro Lys Cys Gly Asn Gln Val Met
                355                 360                 365

Thr Leu Ala Leu Asn Lys Lys His Val Gln Thr Leu Gln Cys Thr Ile
                370                 375                 380

Thr Gly Leu Thr Phe Trp Asp Ser Ser Cys Gln Ala Glu Asp Thr Asp
385                 390                 395                 400

Asp His Leu Val Leu Ser Ser Ala Tyr Ser Ser Cys Gly Met Lys Val
                405                 410                 415

Thr Ala His Val Val Ser Asn Glu Val Ile Ile Ser Phe Pro Ser Gly
                420                 425                 430

Ser Pro Pro Leu Arg Lys Lys Val Gln Cys Ile Asp Met Asp Ser Leu
                435                 440                 445

Ser Phe Gln Leu Gly Leu Tyr Leu Ser Pro His Phe Leu Gln Ala Ser
    450                 455                 460

Asn Thr Ile Glu Leu Gly Gln Gln Ala Phe Val Gln Val Ser Val Ser
465                 470                 475                 480

Pro Leu Thr Ser Glu Val Thr Val Gln Leu Asp Ser Cys His Leu Asp
                485                 490                 495

Leu Gly Pro Glu Gly Asp Met Val Glu Leu Ile Gln Ser Arg Thr Ala
                500                 505                 510

Lys Gly Ser Cys Val Thr Leu Leu Ser Pro Ser Pro Glu Gly Asp Pro
    515                 520                 525

Arg Phe Ser Phe Leu Leu Arg Val Tyr Met Val Pro Thr Pro Thr Ala
    530                 535                 540
```

-continued

```
Gly Thr Leu Ser Cys Asn Leu Ala Leu Arg Pro Ser Thr Leu Ser Gln
545                 550                 555                 560

Glu Val Tyr Lys Thr Val Ser Met Arg Leu Asn Ile Val Ser Pro Asp
                565                 570                 575

Leu Ser Gly Lys Gly Leu Val Leu Pro Ser Val Leu Gly Ile Thr Phe
                580                 585                 590

Gly Ala Phe Leu Ile Gly Ala Leu Leu Thr Ala Ala Leu Trp Tyr Ile
            595                 600                 605

Tyr Ser His Thr Arg Gly Pro Ser Lys Arg Glu Pro Val Val Ala Val
            610                 615                 620

Ala Ala Pro Ala Ser Ser Glu Ser Ser Ser Thr Asn His Ser Ile Gly
625                 630                 635                 640

Ser Thr Gln Ser Thr Pro Cys Ser Thr Ser Ser Met Ala
                645                 650
```